(12) United States Patent
Pokorski

(10) Patent No.: US 11,246,956 B2
(45) Date of Patent: *Feb. 15, 2022

(54) POLYMER NANOFIBER SCAFFOLDS AND USES THEREOF

(71) Applicant: CASE WESTERN RESERVE UNIVERSITY, Cleveland, OH (US)

(72) Inventor: Jonathan Pokorski, San Diego, CA (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/820,158

(22) Filed: Mar. 16, 2020

(65) Prior Publication Data

US 2021/0015961 A1    Jan. 21, 2021

Related U.S. Application Data

(63) Continuation of application No. 15/961,712, filed on Apr. 24, 2018, now Pat. No. 10,588,997, which is a (Continued)

(51) Int. Cl.
| | |
|---|---|
| *A61L 15/26* | (2006.01) |
| *A61L 27/34* | (2006.01) |
| *A61L 15/44* | (2006.01) |
| *A61L 27/60* | (2006.01) |
| *A61F 2/02* | (2006.01) |
| *A61L 27/56* | (2006.01) |
| *A61L 15/42* | (2006.01) |
| *A61L 27/18* | (2006.01) |

(52) U.S. Cl.
CPC ............... *A61L 15/26* (2013.01); *A61F 2/02* (2013.01); *A61L 15/425* (2013.01); *A61L 15/44* (2013.01); *A61L 27/18* (2013.01); *A61L 27/34* (2013.01); *A61L 27/56* (2013.01); *A61L 27/60* (2013.01); *A61L 2400/12* (2013.01)

(58) Field of Classification Search
CPC . A61F 2/02; A61L 15/22; A61L 15/26; A61L 15/44; A61L 2400/12; A61L 27/44; A61L 27/60
See application file for complete search history.

(56) References Cited

U.S. PATENT DOCUMENTS 10,010,646 B2 *   7/2018   Pokorski ................... A61F 2/02
10,576,181 B2 *   3/2020   Pokorski ................. A61L 27/60
(Continued)

FOREIGN PATENT DOCUMENTS

| CN | 101215736 A | 7/2008 |
| WO | 2013/155519 A1 | 10/2013 |
| WO | 2014/022535 A1 | 2/2014 |

OTHER PUBLICATIONS

Vinsova, et al., "Recent Advances in Drugs and Prodrugs Design of Chitosan", Current Pharmaceutical Design, 2008, 14, 1311-1326.

*Primary Examiner* — Ernst V Arnold
(74) *Attorney, Agent, or Firm* — Tarolli, Sundheim, Covell & Tummino LLP

(57) ABSTRACT

A polymer nanofiber scaffold includes a plurality of melt extruded nanofibers that are chemically modified to append surface functionality to the nanofibers.

20 Claims, 24 Drawing Sheets

Specification includes a Sequence Listing.

Related U.S. Application Data continuation-in-part of application No. 15/118,030, filed as application No. PCT/US2015/015243 on Feb. 10, 2015, now Pat. No. 10,010,646.

(60) Provisional application No. 62/489,263, filed on Apr. 24, 2017, provisional application No. 61/937,756, filed on Feb. 10, 2014.

(56) References Cited

U.S. PATENT DOCUMENTS

| | | |
|---|---|---|
| 2008/0153163 A1 | 6/2008 | Mao et al. |
| 2010/0233458 A1 | 9/2010 | Sun et al. |
| 2011/0020917 A1 | 1/2011 | Wen et al. |
| 2011/0189287 A1 | 8/2011 | Abbott et al. |
| 2012/0052042 A1 | 3/2012 | Ladet et al. |
| 2012/0156135 A1 | 6/2012 | Farokhzad et al. |

* cited by examiner

Two different chemistries on PCL fiber bundle
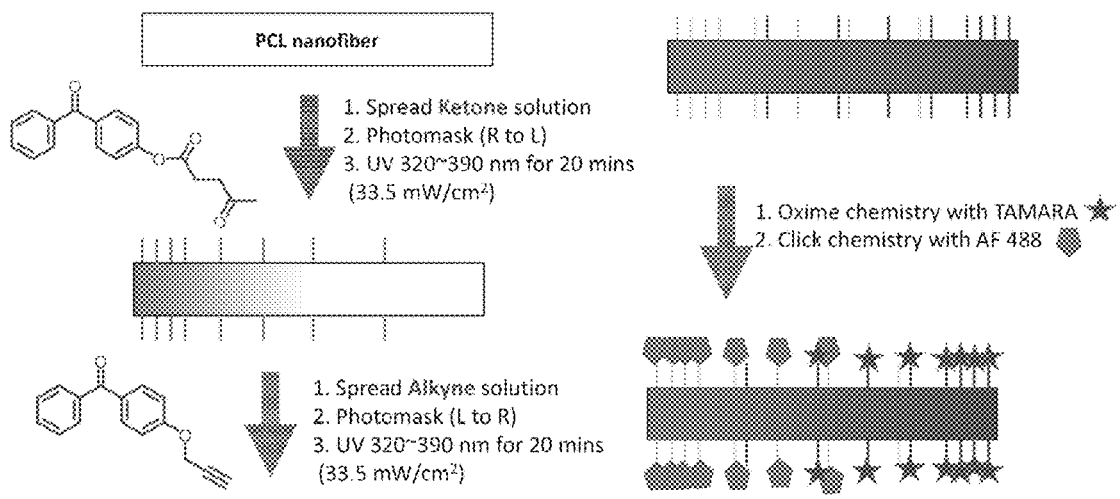
Fig. 6
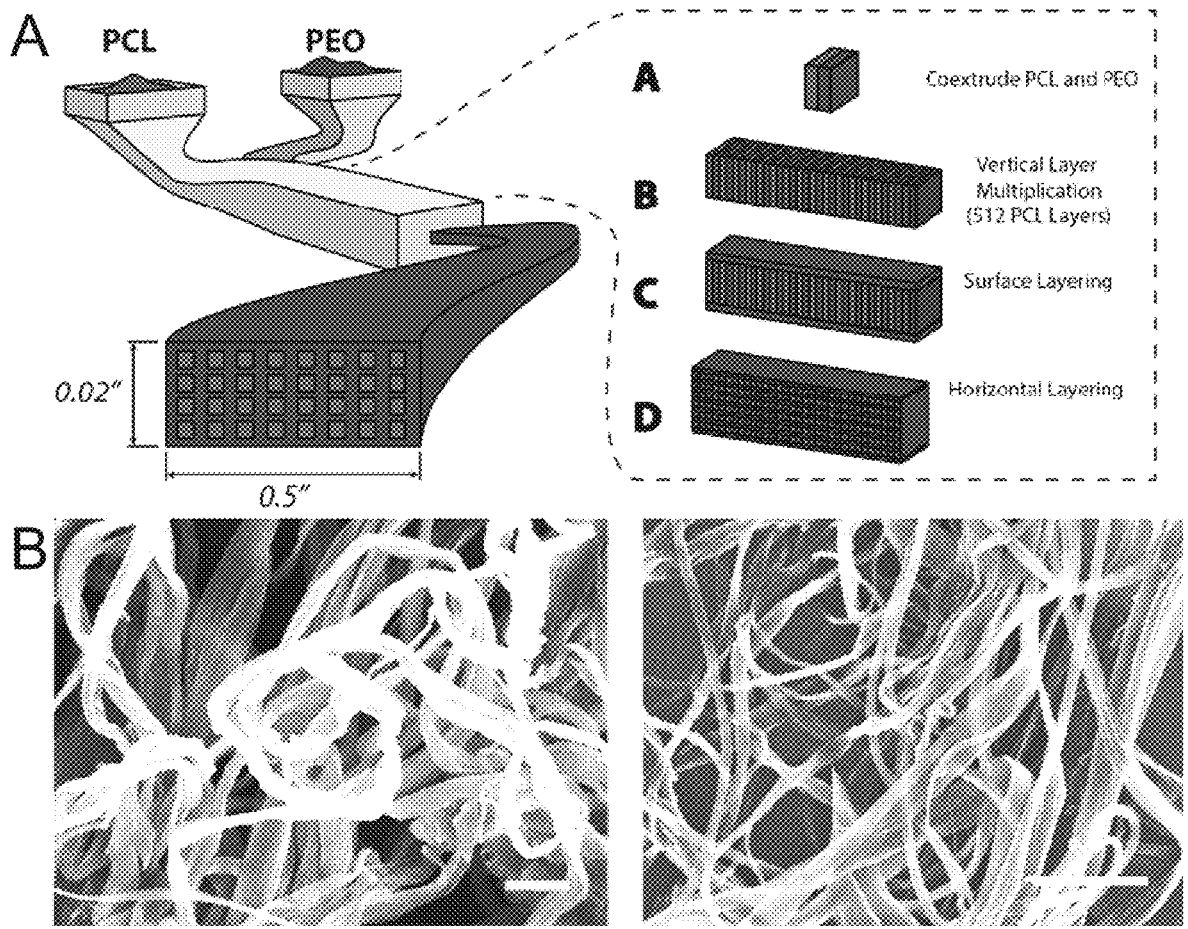
Figs. 7A-B

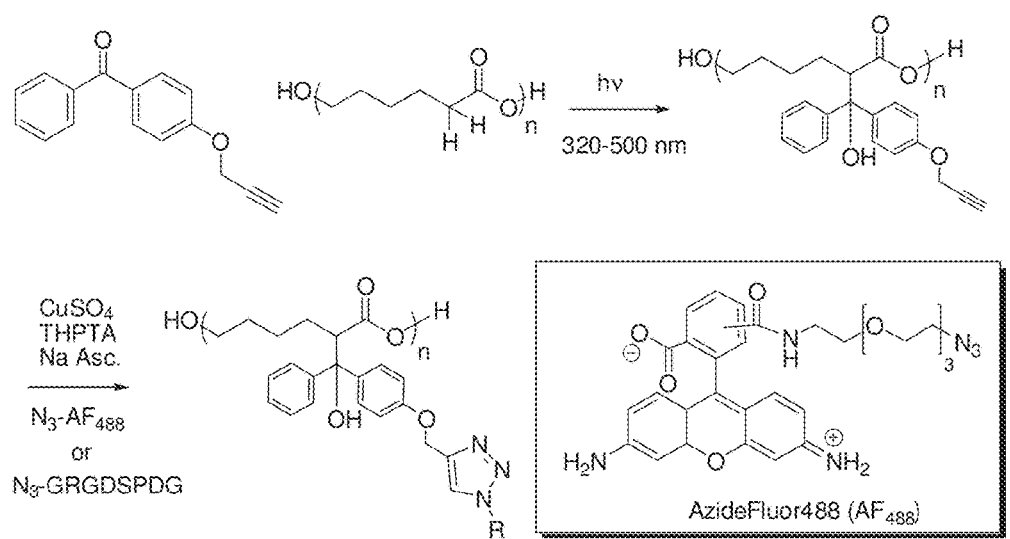
Fig. 8
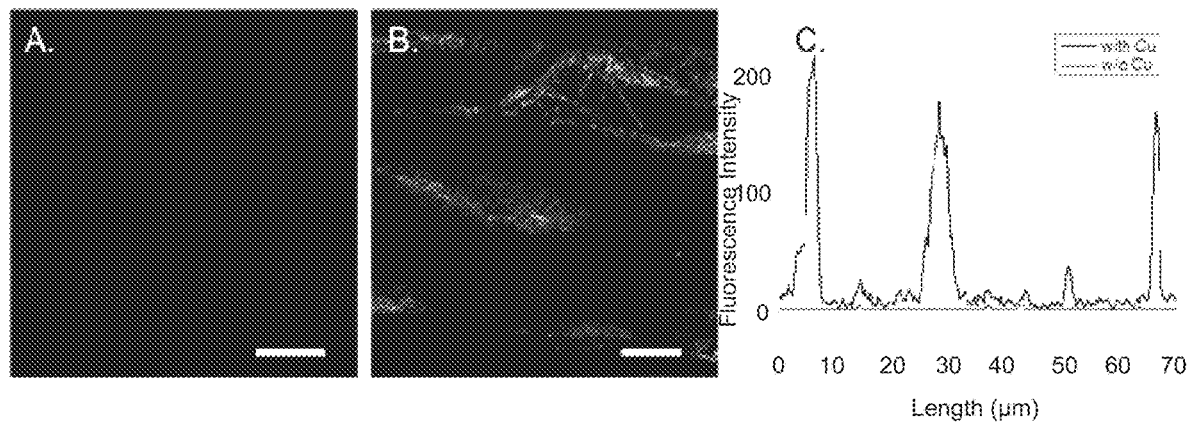
Figs. 9A-C

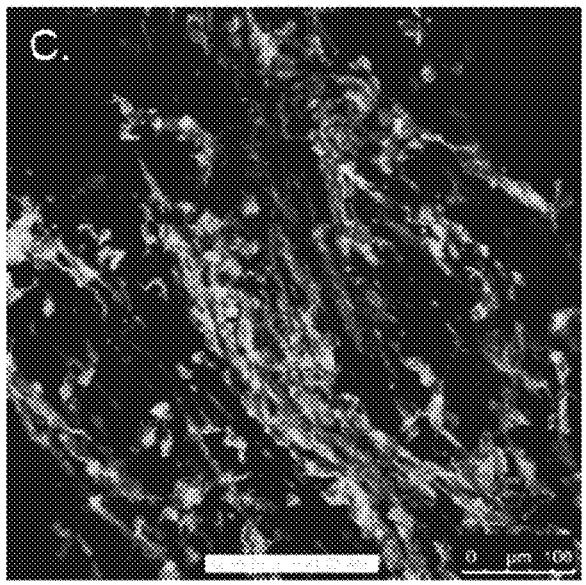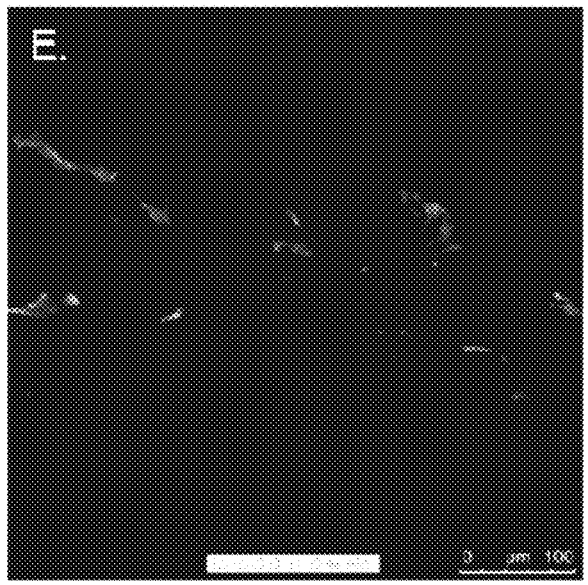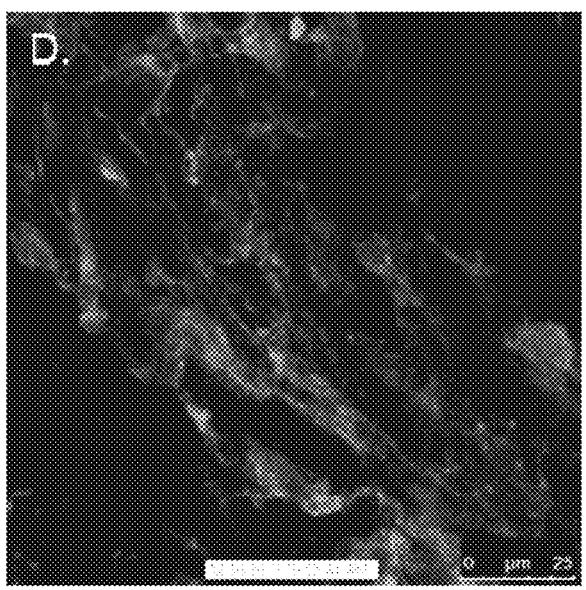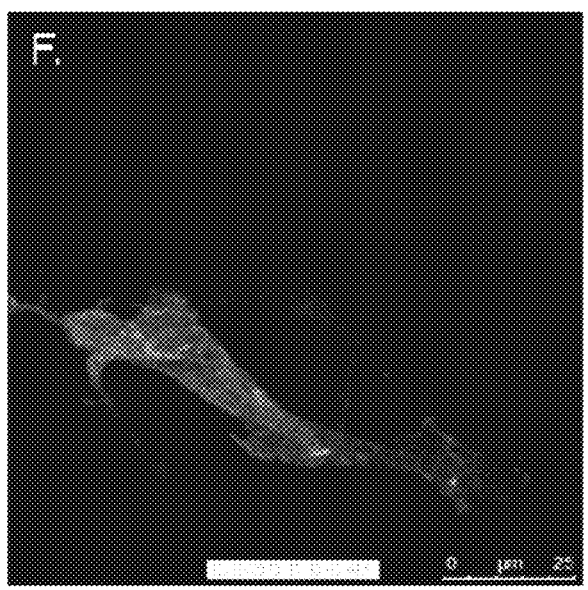
Figs. 10C-F

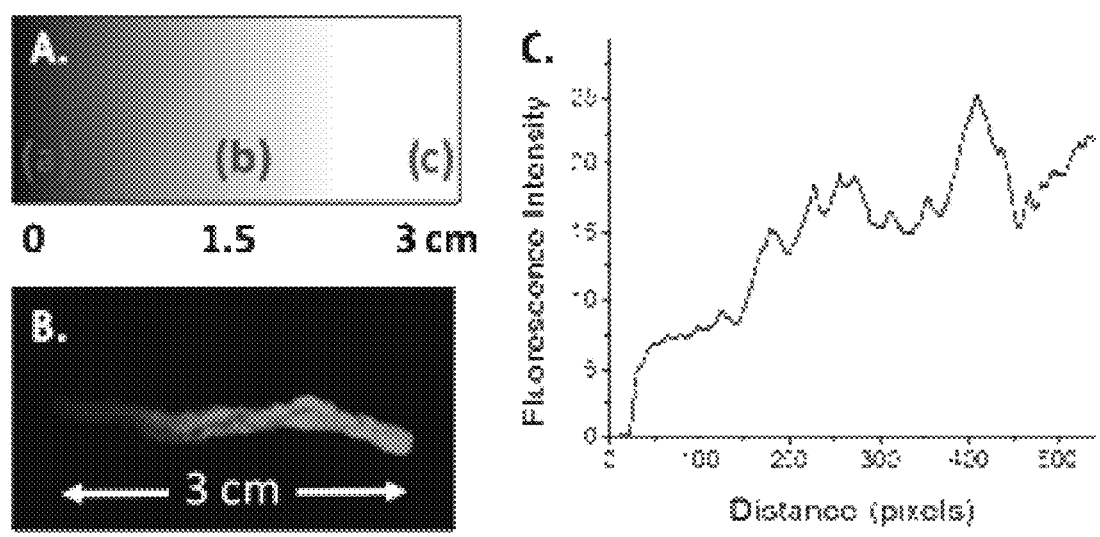
Figs. 12A-C
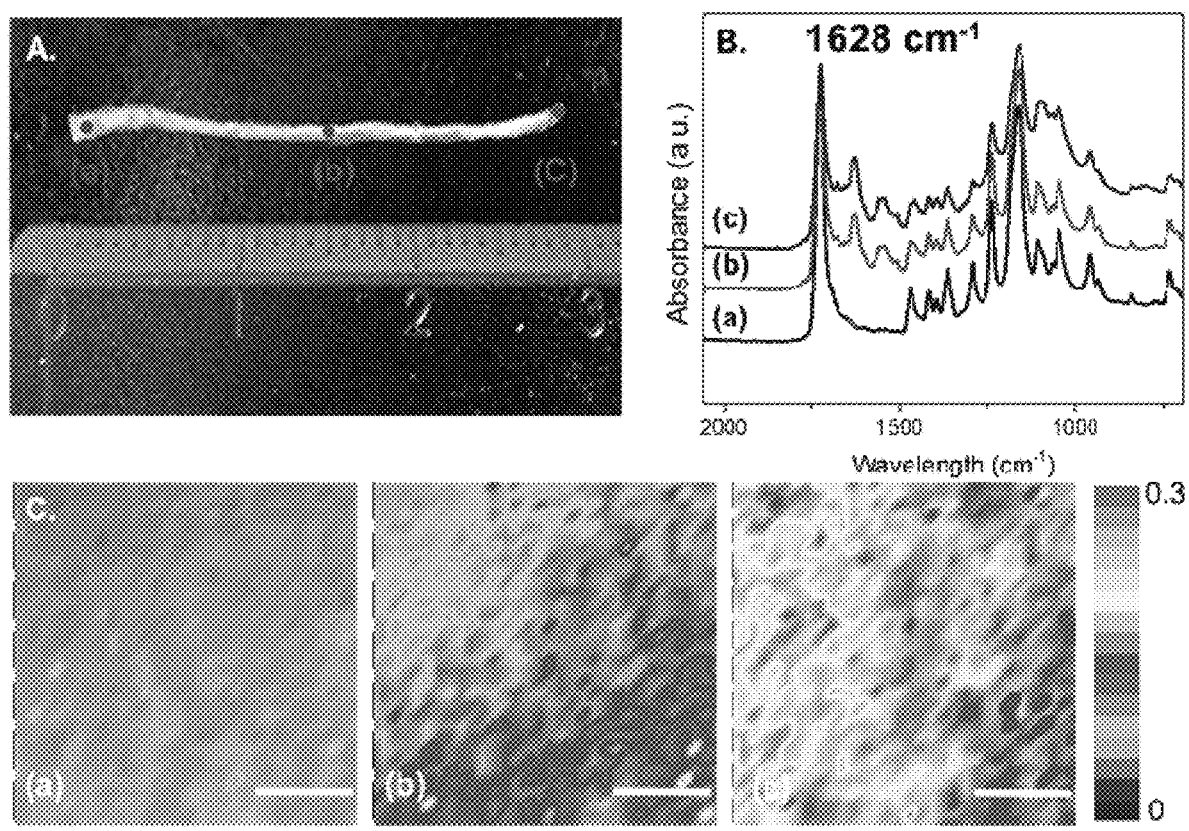
Figs. 13A-C

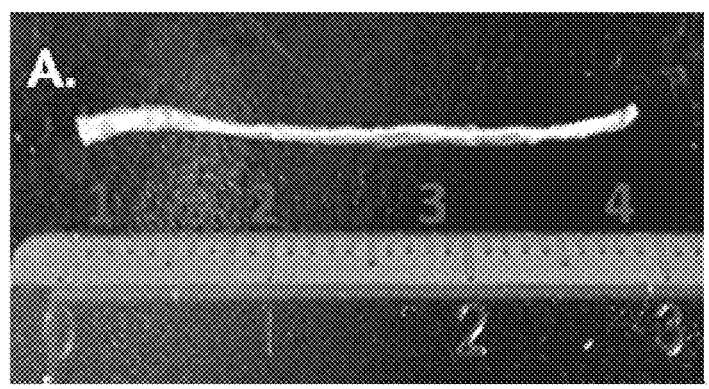
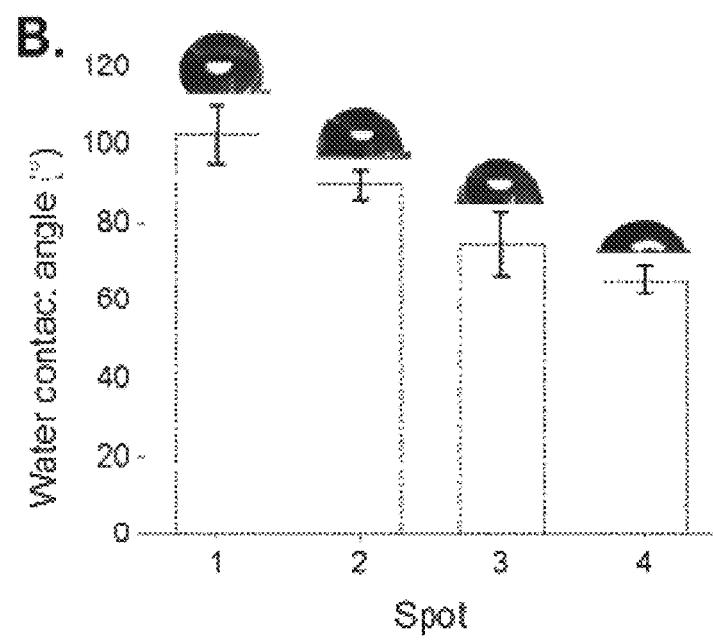
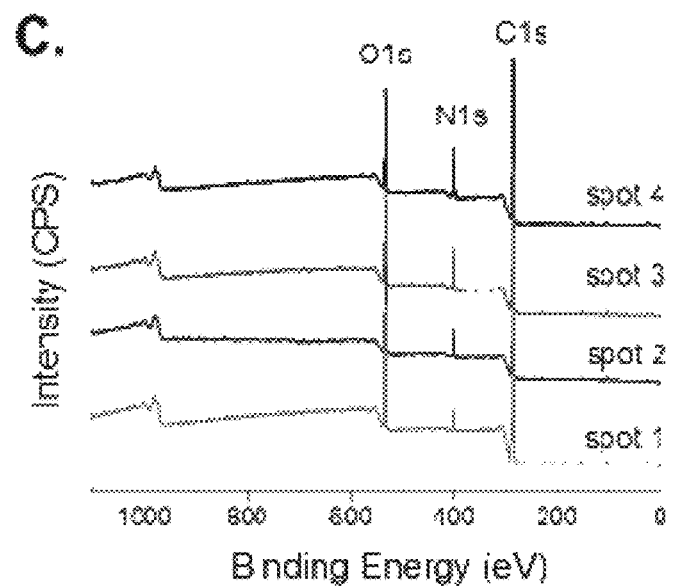
Figs. 14A-C

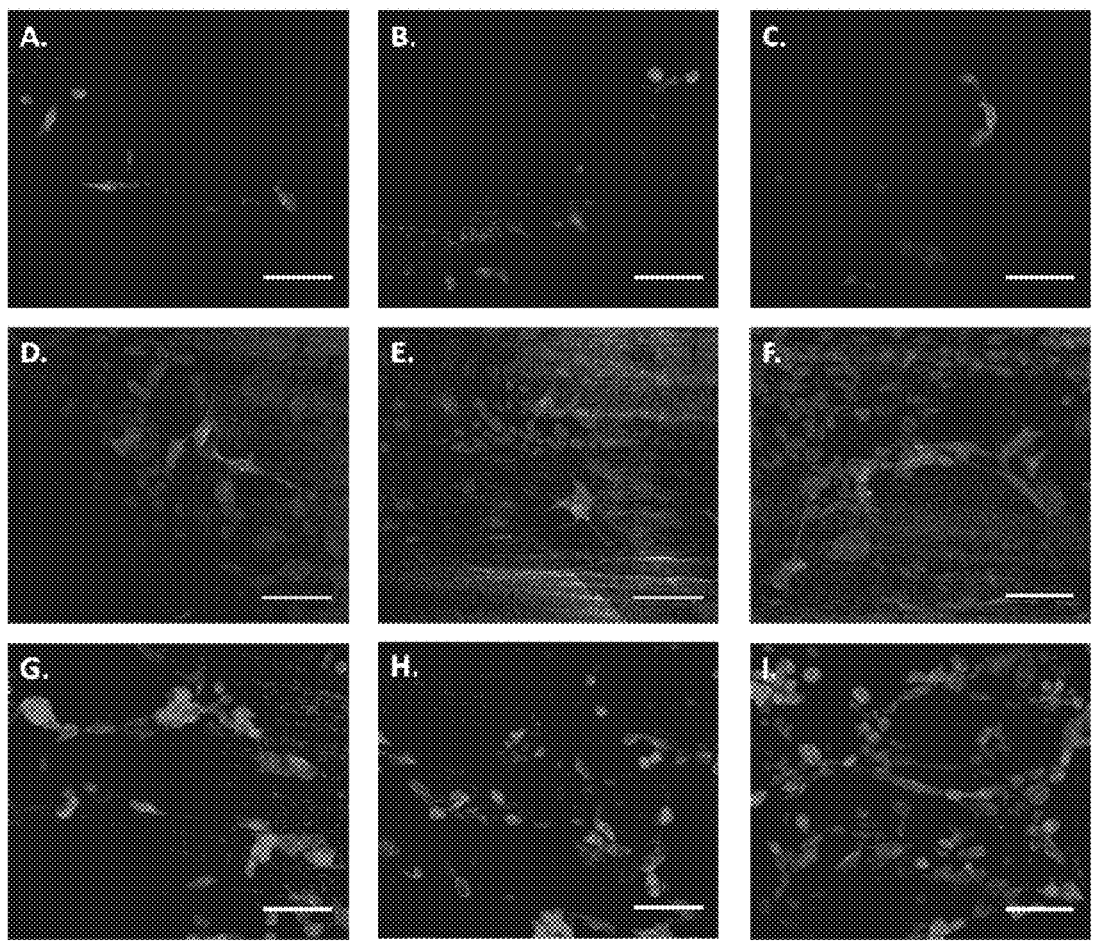
Figs. 15A-I
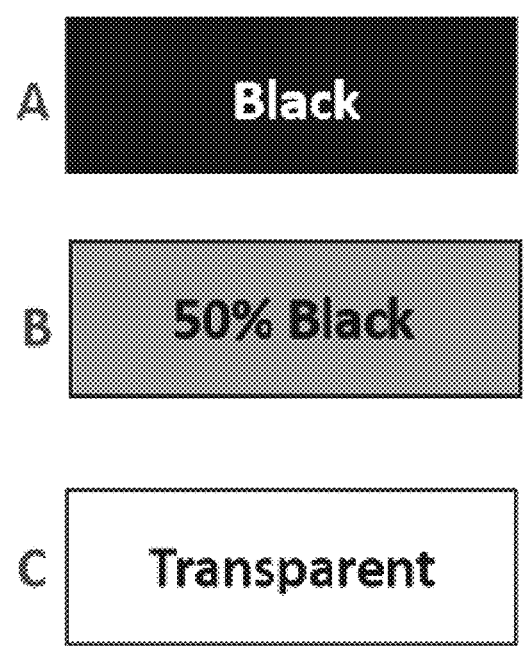
Figs. 16A-C

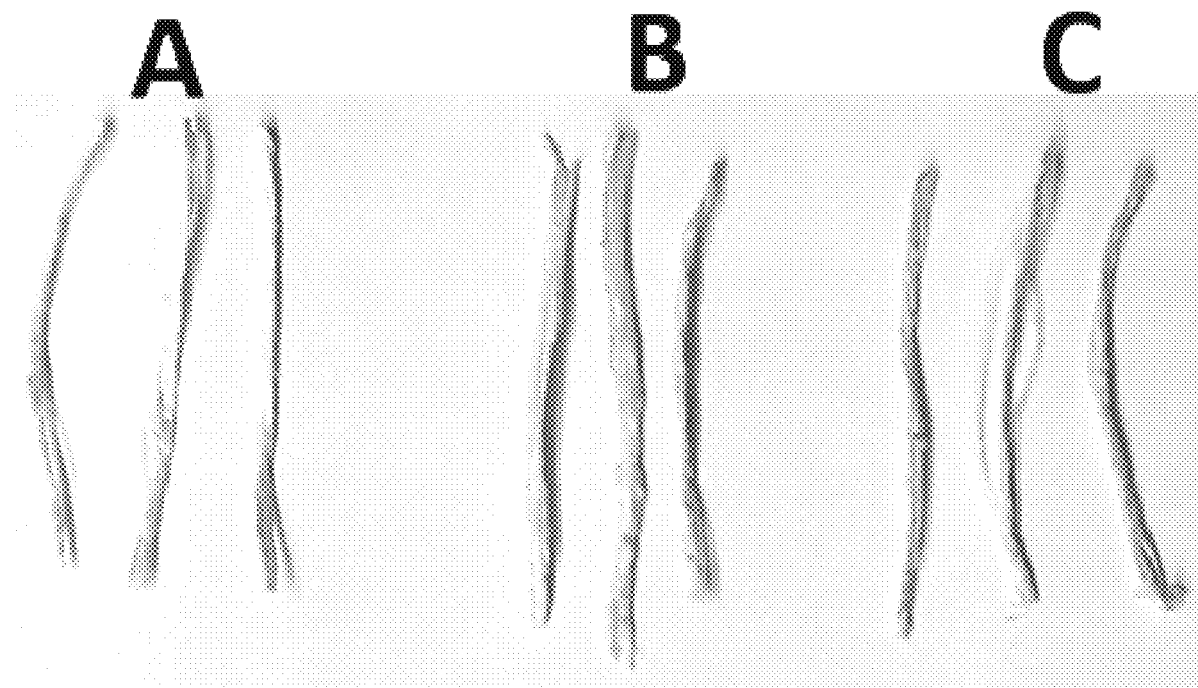
Figs. 17A-C

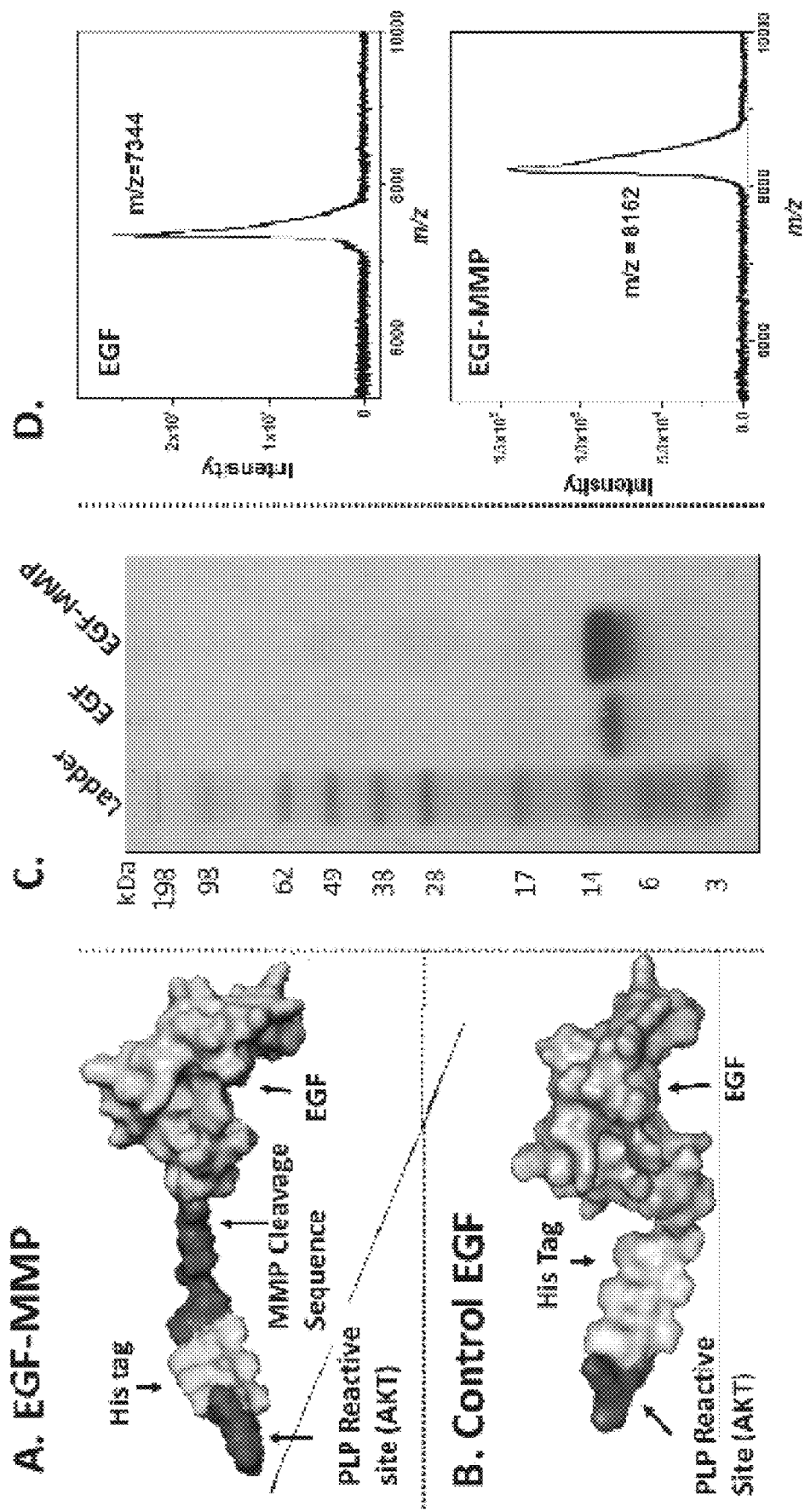
Figs. 18A-D

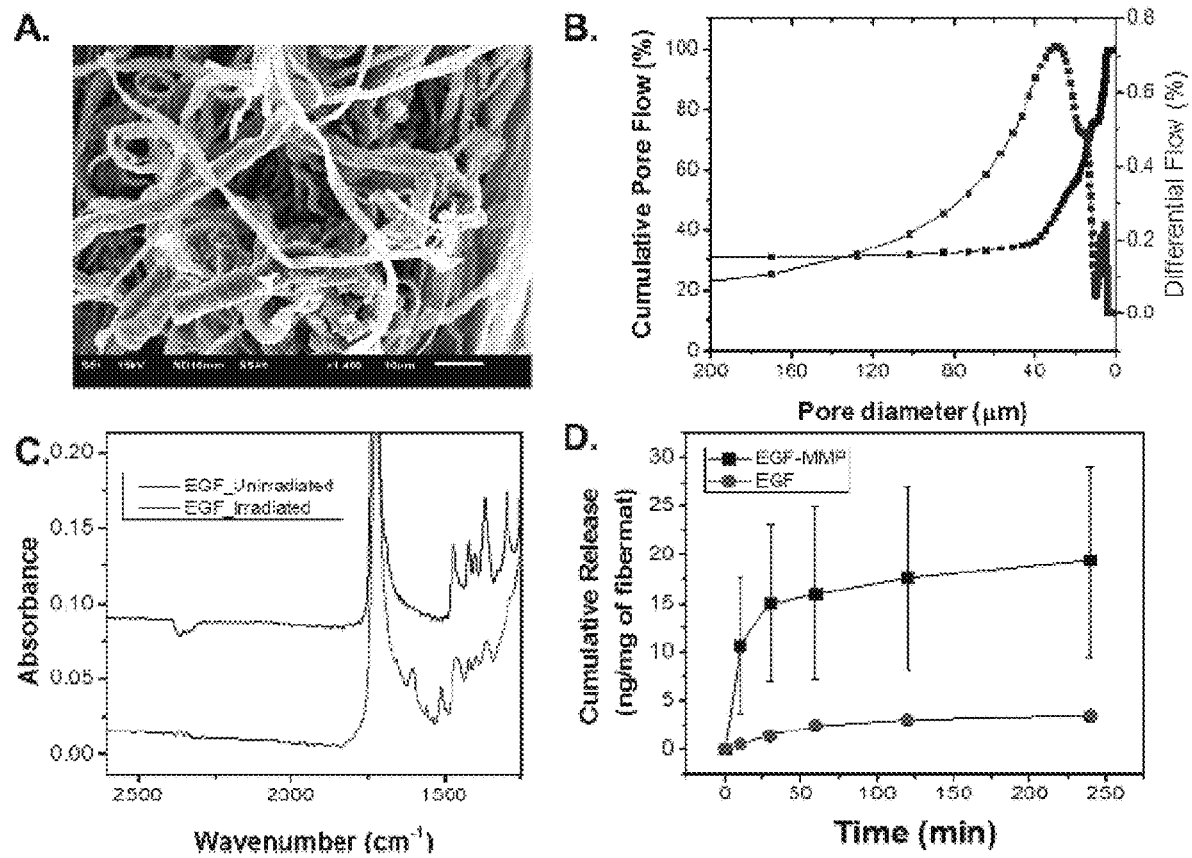
Figs. 20A-D

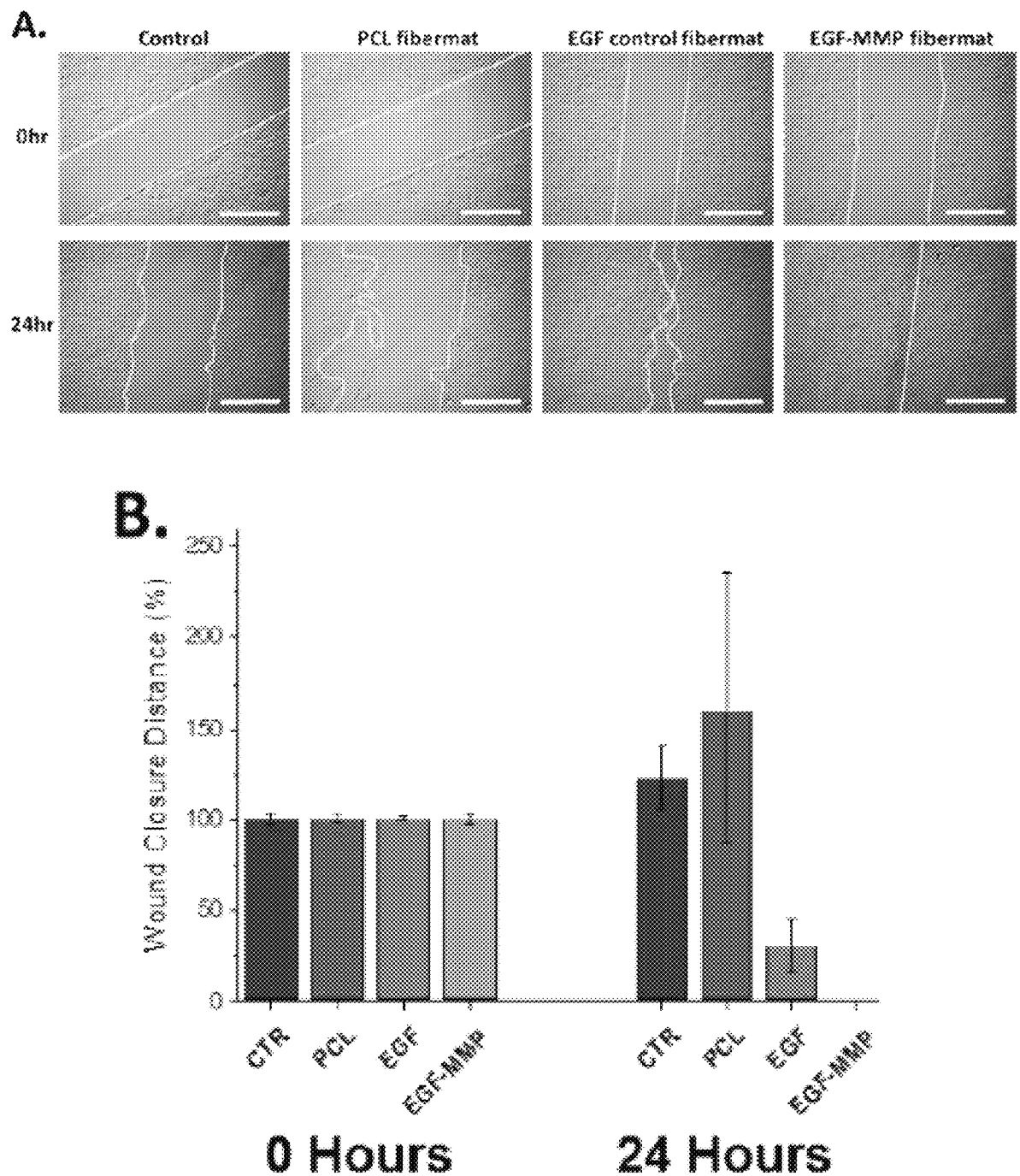
Figs. 21A-B

A

```
                        SEQUENCE LISTING

<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Val Pro Leu Ser Leu Tyr Ser Gly
1               5

<210> SEQ ID NO 2
<211> LENGTH: 70
<212> TYPE: PRT
<213> ORGANISM: Artificial Sequence
<220> FEATURE:
<223> OTHER INFORMATION: Synthetic Construct

<400> SEQUENCE: 2

Ala Lys Thr His His His His His Val Pro Leu Ser Leu Tyr Ser
1               5                   10                  15

Gly Asn Ser Asp Ser Glu Cys Pro Leu Ser His Asp Gly Tyr Cys Leu
            20                  25                  30

His Asp Gly Val Cys Met Tyr Ile Glu Ala Leu Asp Lys Tyr Ala Cys
        35                  40                  45

Asn Cys Val Val Gly Tyr Ile Gly Glu Arg Cys Gln Tyr Arg Asp Leu
    50                  55                  60

Lys Trp Trp Glu Leu Arg
65                  70

<210> SEQ ID NO 3
<211> LENGTH: 236
<212> TYPE: PRT
<213> ORGANISM: Artificial Sequence
<220> FEATURE:
<223> OTHER INFORMATION: Synthetic Construct

<400> SEQUENCE: 3

Ala Thr Gly Cys Thr Ala Cys Cys Ala Thr Gly Gly Cys Thr Ala Ala
1               5                   10                  15

Ala Ala Cys Cys Cys Ala Cys Cys Ala Cys Cys Ala Cys Cys Ala Cys
            20                  25                  30

Cys Ala Cys Cys Ala Cys Gly Thr Thr Cys Cys Gly Cys Thr Gly Thr
        35                  40                  45

Cys Thr Cys Thr Gly Thr Ala Cys Thr Cys Thr Gly Gly Thr Ala Ala
    50                  55                  60

Cys Thr Cys Thr Gly Ala Cys Thr Cys Thr Gly Ala Ala Thr Gly Cys
```

-continued

```
65                  70                  75                  80

Cys Cys Gly Cys Thr Gly Thr Cys Thr Cys Ala Cys Gly Ala Cys Gly
                85                  90                  95

Gly Thr Thr Ala Cys Thr Gly Cys Cys Thr Gly Cys Ala Cys Gly Ala
            100                 105                 110

Cys Gly Gly Thr Gly Thr Thr Thr Gly Cys Ala Thr Gly Thr Ala Cys
        115                 120                 125

Ala Thr Cys Gly Ala Ala Gly Cys Thr Cys Thr Gly Gly Ala Cys Ala
    130                 135                 140

Ala Ala Thr Ala Cys Gly Cys Thr Thr Gly Cys Ala Ala Cys Thr Gly
145                 150                 155                 160

Cys Gly Thr Thr Gly Thr Thr Gly Gly Thr Thr Ala Cys Ala Thr Cys
                165                 170                 175

Gly Gly Thr Gly Ala Ala Cys Gly Thr Thr Gly Cys Cys Ala Gly Thr
            180                 185                 190

Ala Cys Cys Gly Thr Gly Ala Cys Cys Thr Gly Ala Ala Ala Thr Gly
        195                 200                 205

Gly Thr Gly Gly Gly Ala Ala Cys Thr Gly Cys Gly Thr Thr Ala Ala
    210                 215                 220

Cys Thr Cys Gly Ala Gly Thr Gly Ala Cys Thr Cys
225                 230                 235

<210> SEQ ID NO 4
<211> LENGTH: 62
<212> TYPE: PRT
<213> ORGANISM: Artificial Sequence
<220> FEATURE:
<223> OTHER INFORMATION: Synthetic Construct
<400> SEQUENCE: 4

Ala Lys Thr His His His His His His Asn Ser Asp Ser Glu Cys Pro
1               5                   10                  15

Leu Ser His Asp Gly Tyr Cys Leu His Asp Gly Val Cys Met Tyr Ile
            20                  25                  30

Glu Ala Leu Asp Lys Tyr Ala Cys Asn Cys Val Val Gly Tyr Ile Gly
        35                  40                  45

Glu Arg Cys Gln Tyr Arg Asp Leu Lys Trp Trp Glu Leu Arg
    50                  55                  60
```

POLYMER NANOFIBER SCAFFOLDS AND USES THEREOF

RELATED APPLICATION

This application claims priority to U.S. Provisional Ser. No. 62/489,263, filed Apr. 24, 2017, this application is also a Continuation-in-Part of U.S. Ser. No. 15/118,030, filed Aug. 10, 2016, which is a National Phase Filing of PCT/US2015/015243, filed Feb. 10, 2015, which claims priority to U.S. Provisional Application Ser. No. 61/937,756, filed Feb. 10, 2014, the subject matter of which is incorporated herein by reference in its entirety.

GOVERNMENT FUNDING

This invention was made with government support under Grant No. R00EB011530 awarded by The National Institutes of Health and DMR 0423914 awarded by The National Science Foundation. The United States government has certain rights to the invention.

BACKGROUND

Traditional industrial processes for synthetic polymer microfiber spinning can be classified as either solvent-based or melt-based. As the name implies, solvent processing involves the spinning of a polymer solution with solidification of the fiber either through coagulation in a non-solvent (wet-spinning) or solvent evaporation (dry-spinning). In contrast, melt spinning produces fibers via the spinning of molten polymer that solidifies upon cooling; drawing usually accompanies this melt-based process to induce chain orientation and enhance mechanical properties. Typically, accessing nanoscale cross-sections is difficult, where fiber diameters of only 10-20 µm are achieved with applications in the textile industry. Pushing the limits of fiber production to the nanoscale has garnered recent attention in the processing arena.

Electrospinning is perhaps the most well-known, and one of the oldest techniques for generating sub-micron fibers in lab-scale from a polymer solution, or less commonly, a polymer melt via the application of a large electric field. This charged polymer jet is subjected to electrostatic forces, which act to elongate, thin, and solidify the polymer fiber in the characteristic "whipping instability" region. Although some success has been achieved with electrospun fibers in high-value added applications, such as air filtration, topical drug delivery, and tissue engineering scaffolds, significant disadvantages are low throughput and scalability. Additionally, electrospinning necessitates large volumes of toxic solvents that must be recovered by specialized equipment to make the process viable on a large scale.

Other approaches to nanofiber fabrication have emerged, including rotary-jet spinning, gas jet blowing, melt blowing, and bicomponent fiber spinning. Recent advances in rotary jet spinning have focused on a melt-based approach to nanofiber production with throughputs significantly higher than electrospinning, but improvements are ongoing to address processing complexity as it relates to broad applicability to a range of polymer systems. Melt blowing is a particularly commercially relevant and scalable technique for achieving fiber diameters on the order of tens of microns and higher; in this process, fibers are generated in-line by extrusion of a polymer through a die orifice, while a hot air jet blows down the extrudate. It is process compatible with a wide range of polymers, and is a solvent-less and environmentally-friendly manufacturing method. However, the pursuit of nanoscale fibers has been limited primarily to polypropylene for air filtration. Collectively, these limitations on nanofiber scalability increase manufacturing costs and lower productivity.

Polymeric materials have become ubiquitous in regenerative medicine as scaffolds for cell-seeding, where they have found application in the induction of cellular adhesion, proliferation, and differentiation. Nano-fibrous scaffolds are of particular use as they are porous, allowing transport of nutrients and waste products, have high surface area to volume ratios, and can provide directed cell growth based on fiber alignment. Synthetic fibers for regenerative medicine are usually comprised of polyesters, often poly(lactic acid) (PLA), poly(lactic-co-glycolic acid) (PLGA) or poly(caprolactone) (PCL), due to their degradability via hydrolytic pathways and resultant non-toxic byproducts. However, most polymeric scaffolds are unable to promote biological effects, as synthetic polymers do not possess the biochemical cues that are necessary to impact a cell's fate.

Modification of these polyester fibers typically relies on the degradation of the polymer chains, either through hydrolysis to expose carboxylic acids and alcohols, or through aminolysis to expose a second functional group off of the amine. Both of these routes degrade the polymer, potentially resulting in reduced mechanical properties and increased erosion of the fibers. Recent work has aimed to ameliorate this through the synthesis of telechelic polymers, which could then be processed into a scaffold.

SUMMARY

Embodiments described herein relate to a polymer nanofiber scaffolds and to their use in, for example, tissue engineering, drug delivery, wound healing, chemical processing, nanoelectronics, fabrics, and filtration applications. In some embodiments, a polymer nanofiber scaffold can include a plurality of melt extruded polymer nanofibers. The nanofibers can each have a rectangular cross-section defined in part by an encapsulating polymer material that is separated from the nanofibers. The nanofibers include a plurality of click-reactive functional groups of specific binding pairs extending from portions of outer surfaces of the nanofibers. The functional groups can be chemically bound to the nanofibers without degrading polymer chains of the nanofibers. The functional groups can be appended to complementary click-reactive groups of the specific binding pair that are conjugated to at least one agent.

In some embodiments, the concentration of functional groups extending from the at least one portion can be at least about 0.1 nmol/cm$^2$. The agent conjugated to complementary click-reactive group, which can be appended to the functional group, can include at least one of a bioactive agent, diagnostic agent, therapeutic agent, catalyst, charged molecule, peptide, polypeptide, nucleic acid, polynucleotide, small molecule, nanoparticle, antibody, carbohydrate, or vector.

In other embodiments, the functional groups can be spatially arranged on the nanofibers such that a first portion of the nanofibers has a first concentration of functional groups and a second portion of the nanofibers has a second concentration of functional groups different than the concentration of the first portion, e.g., different portions of the nanofibers can have different concentrations of the same or different functional groups. In some embodiments, the functional groups can be arranged on the nanofibers in a concentration gradient.

In still other embodiments, the plurality of click-reactive function groups can include first click reactive functional groups and second click reactive functional groups different than the first click reactive functional groups.

In some embodiments, the functional groups are chemically bound to the nanofibers with diarylhydroxymethylene linkages that are formed by reaction of click-reactive functional group substituted diarylketones with the polymer chains of the nanofibers. The click-reactive functional groups can include at least one of an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, —$CO_2N(COCH_2)_2$, —$CO_2N(COCH_2)_2$, —$CO_2H$, —CHO, —$CHOCH_2$, —N=C=O, —$SO_2CH=CH_2$, —$N(COCH)_2$, —S—S—($C_5H_4N$) and groups of the following structures:

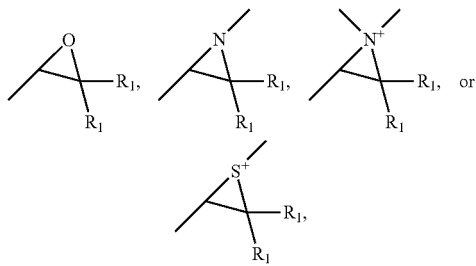

wherein $R_1$ is hydrogen or $C_1$ to $C_4$ alkyl.

In other embodiments, the nanofibers can be formed of a biocompatible or cytocompatible polymer, such as a polyester (e.g., polycaprolactone).

Other embodiments described herein relate to a method of forming an agent functionalized polymer nanofiber scaffold. The method includes providing a plurality of melt extruded polymer nanofibers. The nanofibers can each have a rectangular cross-section defined in part by an encapsulating polymer material that is separated from the nanofibers. A plurality of click-reactive functional groups of a specific binding pair can then be chemically bound to the fibers without degrading polymer chains of the nanofibers. The click-reactive functional groups can extend from portions of outer surfaces of the nanofibers. At least one agent is appended to the nanofibers by reacting the agent conjugated to a complementary click-reactive group of the specific binding pair with the click-reactive functional groups of the nanofibers.

In some embodiments, the agent can include at least one bioactive agent, diagnostic agent, therapeutic agent, catalyst, charged molecule, peptide, polypeptide, nucleic acid, polynucleotide, small molecule, nanoparticle, antibody, carbohydrate, or vector.

In other embodiments, the nanofibers can be formed by coextruding a first polymer material with a second polymer material to form a coextruded polymer film having discrete overlapping layers of polymeric material; multiplying the overlapping layers to form a multilayered composite film; and separating the first polymer material from the second polymer material to form the plurality of nanofibers having the rectangular cross-section. Separating the polymer materials can include, for example, subjecting the multilayered composite film to a high pressure water stream or a high pressure air stream, or dissolving the second polymer material.

In some embodiments, the functional groups are spatially arranged on the nanofibers such that a first portion of the nanofibers has a first concentration of functional groups and a second portion of the nanofibers has a second concentration of functional groups different than the concentration of first portion. The functional groups can be appended to complementary click-reactive groups that are conjugated to at least one agent to provide a first concentration of agents on the first portion and a second concentration of agents on the second portion.

In other embodiments, the functional groups can be spatially arranged on the nanofibers such that different portions of the nanofibers have different concentrations of the functional groups. The functional groups can be appended to complementary click-reactive groups that are conjugated to at least one agent to provide different concentrations of agents on different portions of the nanofibers.

In still other embodiments, the plurality of click-reactive function groups can include first click reactive functional groups and second click reactive functional groups different than the first click reactive functional groups. The first click reactive functional groups can appended to first agents and the second click reactive functional groups can be appended to second agents different than the first agents.

In some embodiments, the concentration of the functional click-reactive function groups and appended agent extending from at least one portion of the nanofibers is at least about 0.1 nmol/cm$^2$. The appended agent can be a bioactive agent that promotes at least one of cell adhesion, growth, or proliferation and the polymer scaffold can be used in at least one of biomedical, tissue engineering, and/or wound healing applications, such as a wound dressing or engineered tissue construct.

BRIEF DESCRIPTION OF THE DRAWINGS

FIG. 6 is a schematic illustration of a nanofiber surface functionalized with two different chemistries FIGS. 7(A-B) illustrate: (A) schematic of co-extrusion and 2-dimensional multiplication system for producing nanofibers (top); and (B) scanning electron micrograph of the as-extruded nanofibers following PEO dissolution (bottom). Scale bar (left)=20 μm, right=50 μm.

FIG. 8 illustrates a chemical scheme for modification of PCL nanofibers.

FIGS. 9(A-C) illustrate fluorescent confocal micrographs of PCL nanofibers. A) PCL nanofiber control with no $CuSO_4$ added during reaction with $AF_{488}$. Scale bar=50 μm. B) PCL after the CuAAC reaction with $AF_{488}$, including $CuSO_4$. Scale bar=50 μm. C) Fluorescent intensity in the region of interest, as indicated by the red lines in images A and B. The red line on the graph corresponds to image A, and the black line is indicative of image B.

FIGS. 12(A-C) illustrate: A) schematic of gradient photomask as inkjet printed onto transparency sheets: (a) is 100% black, (b) is 50% of black and (c) is transparent as indicated in the text; B) Fluorescence image of PCL-AF488 fiber gradient; and C) plot of fluorescence intensity over the total fiber distance, indicating an approximate linear gradient of intensity.

FIGS. 13(A-C) illustrate: A) Digital image of PCL gradient-modified IKVAV fibers, indicating points where IR spectra were taken. B) ATR-FTIR spectrum of varying spots on the PCL gradient (indicated in A). The arrow indicates the amide I region derived from the IKVAV peptide. C) ATR-FTIR imaging at 1628 $cm^{-1}$ (scale bar=50 µm, intensity is indicated by a heat map as is indicated on the right).

FIGS. 14(A-C) illustrate: A) Digital image of IKVAV gradient fibers, indicating spots taken for water contact angle and X-ray photoelectron spectroscopy. B) Water contact angle)(°) of PCL-g-IKVAV fibers with four distinct spots from left (low peptide concentration) to right (high peptide concentration). Error bars represent standard deviation (n=3). C) Full XPS wide scan from left to right of PCL-gradient (spots 1-4), as indicated in A. IKVAV fibers shows increasing intensity of nitrogen (N1s) with increasing UV irradiation intensity.

FIGS. 15(A-I) illustrate confocal microscopy images of PC-12 cells. Cells were cultured for 5 days and stained with DAPI and anti β-III-tubulin. Fiber orientation is approximately horizontal. A-C) PC-12 cells cultured on unmodified PCL, corresponding to spots (a), (b) and (c). D-F) PC-12 cells cultured on PCL-ng-IKVAV which correspond spot (a), (b) and (c) in FIG. 12A. G-I) PC-12 cells cultured on 3 different regions of PCL-g-IKVAV which correspond spot (a), (b) and (c). The direction of the gradient is left to right, where G is the lowest peptide concentration and I is the highest. (Scale bar=50 µm).

FIGS. 16(A-C) illustrate non-gradient photomasks which correspond to different intensities of the gradient photomask. A) 100% black photomask corresponding to the least amount of UV fluence in the gradient photomask. B) 50% black photomask where UV intensity corresponds to the exact center of the gradient photomask. C) Transparent photomask corresponding to the highest UV fluence through the gradient photomask.

FIGS. 17(A-C) illustrate images showing $AF_{488}$ clicked PCL fiberbundles; Top: Digital image of fibers corresponding to the individual photomasks in FIG. 16. Groups A, B, and C fibers used photomask A, B, and C to perform photochemistry with Pr-Bz before click chemistry. The table indicates the intensity of UV light and the surface coverage of dyes conjugated onto fibers (n=3).

FIGS. 18(A-D) illustrate (A) EGF-MMP, (B) EGF control protein, (C) SDSPAGE gel of purified control EGF (7.34 kDa) and EGF-MMP (8.16 kDa), (D) MALDI-TOF MS analysis of control EGF protein and EGF-MMP.

FIGS. 20(A-D) illustrate (A) SEM micrograph, fiber thickness=2.6±1.5 µm, Scale Bar=10 µm. (B) Pore size distribution of the fiber mat as measured via porimeter, mean pore diameter=25.6 µm. (C) ATR-FTIR spectrum of EGF-MMP conjugated to fiber mats. Black=unirradiated, Red=irradiated. (D) Kinetic study of released EGF and EGF-MMP from fiber mats after MMP-9 cleavage.

FIGS. 21(A-B) illustrate (A) Optical micrographs of gap distance between HaCaT cells at 0 and 24 hours after scratch test (scale bar=200 µm). (B) Relative scratch closure distance after 24 hours. Error bars are expressed as standard deviations.

DETAILED DESCRIPTION

Figure 1:
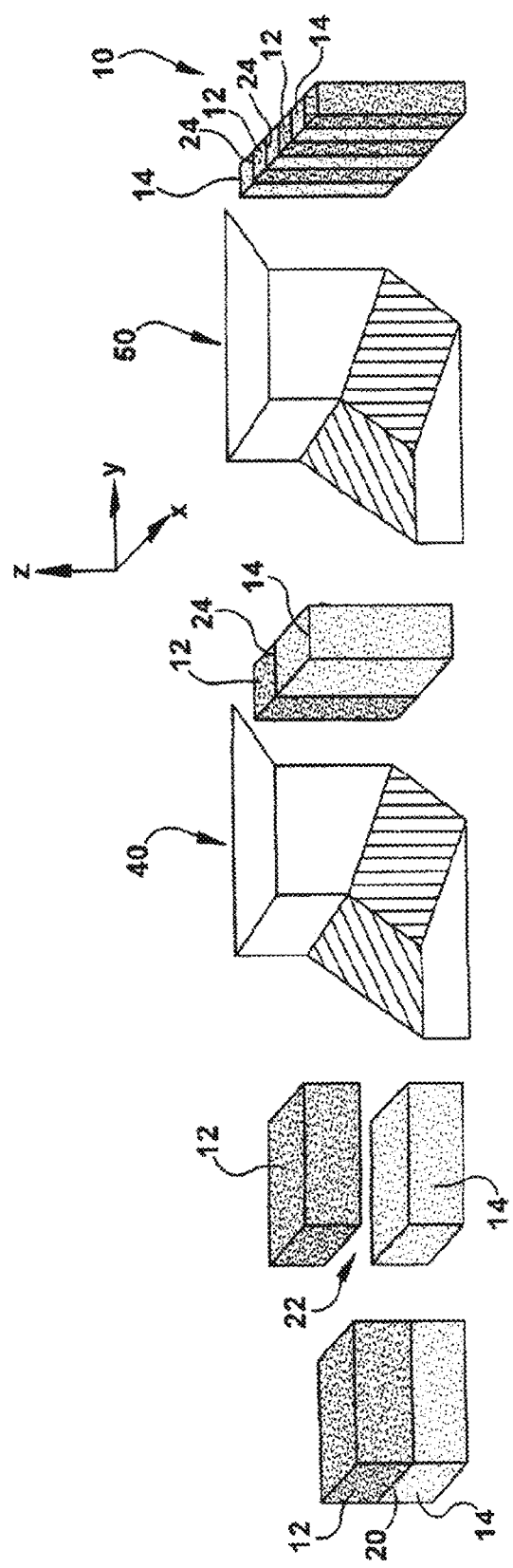
FIG. 1 is a schematic illustration of a coextrusion and layer multiplying process used to form a multilayered polymer composite film in accordance with an embodiment.

Embodiments described herein relate to surface functionalized polymer nano-fibrous (or nanofiber) scaffolds, methods of forming the surface functionalized polymer nanofiber scaffolds, and to the use of the scaffolds in, for example, tissue engineering, drug delivery, wound healing, chemical processing, nanoelectronics, fabrics, and filtration applications. The nanofiber scaffolds can include a plurality of non-woven or woven nanofibers that are formed from commodity polymers using a continuous extrusion process. The nanofibers can have a rectangular cross-section of about 10 nm (height)×10 nm (width) to about 10 µm×10 µm, with variations in between, and a surface area of at least about 1 $cm^2/g$ or more. The nanofibers and/or scaffold formed from the nanofibers can be chemically modified (or surface modified) non-destructively after formation to chemically bond click reactive functional groups of specific binding pairs onto the nanofibers such that the click-reactive functional groups extend uniformly across the surface of the nanofibers and/or scaffold or from selected portions of the nanofibers or scaffold at varying concentrations, types, and/or densities. Complementary click-reactive groups of the specific binding pairs conjugated to any number of any number of agents and/or chemical entities can be click-reacted with the click-reactive groups chemically bound to the nanofibers to the agents to the nanofibers. The agents appended to the click reactive groups of the fibers can include, for example, bioactive agents, diagnostic agents, therapeutic agents, catalysts, charged molecules, peptides, polypeptides, nucleic acids, polynucleotides, small molecules, nanoparticles, antibodies, carbohydrates, and vectors.

In some embodiments, one or more similar or different functional groups can be spatially arranged on the nanofibers such that different portions of the nanofibers have different concentrations of the functional groups. For example, a plurality of first functional groups can be arranged on the nanofibers in a first concentration gradient and/or a plurality of second functional groups can be arranged on the nanofibers in a second concentration gradient.

Advantageously, the nanofiber scaffold can be formed or fabricated using solely commercially available polymers, such as PCL and poly (ethylene oxide) (PEO). The process used to form the nanofiber scaffold can be solvent-free, allow for controllable cross-sectional dimensions of the fibers, and use FDA-friendly polymers during processing. The fabrication process is flexible because it involves the use of an extrusion line that is composed of several basic multipliers. Arrangement of these multipliers allows control over the number, as well as the dimensions, of fibers contained in one extrudate. In addition, the cross-sectional geometry of the nanofibers is rectangular creating greater surface area to volume ratios (e.g., at least about 1 $cm^2$/mg, at least about 10 $cm^2$/mg, at least about 20 $cm^2$/mg, at least about 40 $cm^2$/mg, at least about 50 $cm^2$/mg or more), when compared to cylindrical fibers. The increased surface area can allow for a higher concentration of surface modifications to be available on the fiber, potentially improving the display of chemical or biochemical cues.

The surface functionalized polymer nanofiber scaffold can be formed from a multilayered polymer composite film. FIG. 1 illustrates a coextrusion and multilayering process used to form a multilayered polymer composite film 10. First, a first polymer layer 12 and a second polymer layer 14 are provided. The first layer 12 is formed from a first polymeric material (a) and the second polymer layer 14 is formed from a second polymer material (b) that is substantially immiscible and has a similar viscosity with the first polymer material (a) when coextruded. It will be appreciated that one or more additional layers formed from the polymer materials (a) or (b) or a different polymer materials may be provided to produce the multilayered polymer composite film 10.

The term "polymer" or "polymeric material" as used in the present application denotes a material having a weight average molecular weight (Mw) of at least 5,000. Preferably the polymer is an organic polymeric material. The term "oligomer" or "oligomeric material" as used in the present application denotes a material with a weight average molecular weight of from 1,000 to less than 5,000. Such polymeric materials can be glassy, crystalline or elastomeric polymeric materials.

Examples of polymeric materials that can potentially be used for the first and second polymer materials (a), (b) include, but are not limited to, polyesters such as polylactic acid, poly(lactic-co-glycolic acid), polycaprolactone (PCL); and poly(ethylene naphthalate) and isomers thereof, such as 2,6-, 1,4-, 1,5-, 2,7-, and 2,3-polyethylene naphthalate; polyalkylene terephthalates such as polyethylene terephthalate, polybutylene terephthalate, and poly-1,4-cyclohexanedimeth-ylene terephthalate; polyimides, such as polyacrylic imides; polyetherimides; styrenic polymers, such as atactic, isotactic and syndiotactic polystyrene, α-methyl-polystyrene, para-methyl-polystyrene; polycarbonates, such as bisphenol-A-polycarbonate (PC); polyethylenes, such as polyethyele oxide (PEO); poly(meth)acrylates, such as poly(isobutyl methacrylate), poly(propyl methacrylate), poly(ethyl methacrylate), poly(methyl methacrylate), poly(butyl acrylate) and poly(methyl acrylate) (the term "(meth)acrylate" is used herein to denote acrylate or methacrylate); cellulose derivatives, such as ethyl cellulose, cellulose acetate, cellulose propionate, cellulose acetate butyrate, and cellulose nitrate; polyalkylene polymers, such as polyethylene, polypropylene, polybutylene, polyisobutylene, and poly(4-methyl)pentene; fluorinated polymers such as perfluoroalkoxy resins, polytetrafluoroethylene, fluorinated ethylene-propylene copolymers, polyvinylidene fluoride, and polychlorotrifluoroethylene and copolymers thereof; chlorinated polymers, such as polydichlorostyrene, polyvinylidene chloride and polyvinylchloride; polysulfones; polyethersulfones; polyacrylonitrile; polyamides such as nylon, nylon 6,6, polycaprolactam, and polyamide 6 (PA6); polyvinylacetate; and polyether-amides. Also suitable are copolymers, such as styrene-acrylonitrile copolymer (SAN), preferably containing between 10 and 50 wt %, preferably between 20 and 40 wt %, acrylonitrile, styrene-ethylene copolymer; and poly(ethylene-1,4-cyclohexylenedimethylene terephthalate) (PETG). Additional polymeric materials include an acrylic rubber; isoprene (IR); isobutylene-isoprene (IIR); butadiene rubber (BR); butadiene-styrene-vinyl pyridine (PSBR); butyl rubber; chloroprene (CR); epichlorohydrin rubber; ethylene-propylene (EPM); ethylene-propylene-diene (EPDM); nitrile-butadiene (NBR); polyisoprene; silicon rubber; styrene-butadiene (SBR); and urethane rubber. Additional polymeric materials include block or graft copolymers. In one instance, the polymeric materials used to form the layers 12, 14 may constitute substantially immiscible thermoplastics. In addition, each individual layer 12, 14 may include blends of two or more of the above-described polymers or copolymers, preferably the components of the blend are substantially miscible with one another yet still maintaining substantial immiscibility between the layers 12, 14. The components comprising the layers 12, 14 can include organic or inorganic materials, including nanoparticulate materials, designed, for example, to modify the mechanical properties of the components, e.g., tensile strength. It will be appreciated that potentially any extrudable polymer can be used as the first polymer material (a) and the second polymer material (b) so long as upon coextrusion such polymer materials (a), (b) are substantially immiscible and form discrete layers or polymer regions. Such materials can have a substantially similar viscosity upon coextrusion.

In some embodiments, the polymers used to for the first and/or second polymer can be biodegradable and/or substantially biocompatible or cytocompatible (i.e., substantially non-cytotoxic). The use of biodegradable and substantially biocompatible or cytocompatible polymers allows a surface functionalized nanofiber scaffold to be formed that can be used in medical applications, e.g., tissue engineering or wound healing. Examples of that polymers that are substantially biocompatible or cytocompatible include polyesters, such as PCL, paired with PEO.

Referring to FIG. 1, the layers 12, 14 are co-extruded and multiplied in order to form the multilayered polymer composite film 10. In particular, a pair of dies 40, 50 is used to coextrude and multiply the layers 12, 14. Each layer 12, 14 initially extends in the y-direction of an x-y-z coordinate system. The y-direction defines the length of the layers 12, 14 and extends in the general direction of flow of material through the dies 40, 50. The x-direction extends transverse, e.g., perpendicular, to the y-direction and defines the width of the layers 12, 14. The z-direction extends transverse, e.g., perpendicular, to both the x-direction and the y-direction and defines the height or thickness of the layers 12, 14.

The layers 12, 14 are initially stacked in the z-direction and define an interface 20 therebetween that resides in the x-y plane. As the layers 12, 14 approach the first die 40 they are separated from one another along the z-axis to define a space 22 therebetween. The layers 12, 14 are then re-oriented as they pass through the first die 40. More specifically, the first die 40 varies the aspect ratio of each layer 12, 14 such that the layers 12, 14 extend longitudinally in the z-direction. The layers 12, 14 are also brought closer to one another until they engage or abut one another along an interface 24 that resides in the y-z plane.

The layers 12, 14 then enter the second die 50 where layer multiplication occurs. The second die 50 may constitute a single die or several dies which process the layers 12, 14 in succession (not shown). Each layer 12, 14 is multiplied in the second die 50 to produce a plurality of first layers 12 and a plurality of second layers 14 that alternate with one another to form the multilayered polymer composite film 10. Each pair of layers 12, 14 includes the interface 24 that resides in the y-z plane. The layers 12, 14 are connected to one another generally along the x-axis to form a series of discrete, alternating layers 12, 14 of polymer material (a), (b). Although three of each layer 12 and 14 are illustrated it will be appreciated that the multilayered polymer composite film 10 may include, for example, up to thousands of each layer 12, 14.

Figure 2:
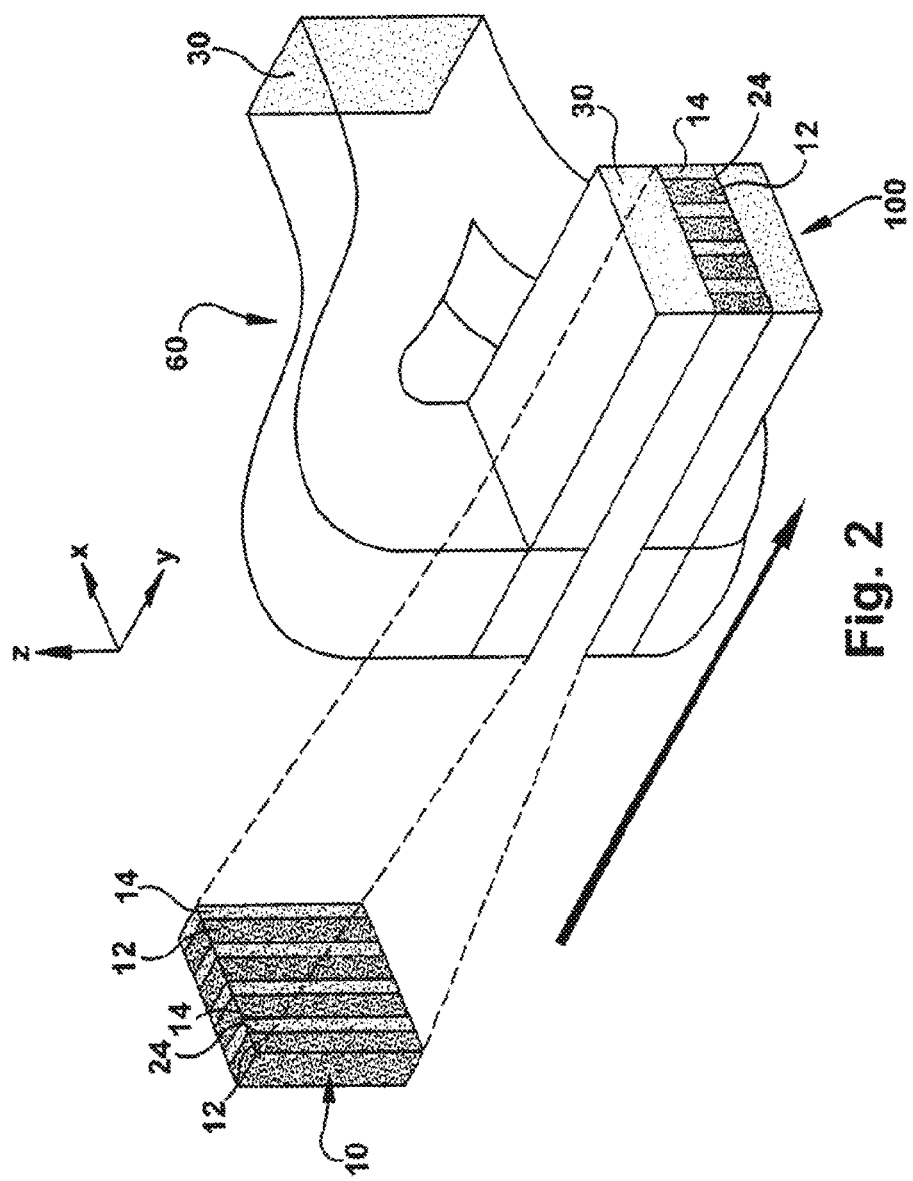
FIG. 2 is a schematic illustration of coextruding skin layers onto the composite film of FIG. 1 to form a composite stream.

Referring to FIG. 2, once the multilayered polymer composite film 10 is formed a detachable skin or surface layer 30 is applied to the top and bottom of the film 10 such that the film 10. In particular, the multilayered polymer composite film 10 enters a die 60 where the film 10 is sandwiched between two skin layers 30 along the z-axis to form a first composite stream 100. The skin layer 30 may be formed from the first polymer material (a), the second polymer material (b) or a third polymer material (c) different from the first and second polymer materials (a), (b). One or both of the skin layers 30 may, however, be omitted (not shown).

Figure 3:
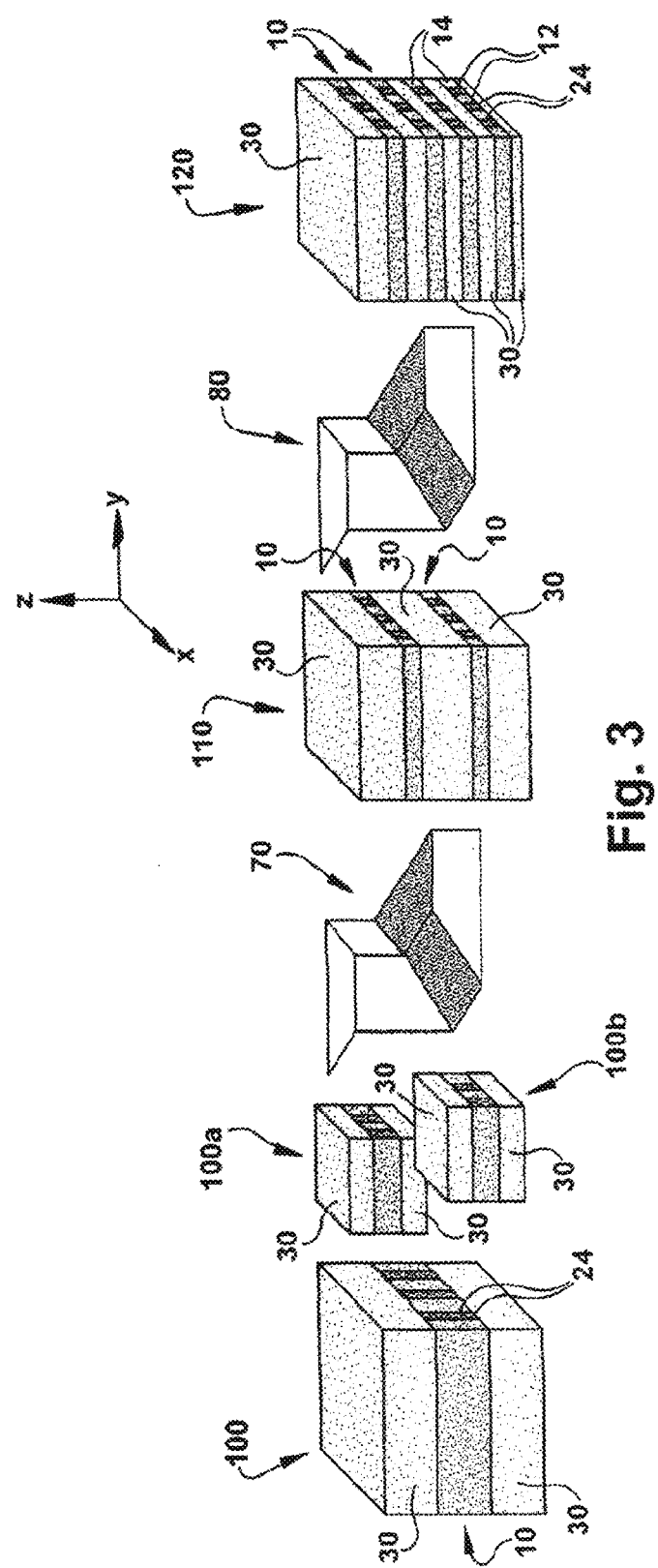
FIG. 3 is a schematic illustration of additional layer multiplying steps for the composite stream of FIG. 2.

Referring to FIG. 3, the first composite stream 100 is divided along the x-axis into a plurality of branch streams 100a, 100b and processed through a pair of multiplying dies 70, 80. In the die 70, the streams 100a, 100b are stacked in the z-direction, stretched in both the x-direction and the y-direction, and recombined to form a second composite stream 110 that includes a plurality of multilayered films 10 alternating with skin layers 30. Biaxial stretching of the branch streams 100a, 100b in the x-direction and y-direction may be symmetric or asymmetric.

The die 80 performs similar modifications to the second composite stream 110 that the die 70 performed on the branch streams 100a, 100b. In particular, in the die 80 the second composite stream 110 is divided along the x-axis, stacked along the z-axis, stretched in both the x-direction and the y-direction, and stacked in the z-direction to form a third composite stream 120. The third composite stream 120 shown in FIG. 3 includes four multilayered composite films 10 that alternate with five skin layers 30, although more or fewer of the films 10 and/or layers 30 may be present in the third composite stream 120. Regardless, the third composite stream 120 includes a plurality of layer interfaces 24 between the layers 12, 14.

By changing the volumetric flow rate of the polymer layers 12, 14 through the dies 70, 80, the thickness of both the polymer layers 12, 14 and each multilayered polymer film 10 in the z-direction can be precisely controlled. Additionally, by using detachable skin layers 30 and multiplying the composite streams 100, 110 within the dies 70, 80, the number and dimensions of the layers 12, 14, the multilayered polymer film 10, and the branch streams 100a, 100b in the x, y, and z-directions can be controlled.

Figure 4C:
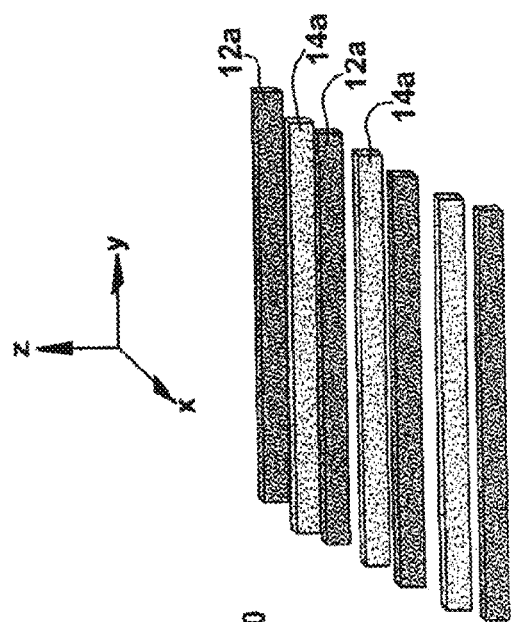
FIG. 4C is a schematic illustration of delaminating the composite stream of FIG. 2.
Figure 4B:
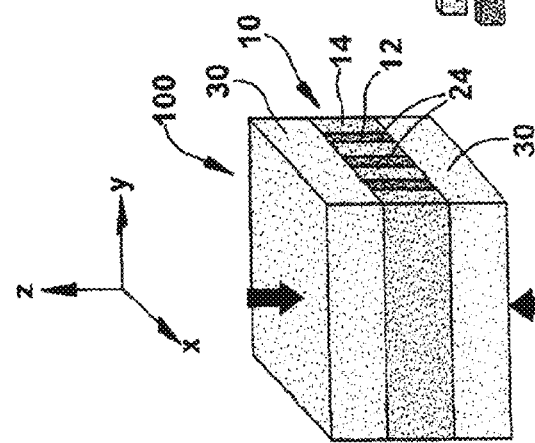
FIG. 4B is a schematic illustration of compressing the composite stream of FIG. 2.
Figure 4A:
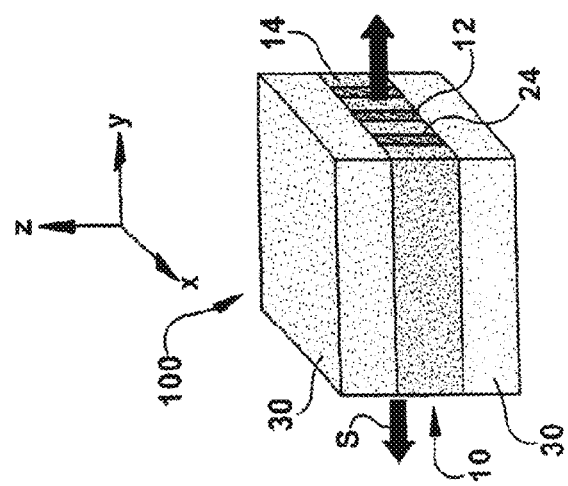
FIG. 4A is a schematic illustration of stretching the composite stream of FIG. 2.

Referring to FIGS. 4A and 4B, the first composite structure 100 may be mechanically processed by, for example, at least one of orientation (FIG. 4A), compression (FIG. 4B), and ball-mill grinding (not shown). As shown, the composite stream 100 is stretched in the y-direction as indicated generally by the arrow "S", although the composite stream 100 may alternatively be stretched in the x-direction (not shown). FIG. 4B illustrates the composite stream 100 being compressed in the z-direction as indicated generally by the arrow "C". The degree of stretching and/or compression will depend on the application in which the nanofibers and/or scaffold formed from the multilayered polymer film 10 is to be used. The ratio of y-directional stretching to z-direction compression may be inversely proportional or disproportional.

In one embodiment, the multilayer film can be uniaxially stretched in the y-direction or S-direction at a draw ratio of about 1 to about 10 to decrease the cross-sectional dimension of the fibers and increase the surface area of the nanofibers and scaffold so formed.

Referring to FIG. 4C, the first composite stream 100 can be further processed to cause the components 12, 14, 30 thereof to separate or delaminate from one another and form a plurality of fibers or fiber-like structures 12a, 14a from the layers 12, 14. The removed skin layers 30 are discarded. In one instance, the layers 12, 14, 30 are mechanically separated by high pressure water jets (not shown). In particular, two opposing ends of the composite stream 100 can be fixed and water jets with a nozzle pressure of no less than about 2000 psi can be applied to the composite stream 100 to separate the layers 12, 14, 30 completely, thereby forming the nano-fibers 12a, 14a. More specifically, applying high pressure water to the first composite stream 100 removes the interfaces 24 between the layers 12, 14, i.e., delaminates the multilayered polymer composite films 10, to form the fibers 12a and 14a. Although delamination of the first composite stream 100 is illustrated, it will be appreciated that the multilayered polymer composite film 10, the second composite stream 110 or the third composite stream 120 may likewise be delaminated via high pressure water or the like to form the fibers 12a, 14a.

Alternatively, the polymer material (a) or (b) of one of the layers 12, 14 is selected to be soluble in a particular solvent while the other polymer material (a) or (b) is selected to be insoluble in that solvent. Accordingly, immersing the composite stream 100 in the solvent separates the layers 12, 14 by wholly removing, e.g., dissolving, not only the interfaces 24 between the layers 12, 14 but removed the soluble layers 12 or 14 entirely. The insoluble layers 12 or 14 are therefore left behind following solvent immersion. The same solvent or a different solvent may be used to dissolve the skin layers 30, when present. The remaining soluble layers 12 or 14 form the fibers 12a or 14a. In one instance, the solvent can be water and in some instances no organic solvent is used.

Figure 5:
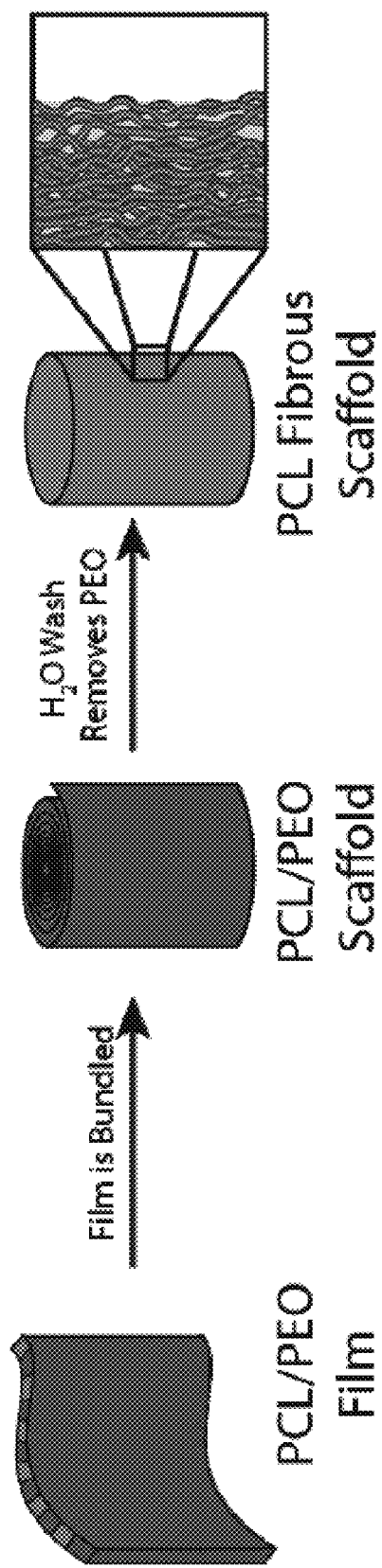
FIG. 5 is a schematic illustration of delaminating a composite stream to form a scaffold.

Optionally, as illustrated in FIG. 5, a multilayer composite stream that includes a polymer material soluble in a particular solvent and another polymer material insoluble in that solvent can be bundled or consolidated prior to solvent immersion. Immersing the bundled composite stream in the solvent separates the layers and forms a scaffold of the polymer nanofibers.

Whether the fibers 12a and/or 14a are formed by mechanically separating the layers 12 or 14 or dissolving one of the layers 12 or 14 with a solvent, the nanofibers 12a and/or 14a produced by the described coextrusion process have rectangular cross-sections rather than the conventional, round cross-sections formed by electrospinning. These rectangular or ribbon-like nanofibers 12a or 14a have a larger surface area-to-volume ratio than round fibers developed using spinning methods. Regardless of the method of separation enlisted, the nanofibers 12a and/or 14a can stretch, oscillate, and separate from each other at the interface 24. Furthermore, due to the aforementioned mechanical processing techniques of FIGS. 4A and 4B, the exact cross-sectional dimensions of the rectangular fibers 12a and/or 14a can be precisely controlled. For example, the rectangular fibers 12a and/or 14a can be made smaller and strengthened via mechanical processing.

Due to the construction of the first composite stream 100 and the fixed sizes of the dies 40-80, the composition of the vertical layers 12, 14 and surface layers 30 is proportional to the ratio of the height in the z-direction of a vertical layer 12, 14 section to that of a surface layer 30 section. Therefore, if the layer 12 (or 14) is selected to form the rectangular fibers 12a (or 14a), the thickness and height of the final fibers 12a (or 14a) can be adjusted by changing the ratio of the amount of the layers 12, 14 as well as the amount of surface layer 30. For example, increasing the percentage of the amount of the material (b) of the layers 14 relative to the amount of the material (a) of the layers 12 and/or increasing the amount of the material of the surface layers 30 results in smaller rectangular fibers 12a. Alternatively, one or more of the dies 40-80 may be altered to produce nanofibers 12, 12a, 14, 14a having a size and rectangular cross-section commensurate with the desired application. In one instance, one or more of the dies 40-80 could be modified to have a slit or square die construction to embed the fibers 12, 12a, 14, 14a within the surface layers 30.

The extrusion process can be tailored to produce vertically layered films 10 with designer layer/fiber thickness distributions. For example, the relative material compositions of the polymers (a), (b) of the layers 12, 14 can be varied with great flexibility to produce rectangular polymer fibers 12, 12a, 14, 14a with highly variable constructions, e.g., 50/50, 30/80, 80/30, etc. The rectangular polymer fibers 12, 12a, 14, 14a can be highly oriented and strengthened by post-extrusion orienting. Furthermore, a wide magnitude of layer 12, 14 thicknesses in the z-direction is achievable from a few microns down to tens of nanometers depending on the particular application.

The polymer nanofibers so formed can be consolidated to produce polymer nanofiber scaffolds. In one embodiment, as shown in FIG. 5, the nanofibers can be consolidated by bundling the composite stream prior to separation of the fibers or salvation of a polymer. In other embodiments, the nanofibers can be consolidated by compressing, weaving, and physically mixing the fibers.

The nanofiber scaffolds can have various densities and porosities depending on the fiber cross-section and the process used to consolidate the fibers. For example, the scaffolds can have a porosity of about 1% by volume to about 50% by volume, and a pore size of about 1 µm to about 100 µm. In some embodiments, each fiber can have a rectangular cross section of 10 nm (height)×10 nm (width) to about 10 µm×10 µm, with variations in between. The nanofibers can have surface area of at least about 1 cm$^2$/mg, at least about 10 cm$^2$/mg, at least about 20 cm$^2$/mg, at least about 40 cm$^2$/mg, at least about 50 cm$^2$/mg or more.

The nanofibers of the scaffold can be chemically modified (or surface modified) non-destructively after processing to append click reactive functional groups onto the nanofibers such that the click-reactive functional groups extend from portions or selected portions of the nanofiber.

In some embodiments, the click-reactive functions groups can be chemically bound to the nanofibers with diarylhydroxymethylene linkages that are formed by reaction of click-reactive functional group substituted diarylketones with polymer chains of the nanofibers. For example, modified diarylketones, such as benzophenones, which present click-reactive functional groups, such as alkynes, ketones, and alkoxyamines, can be attached to polymer chains of the nanofibers using photochemistry. In the presence of ultraviolet (UV) light, the diarylketones can generate radicals and undergo free radical insertion in the polymer backbone of the nanofibers.

For example, as shown below, photochemistry can used to chemically bind a click-reactive group substituted benzophenone to PCL of a nanofiber:

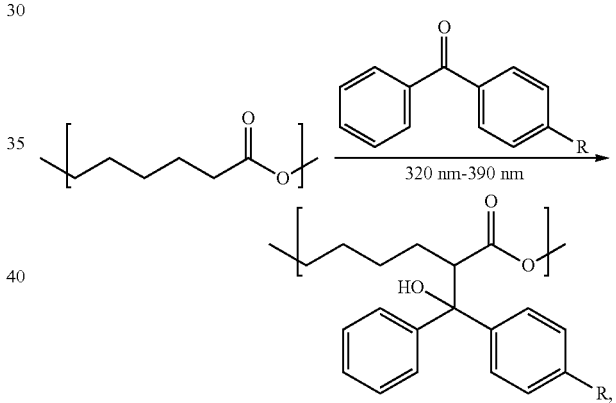

wherein R is a click-reactive group.

By click-reactive functional group, it is meant that the functional group has click reactivity and/or can undergo a click reaction with a complementary click reactive functional group or molecule. Examples of the types of reactions that are known to have click reactivity include cycloaddition reactions. These reactions represent highly specific reactant pairs that have a chemoselective nature, meaning that they mainly react with each other and not other functional groups. One example of a cycloaddition reaction is the Huisgen 1,3-dipolar cycloaddition of a dipolarophile with a 1,3 dipolar component that produce five membered (hetero) cycles. Examples of dipolarophiles are alkenes, alkynes, and molecules that possess related heteroatom functional groups, such as carbonyls and nitriles. Specifically, another example is the 2+3 cycloaddition of alkyl azides and acetylenes. Other cycloaddition reactions include Diels-Alder reactions of a conjugated diene and a dienophile (such as an alkyne or alkene).

Other examples of the types of reactions that are known to have click reactivity include a hydrosilation reaction of H—Si and simple non-activated vinyl compounds, urethane formation from alcohols and isocyanates, Menshutkin reactions of tertiary amines with alkyl iodides or alkyl trifluoromethanesulfonates, Michael additions, e.g., the very efficient maleimide-thiol reaction, atom transfer radical addition reactions between —SO$_2$Cl and an olefin, metathesis, Staudinger reaction of phosphines with alkyl azides, oxidative coupling of thiols, many of the procedures already used in dendrimer synthesis, especially in a convergent approach, which require high selectivity and rates, nucleophilic substitution, especially of small strained rings like epoxy and aziridine compounds, carbonyl chemistry like formation of ureas, and addition reactions to carbon-carbon double bonds like dihydroxylation. Therefore, the attached click-reactive functional group may be chosen, for example, from an alkyne group, acetylene group, an azido-group, a nitrile group, acetylenic group, amino group, or phosphino group. The click chemistry reaction may results in the addition of a functional group selected from amino, primary amino, hydroxyl, sulfonate, benzotriazole, bromide, chloride, chloroformate, trimethylsilane, phosphonium bromide or bio-responsive functional group.

In some embodiments, the click-reactive group can include at least one of an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, —CO$_2$N(COCH$_2$)$_2$, —CO$_2$N(COCH$_2$)$_2$, —CO$_2$H, —CHO, —CHOCH$_2$, —N=C=O, —SO$_2$CH=CH$_2$, —N(COCH$_2$)$_2$, —S—S—(C$_5$H$_4$N) and groups of the following structures:

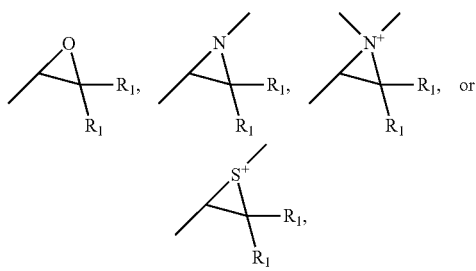

wherein R$_1$ is hydrogen or C$_1$ to C$_4$ alkyl.

The click-reactive functional group substituted diarylketones can be provided on the nanofibers or nanofiber scaffold by coating a solution of the click-reactive functional group substituted diarylketones onto the nanofibers, removing excess solvent, and irradiating the coated nanofibers or scaffold with UV light. In some embodiments, the solution of click-reactive functional group substituted diarylketones can be coated, e.g., spray coated, on the nanofibers of the scaffold such that the concentration of functional groups extending from at least one portion is at least about 0.1 nmol/cm$^2$. The amount, concentration, and/or spatial location of the click-reactive functional group substituted diarylketones provided on the nanofibers of the scaffold can be controlled such that different densities or concentrations of the click-reactive functional group substituted diarylketones are localized or patterned on different portions of the scaffold. In some embodiments, surface coverage of the nanofibers can be, for example, about 0.1 nmol/cm$^2$ to about 10 nmol/cm$^2$.

In some embodiments, one or more similar or different click-reactive functional groups can be spatially arranged on the nanofibers such that different portions of the nanofibers have different concentrations of the same or different click-reactive functional groups. For example, a plurality of first functional groups can be arranged on the nanofibers in a first concentration gradient and/or a plurality of second functional groups can be arranged on the nanofibers in a second concentration gradient.

In some embodiments, gradient concentrations of the click-reactive functional groups can be provided on the fibers or scaffold by spraying or coating different portions of the nanofibers and/or scaffold different with different types or concentrations of click-reactive functional group substituted diarylketones. In other embodiments, gradient concentrations of the click-reactive functional groups can be provided on the fibers or scaffold using a photomasking strategy to pattern or modulate the concentration of click-reactive functional group substituted diarylketones deposited on select portions of the fibers. For example, photomask having defined regions of transparency ranging from completely UV transparent to opaque can be used to pattern or define the surface location and concentration of the click-reactive functional group substituted diarylketones bound to the nanofibers of the scaffold.

The gradients can be comprised of different click-reactive functional group substituted diarylketones bound to the nanofibers of the scaffold, such as benzophenones having different click-reactive functional groups (e.g., alkyne, aminoxy, etc.). As discussed below, for example, the different click-reactive functional group substituted diarylketones bound to the nanofibers can be provided in a particular pattern or concentration on the nanofiber scaffold to allow the attachment of different agents to the nanofiber scaffold.

For example, as shown in FIG. 6, a first solution of ketone click-reactive group substituted diarylketones can be provided on a PCL nanofiber and irradiated with UV light through a photomask with defined transparency regions to provide the PCL nanofiber with a defined concentration gradient of the ketone click-reactive group substituted diarylketones. A second solution of alkyne click-reactive group substituted diarylketones can then be provided on the PCL nanofiber and irradiated with UV light through a photomask with defined transparency regions to provide the PCL nanofiber with a defined concentration gradient of the alkyne click-reactive group substituted diarylketones.

The click-reactive functional groups bound to the polymer chains of the nanofibers using diarylketone chemistry can participate in click-reactions, such as cycloaddition or Michael addition reactions, with complementary click-reactive groups of specific binding pairs. The complementary click-reactive groups of specific binding pairs can be conjugated to one more agents such that the agents can be readily attached to the surface functionalized nanofiber using click-reactive chemistry. Examples of click-reactions used to conjugate agents include the following:

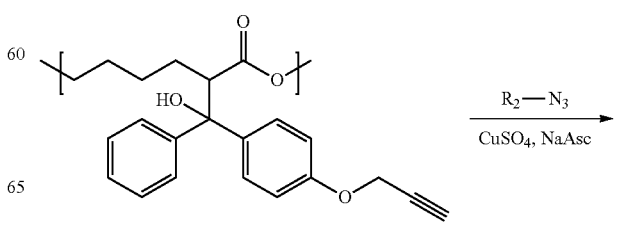

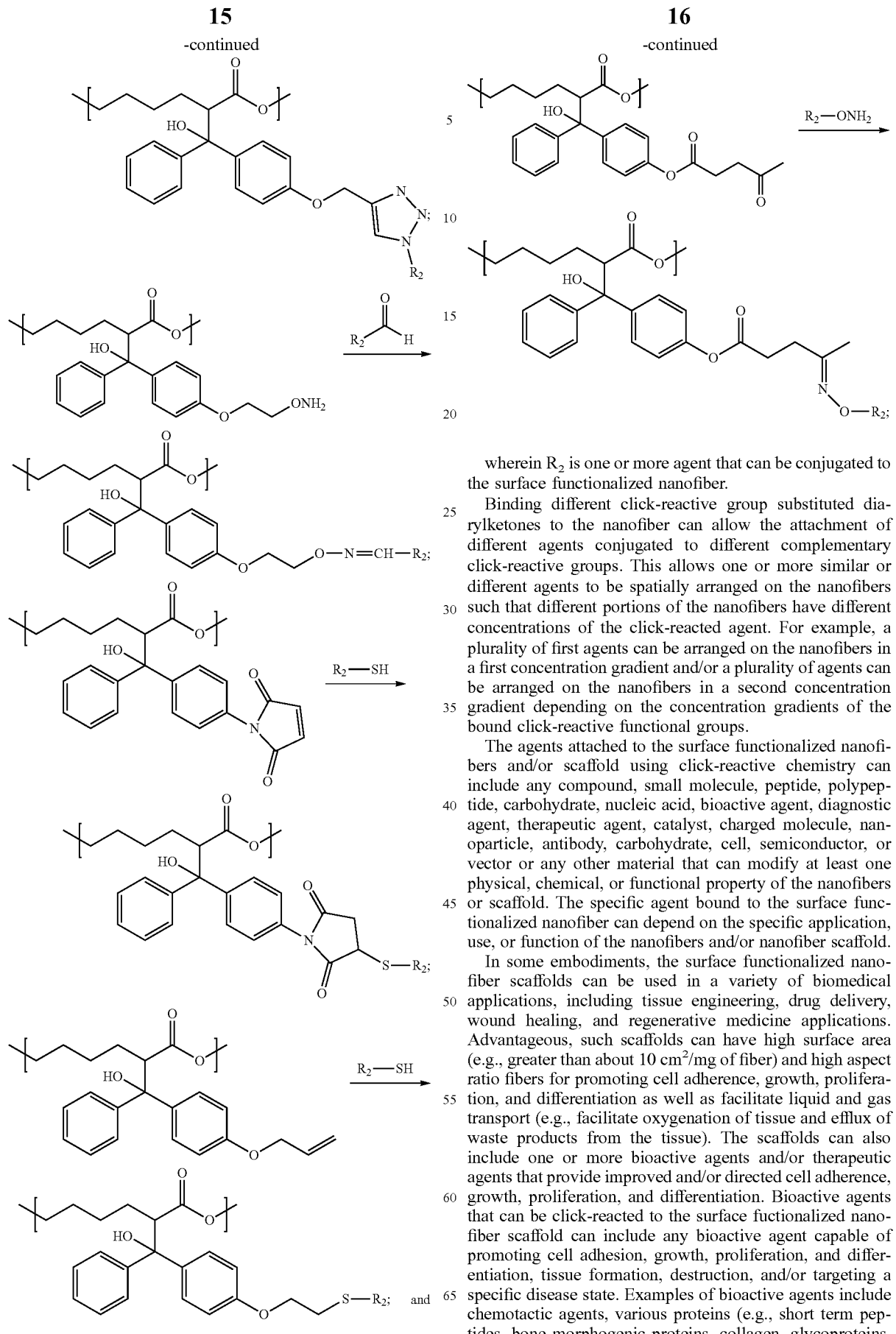

wherein $R_2$ is one or more agent that can be conjugated to the surface functionalized nanofiber.

Binding different click-reactive group substituted diarylketones to the nanofiber can allow the attachment of different agents conjugated to different complementary click-reactive groups. This allows one or more similar or different agents to be spatially arranged on the nanofibers such that different portions of the nanofibers have different concentrations of the click-reacted agent. For example, a plurality of first agents can be arranged on the nanofibers in a first concentration gradient and/or a plurality of agents can be arranged on the nanofibers in a second concentration gradient depending on the concentration gradients of the bound click-reactive functional groups.

The agents attached to the surface functionalized nanofibers and/or scaffold using click-reactive chemistry can include any compound, small molecule, peptide, polypeptide, carbohydrate, nucleic acid, bioactive agent, diagnostic agent, therapeutic agent, catalyst, charged molecule, nanoparticle, antibody, carbohydrate, cell, semiconductor, or vector or any other material that can modify at least one physical, chemical, or functional property of the nanofibers or scaffold. The specific agent bound to the surface functionalized nanofiber can depend on the specific application, use, or function of the nanofibers and/or nanofiber scaffold.

In some embodiments, the surface functionalized nanofiber scaffolds can be used in a variety of biomedical applications, including tissue engineering, drug delivery, wound healing, and regenerative medicine applications. Advantageous, such scaffolds can have high surface area (e.g., greater than about 10 cm$^2$/mg of fiber) and high aspect ratio fibers for promoting cell adherence, growth, proliferation, and differentiation as well as facilitate liquid and gas transport (e.g., facilitate oxygenation of tissue and efflux of waste products from the tissue). The scaffolds can also include one or more bioactive agents and/or therapeutic agents that provide improved and/or directed cell adherence, growth, proliferation, and differentiation. Bioactive agents that can be click-reacted to the surface fuctionalized nanofiber scaffold can include any bioactive agent capable of promoting cell adhesion, growth, proliferation, and differentiation, tissue formation, destruction, and/or targeting a specific disease state. Examples of bioactive agents include chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF), HGF, VEGF, fibroblast growth factors (e.g., bFGF), PDGF, insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparin sulfate, polynucleotides, DNA fragments, DNA plasmids, MMPs, TIMPs, interfering RNA molecules, such as siRNAs, DNA encoding for an shRNA of interest, oligonucleotides, proteoglycans, glycoproteins, and glycosaminoglycans.

In one example, the surface functionalized nanofiber scaffold can be used as a substrate for a wound dressing. The wound dressing can have a length, a width, and a thickness that may be varied depending upon the particular application. For example, the wound healing dressing can have a sleeve-like or cylindrical configuration as well as a rectangular or square-shaped configuration. In one example, the wound healing dressing can have a thickness of about 1 cm to about 10 cm or greater, a length of about 2 cm to about 30 cm or greater, and a width of about 2 cm to about 30 cm or greater.

The wound dressing can include a plurality of peptides and proteins click-reacted to the surface of the scaffold and that can promote cell growth, attachment, and migration. An example of a protein that can be click-reacted to the surface functionalized nanofiber scaffold is epidermal growth factor (EGF). EGF is known to enhance treatment of chronic wounds. Examples of peptides that can be click-reacted to the surface functionalized nanofiber scaffold include an RGD sequence derived from fibronectin, which is known to promote cellular adhesion, and an IKVAV peptide, which can be used to induce neural growth and migration.

The EGF, RGD, and/or IKVAV can be provided or patterned in multiple gradients on the nanofiber scaffold to promote cell adherence, growth, migration. The gradients can run in the same or opposite directions. For example, the wound healing dressing formed from the surface functionalized nanofiber scaffold can be can include gradients of the EGG, RGD, and/or IKVAV that facilitate cell growth, attachment, migration when the wound healing dressing is applied to tissue being treated in a subject in need thereof. In some embodiments a gradient of IKVAV can be provided on the nanofibers and/or scaffold to promote neural cell growth and migration.

It will be appreciated that the surface functionalized nanofibers and/or scaffold can be potentially used in any application where it is desirable to modify at least one physical, chemical, or functional property of the nanofibers and/or scaffold. For example, the surface functionalized nanofibers can be used to form surface functionalized membrane supports in which various chemicals, catalysts, or other agents are patterned on the surface of the membrane. Such membranes can be useful in different processes, such as filtration, desalination, water purification, chemical processing or synthesis, nanoelectronics, non-woven fabrics, drug delivery, drug discovery, information storage, mechanical actuation, microarrays, and bioconjugation.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In this example, we used a melt co-extrusion in conjunction with a modular chemistry to yield polyester nanofibers with pendant surface functionality. The processing method makes use of the co-extrusion of PCL and PEO through a series of dye multipliers to form a nanofibrous PCL matrix within a PEO tape. PCL and PEO are melt-pumped and layered on top of one another in the extrusion line (FIG. 7). From here a vertical multiplier is used to rearrange the extrudate to yield a vertical layer structure (Step A). This is then followed by a series of vertical multipliers that cut the flow horizontally and expands the flow fields in the vertical direction to align in parallel. This process is repeated eight times to yield a vertically aligned, layered flow comprised of alternating PCL (512 layers) and PEO (512 layers) with 1024 total layers (Step B). The tape is then combined with two surface layers of PEO on the top and bottom (Step C) and is split vertically with one side stacked on top of the other (2×) to yield a PCL nanomatrix embedded in a PEO tape. This procedure is repeated one additional time, and an extrudate containing 512 PCL nanodomains embedded in a PEO matrix is obtained (Step D). The PEO in the tape can be removed by dissolution in a water bath or by using a high pressure water jet to produce a PCL nanofiber matrix. A scanning electron micrograph of the PCL fibers after the dissolving procedure shows fibers displaying cross-sectional dimensions of approximately 400-1000 nm by 2-5 μm (FIG. 7). After removal of the PEO matrix, <1% of PEO remained as determined by NMR and DSC (Supporting Information), yielding a scalable PCL nanofiber mat.

Once the fibers were extruded and separated, we sought to further modify the fiber mats to add pendant functionality. A number of papers have focused on the aminolysis of polyester fibers, in which a bifunctional amine is used to introduce a reactive group for further derivatization. In the case of the extruded nanofibers, prepared as described, the aminolysis reaction using either propargylamine or hexamethylene diamine showed minimal surface modification. This could be due to the small fraction of PEO remaining on the exterior of the fibers, occluding access to the aminolysis pathway. Rather than pursuing forcing reaction condition, an alternate route was chosen so as not to degrade the polymer chains within the fibers. As such, a photochemical radical reaction was employed to perform a C—H bond insertion into the backbone of the PCL polymer chains (FIG. 8). Benzophenone is commonly used to perform photochemical C—H insertions and has been previously used to modify PCL surfaces. Propargyl benzophenone was prepared in high-yield by reacting 4-hydroxyl benzophenone with propargyl bromide under basic conditions. The propargylbenzophenone derivative was solvent cast onto the PCL fibers, irradiated via UV (33.2 mW/cm², 30 min on each side, 320-500 nm) and washed with methanol to yield alkyne-decorated PCL nanofibers. The propargyl group could then be used in the CuAAC reaction to decorate the fiber with any azide containing molecule.

To probe the CuAAC chemistry, we first modified the PCL-alkyne fibers with an azide containing fluorescent dye, AzideFluor488 ($AF_{488}$). The fibers were modified using aqueous conditions optimized for the ligand-accelerated CuAAC reaction, using tris(3-hydroxypropyltriazolylmethyl)amine (THPTA) as the ligand to accelerate the reaction. After the CuAAC reaction, upon visual inspection, the fibers were noticeably red after using standard reaction conditions. While in the absence of copper, there was no visible change that could be attributed to a hydrophobic physical adsorption of the dye onto the fiber. To further probe the surface coverage of the PCL fibers, confocal fluorescent microscopy was used to qualitatively and quantitatively evaluate the surface coverage of the fibers. As seen in the case with no copper catalyst, negligible fluorescence is visible in the micrograph (FIG. 9A), indicating that little dye non-specifically adsorbs to the fiber bundle. However, in the presence of copper a significant fluorescent intensity appears in the micrograph indicating that the chemistry is specific, rather than simple adsorption. When fluorescence intensity was quantified, modified fibers showed approximately two-orders of magnitude higher fluorescent intensity relative to control fibers (FIG. 9C).

In order to effect biological outcomes, it is necessary that a significant surface coverage of the fibers be attained. To quantify this, we determined both the total dye loading of the fibers in conjunction with surface area measurements. Brunauer Emmett Teller (BET) measurements were used to determine the surface area of the extruded fibers, and UV-visible measurements were used to quantify dye loading. The BET technique relies on the surface adsorption of gas molecules; the total mass of the gas adsorbed allows one to calculate the area of the surface. BET measurements were carried out, showing the surface are of the fibers to be 41.2 $cm^2$/mg of fiber. Of note, electrospun fibers of similar cross sectional dimensions showed an approximately 20-fold lower surface area. This can be attributed to the rectangular geometry of the extruded fiber as compared to the electrospun cylindrical fiber. Once the surface area was determined, we labeled the fibers with $AF_{488}$, as described. The fibers were dissolved in DCM and the absorbance at 501 nm was compared to a standard curve of $AF_{488}$ to determine total surface loading of the fibers. The PCL-AF488 fibers were decorated with approximately 15.5 nmol/mg of fiber, resulting in a surface coverage of 0.38 nmol/$cm^2$. The surface coverage of the fibers is of particular importance as a scaffold for regenerative medicine. A common peptide, and one we employed here, is the RGD motif. RGD sequences bind to integrin receptors, and when immobilized on a surface, can lead to cell adhesion and spreading, a key feature for tissue engineering scaffolds. Previous work showed that low pM/$cm^2$ surface coverages of RGD peptides on polymeric surfaces were sufficient to promote cell adhesion. Our concentrations are three-orders of magnitude higher than those necessary for adhesion, representing a viable scaffold to present biochemical cues and for cell-seeding.

Figure 10A:
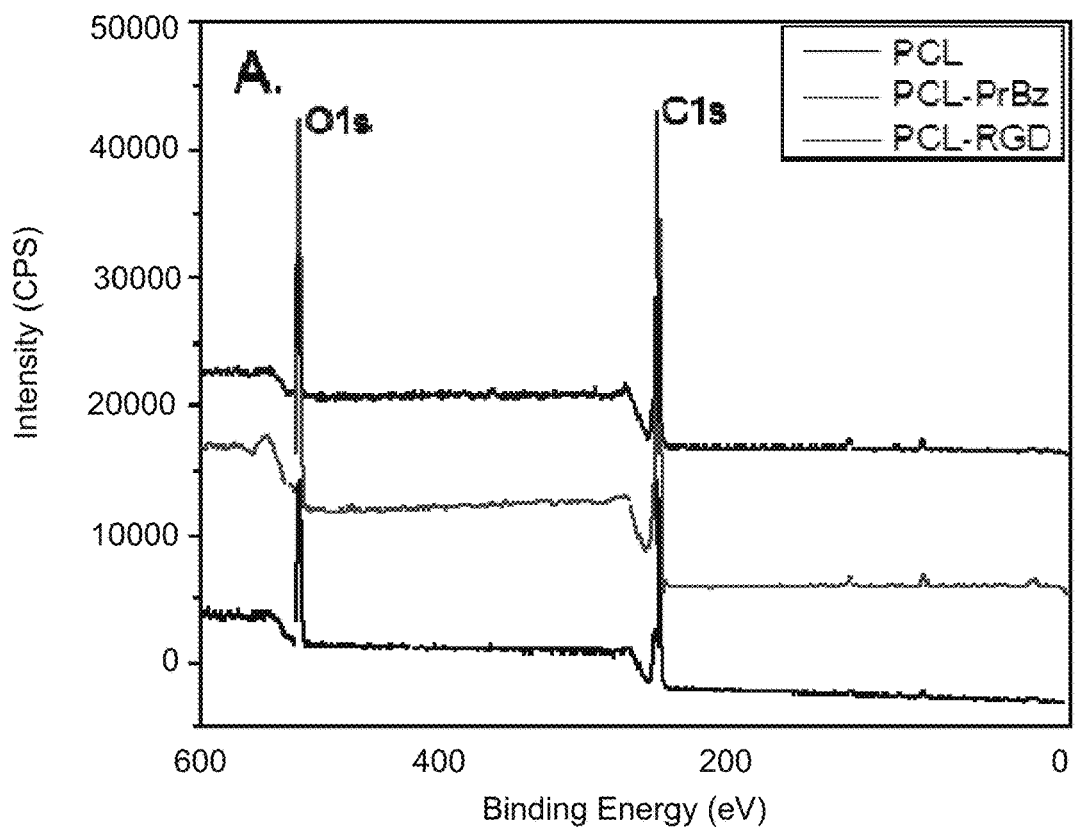
FIGS. 10(A-F) illustrate: A) Full XPS spectrum of PCL, PCL-PrBz, and PCL-RGD. B) $N_{1s}$ XPS spectrum of PCL nanofibers and PCL-RGD fibers, C) Confocal fluorescent microscopy image of NIH 3T3 cells after 72 hours of growth on PCL-RGD scaffold. 10× objective. D) Confocal fluorescent microscopy image of NIH 3T3 cells after 72 hours of growth on PCL-RGD scaffold. 40× objective. E) Confocal fluorescent microscopy image of NIH 3T3 cells after 72 hours of growth on control PCL scaffold. 10× objective. F) Confocal fluorescent microscopy image of NIH 3T3 cells after 72 hours of growth on control PCL scaffold. 40× objective. Blue indicates DAPI stain and green indicates actin green stain in confocal micrographs.
Figure 10B:
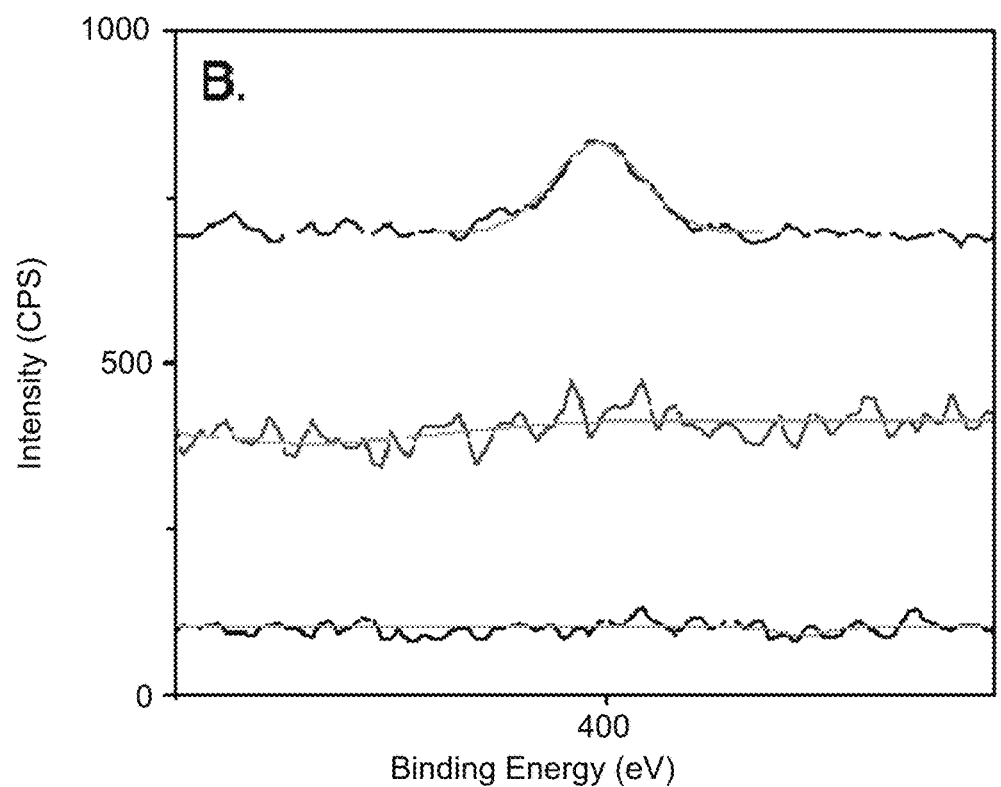

Finally, we sought to adhere an RGD peptide to promote cellular adhesion onto the PCL fiber scaffold. We first synthesized an RGD peptide with an N-terminal azide group ($N_3$-RGD), for attachment to the propargyl PCL fiber. The RGD peptide motif was chosen for its ability to promote adhesion through the interaction with integrin cell surface receptors, as is known to occur with NIH 3T3 fibroblasts, a common model for cell-seeding in regenerative medicine. The same scheme of photochemical attachment of propargyl-benzophenone followed by CuAAC reaction was followed to introduce the RGD-azide onto the surface of the PCL fibers. The attachment of the azido-peptide was confirmed via X-ray photoelectron spectroscopy (XPS), where the modified fiber showed a significant nitrogen peak ($N_{1s}$) as would be expected for peptide modified fibers, while no nitrogen peak was observed upon analysis of the PCL or PCL-benzophenone (FIG. 10B). XPS surface analysis indicated an approximate surface coverage of 2% by mass, consistent with our results using the fluorescent azide.

PCL-RGD nanofibers were used as a cell seeding scaffold that would be able to promote adhesion, growth, and proliferation of NIH 3T3 fibroblasts. Both PCL and PCL-RGD fibers were immobilized on a glass slide and NIH 3T3 cells were deposited onto the fiber. Following 72 hours of incubation, cells were fixed, permeabilized, and stained using actin green and DAPI. The slides were visualized via fluorescent confocal microscopy (FIG. 10). After 72 hours, a much greater portion of the cells adhered to the fibers, as visualized by confocal microscopy. Additionally, the RGD-immobilized fibers provided enhanced cell spreading, as viusualized by the actin filaments within the cells. In FIGS. 10C and 9D, at 72 hours post-seeding, the cells have become elongated along the axis of the fiber and their proliferation was enhanced by visual inspection of confocal micrographs. The unmodified fibers showed very little adhesion and proliferation after 72 hours. To quantify proliferation of the cells on the fiber scaffold, a cell viability assay was used (i.e., MTT). After 72 hours of incubation, the fibers were removed from the slides and immersed in MTT containing media. The PCL-RGD fibers showed an approximate increase of 60%, relative to the PCL fibers alone after 72 hours of incubation. These results indicate that the PCL-RGD fibers maintained the biological activity of the peptide in sufficient concentrations to promote adhesion, elongation, and proliferation.

This example shows the chemical modification of a continuously processed nanofibrous biomaterial comprised solely from commodity polymers. The processing technique is solvent free, scalable, uses FDA-friendly polymers and allows for the simple tuning of cross-sectional dimensions of the fiber. To convert this scaffold into a biological material, we utilized photochemistry to introduce an alkyne on to the surface of the fibers. This functional group allows for the modular synthesis of a host of chemically derivatized fibers by employing the CuAAC reaction. A densely covered surface was obtained using this technique, and more importantly the biological activity of the RGD peptide remained intact promoting cellular adhesion and spreading.

Example 2

In this Example, we show the incorporation of a gradient of covalently immobilized IKVAV peptides on coextruded PCL fibers to induce neural differentiation and alignment. Coextruded fibers were chosen due to their extensional strength, while maintaining lateral flexibility, in an effort to mimic a spinal cord replacement. Additionally, extruded fibers can remain aligned, providing for an additional topographical cue to promote directed elongation of neural cells. Photochemistry is used as a versatile tool to manipulate surface gradients, using a simple photomask with aligned PCL fibers. After attaching IKVAV gradients, we investigate neural cell growth in response to the gradient. In our system, both gradient modification and fiber alignment dictate neural differentiation and cellular alignment.

Materials

N, N-dimethylformamide (DMF) (99%), dimethyl sulfoxide (DMSO), methanol (99.8%), Azide-fluor 488 (HPLC), 5-bromovaleric acid, sodium azide, trifluoroacetic acid (TFA) were purchased from Sigma Aldrich. Propargyl benzophenone was prepared as previously reported. Tris(3-hydroxypropyltriazolylmethyl)amine (THPTA) was a generous gift from the Finn lab. PC-12 adherent cells were purchased from ATCC. Nerve Growth Factor 7S was purchased from Life Technologies. 4', 6-diamidino-2-phenylindole (DAPI) was purchased from EMD Biosciences, Inc. Anti-Neuron-specific β-III Tubulin-NL557 was purchased from R&D Systems Inc.

Instrumentation

Multilayer co-extrusion was performed using two-component coextrusion system with 12 multipliers. ATR-FTIR Imaging was conducted on a Digilab FTS 7000 spectrometer, a UMA 600 microscope, and a 32×32 MCT IR Imaging focal plane array (MCT-FPA) image detector with an average spatial area of 176 μm×176 μm in the reflectance mode. Surface analysis of materials was investigated on a PHI Versaprobe 5000 Scanning X-Ray Photoelectron Spectrometer (XPS) with an Al Kα X-ray source (1486.6 eV photons). Scanning electron microscopy (SEM) was performed using a JEOL SEM under an emission voltage of 20 kV. A high-intensity UV lamp (Bluepoint 4 Ecocure from Honle UV America Inc.) was used for surface modification of the PCL fibers with propargyl benzophenone (Pr-Bz). The molecular weight of the synthesized azido-peptide was measured on a Bruker AUTOFLEX III MALDI-TOF/TOF mass spectrometer using α-Cyano-4-hydroxycinnamic acid (CHCA) as a matrix. Fluorescent images were taken via laser scanning fluorescence confocal microscopy using a Leica TCS SPE Confocal Microscope. Water contact angle (WCA) measurements were tested on a CAM 200 optical contact angle meter (KSV Instruments Ltd). Fluorescent gradient images were collected on a Maestro imaging system from PerkinElmer.

Coextrusion of PCL Fibers

A multilayered film was extruded by a multiplication coextrusion process to fabricate polymeric fibers. PCL (CAPA 6800 pellets, MW=80 kg/mol) was coextruded with poly(ethylene oxide) (PEO) to produce PCL fibers. In order to match the rheology of PCL and PEO melts during the extrusion, two grades of PEO (Dow POLYOX N80 (MW=200 kg/mol) and POLYOX N10 (MW=100 kg/mol)) with a weight ratio of 30:70 were pre-blended using a Haake Rheodrive 5000 twin screw extruder. The viscosities of the obtained PEO blend and PCL melt match at the extrusion temperature, 200° C. Ten vertical multipliers and two horizontal multipliers were used throughout the extrusion line to generate a 256×4 matrix architecture that contains 128×4 PCL domains embedded in PEO. The chill roll speed was 40 rpm and the dimensions of the exit die are 0.5"×0.02". PEO was removed by stirring in water at room temperature for 24 hours, to yield PCL fiber bundles. The PCL fibers were washed with methanol 3 times and vacuum dried overnight.

Figure 11:
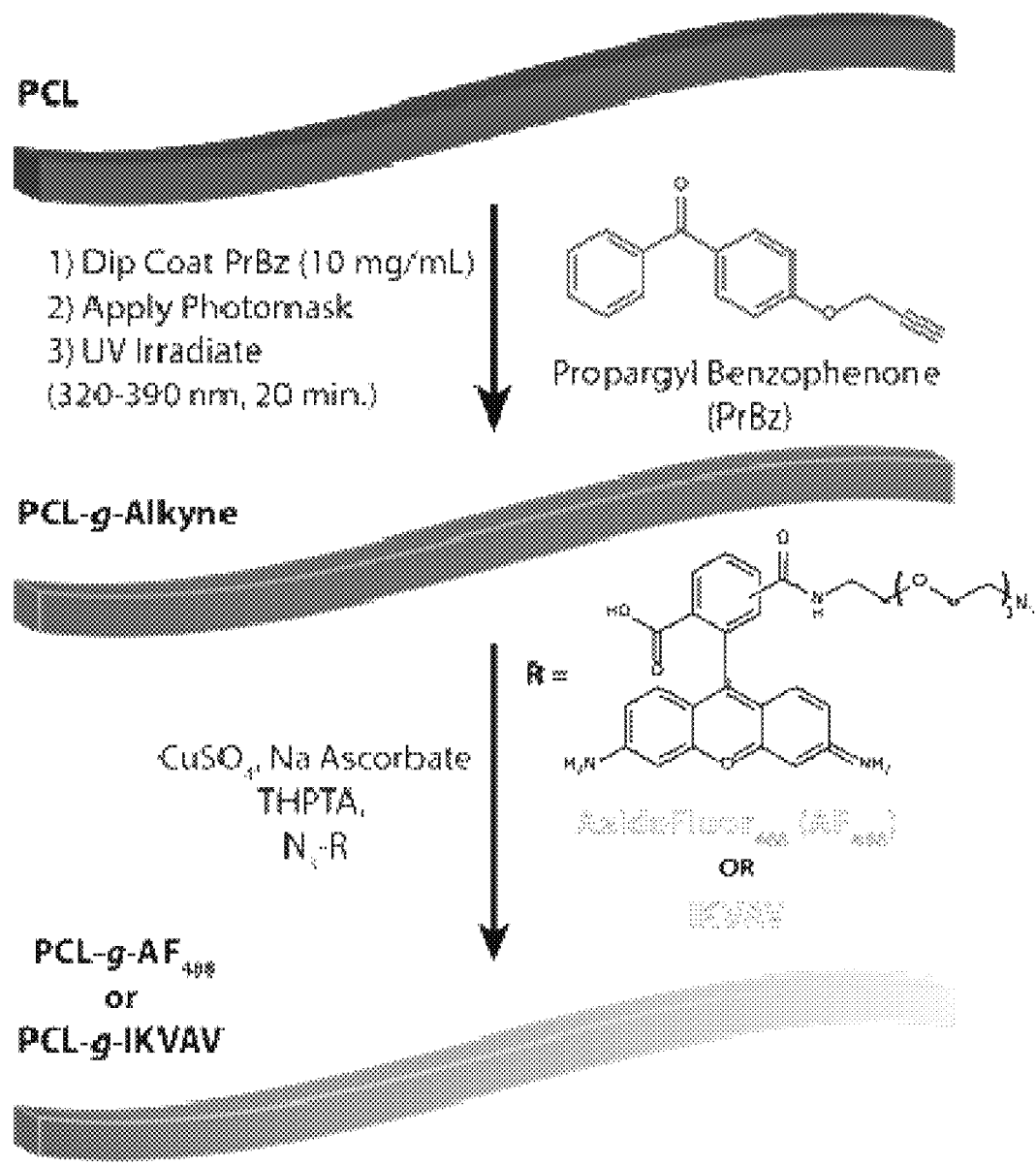
FIG. 11 illustrates a schematic of a synthesis scheme to generate a PCL fiber gradient.

Photochemistry 10 mm×30 mm linear gradient images were printed on transparency films (3M PP2410/100) with a commercialized inkjet printer (Epson WF 3540) from transparent to black. To evaluate the gradient photomask, three non-gradient photomasks were produced, corresponding to 3 points (black, 50% black and transparent: 0, 1.5 and 3 cm on the gradient photomask) on the gradient photomask to determine surface immobilization at each point on the fiber (FIG. 11).

Each fiber bundle (3 cm, derived from a single tape) was soaked in a Pr-Bz solution for 5 mins (10 mg/mL in methanol) and was air-dried at room temperature. Samples were placed on a 25 cm×75 cm slide glass and covered with the gradient photomask. The distance between the sample and UV source is 11.5 cm and a 320-390 nm filter was used. The UV intensity varied linearly from 2.7 to 28.6 mW/cm$^2$ from black to transparent and the center was 14.6 mW/cm$^2$. The unmasked UV source was 33.5 mW/cm$^2$. Samples were irradiated for 20 mins. After irradiation, samples were washed in methanol overnight to remove excess Pr-Bz, and solvent was evaporated under reduced pressure overnight. The process of photochemistry for non-gradients (PCL-ng-IKVAV) was repeated as described above without the use of a photomask.

Click Chemistry 3 cm of PCL fiber bundles were immersed in a pre-mixed aqueous solution of Azide Fluor 488 ($AF_{488}$) (0.8 mL, 3 mM) or azido-IKVAV (1.5 mL, 1.5 mM), $CuSO_4$ (10 μL, 50 μM) and THPTA (50 μL, 50 μM). A fresh solution of sodium ascorbate (100 μL, 100 mM) and 500 μL of DI water were added and incubated for 2 hours at room temperature. Gradient modified $AF_{488}$ or IKVAV (PCL-g-$AF_{488}$ or PCL-g-IKVAV) fibers were washed with dimethyl sulfoxide (DMSO) or water, respectively, overnight to remove unreacted dye or peptide. The gradient conjugation of $AF_{488}$ with PCL-Alkyne fibers was confirmed by Maestro fluorescence imaging (green excitation filter used with exposure time 100 ms). Quantification of surface AF488 dye was determined by dissolution of the fibers in DCM and quantification by UV-Vis absorbance at 501 nm (FIG. 12). This value was compared to the BET surface area of the fibers to determine surface coverage density (FIG. 13). PCL-g-IKVAV fibers were scanned at 3 spots using ATR-FTIR collecting from 600 to 4000 cm$^{-1}$ with 128 scans at the resolution 4 cm$^{-1}$. Spatial distribution of absorbance at 1628 cm$^{-1}$ was taken using FT-IR Imaging. Atomic chemical composition of PCL-g-IKVAV fibers was analyzed by XPS.

Wettability Test

Measurements were carried out at room temperature with high purity 18.2 MΩ DI water. A single liquid droplet was suspended at the edge of a syringe needle (Matrix Technologies micro-Electrapette 25) and placed on the measured surface. Water droplet images were taken on four different spots across the PCL-g-IKVAV fibers for each sample. The contact angles were measured as right and left angle of the water drop on the surface of the sample and reported as mean angles.

Cell Culture

PC-12 adherent cells (ATCC CRL-1721.1™) were purchased from ATCC and cells were cultured in F-12K Medium containing 15% heat inactivated horse serum, 2.5% fetal bovine serum (FBS), and 1% penicillin. Cells were incubated in 75 cm$^2$ cell culture flasks at 37° C., in a 95% air and 5% $CO_2$ environment. At 80-90% confluency, the cells were detached with PBS/EDTA for 10 minutes at 37° C. The detached cells were collected by centrifugation at 800 g for 5 minutes. $14.5×10^4$ cells were placed on each samples (PCL, PCL-ng-IKVAV and PCL-g-IKVAV) and cultured in the same media with the addition of 50 ng/mL of NGF at 37° C., 5% $CO_2$ in a humid environment for 5 days. The cell culture medium was refreshed every 2 days.

Immunocytochemical Staining

After 5 days of incubation, all samples were washed with DPBS 3 times and cells were fixed with 4% paraformaldehyde in DPBS for 15 minutes at room temperature. After fixing cells, the samples were washed 3 times with DPBS. Non-specific binding sites were blocked with 10% normal donkey serum, 0.1% Triton® X-100, and 1% BSA in DPBS for 30 minutes at room temperature. Sequentially, cells were incubated with Anti-Neuron-specific β-III Tubulin NL557-conjugated antibody (1:10 dilution) in blocking buffer for 3 hours at room temperature. After 3 hours, cells were washed and nuclei were stained with DAPI (100 μL, 5 μg/ml in PBS) to stain nuclei for 10 minutes and washed 3 times with DPBS.

Synthesis of IKVAV Peptide

The following is a representative coupling cycle for one amino acid monomer—synthesis was carried out in a Torviq 25 mL filtered syringe, specifically designed for peptide synthesis. Peptide synthesis started from 0.5 g of Rink Amide MBHA resin (0.52 mmol/gram) and this resin was pre-swelled in 15 mL of DMF for 10 minutes. The solvent is expelled through the syringe and a solution of 20% 4-methyl piperidine in DMF is added to the resin (10 mL), this is carried out twice for 5 minutes and 20 minutes, respectively. A Kaiser test was performed to confirm Fmoc deprotection. After a positive Kaiser test, the amino acid (0.78 mmol, 3 equiv), HCTU (323 mg, 3 equiv) and DIPEA (272 μL, 6 equiv) were dissolved in a minimal amount of DMF. This solution was added to the resin at room temperature on a rotary shaker and allowed to react for 1 hour. Following the coupling, the resin was again washed with DMF and DCM for 5 mins, 3 times each, and a qualitative Kaiser test was performed to ensure coupling. This synthetic process was repeated until the full peptide sequence was completed. After synthesis of the full peptide (IKVAV), the N-terminus of the peptide was conjugated with 5-Bromovaleric acid—as described above. After washing 3 times with DMF (10 mL) and DCM (10 mL), sodium azide (85 mmol, 5 equiv) was added in DMF and allowed to react overnight. Subsequently, the resin was washed with water to remove excess sodium azide and the resin was dried completely in a lyophilizer. To cleave the peptide, a solution of TFA/H$_2$O (95/5, v/v) (10 mL) was incubated with the resin for 3 hours at room temperature and the resin was removed by filtration. The cleaved peptide solution was precipitated in cold ether, centrifuged (10,000 rpm for 10 minutes at 4° C.), and decanted to yield a white pellet. The final crude peptide was dried under vacuum to yield a white powder. The crude IKVAV peptides were purified by reverse phase-HPLC (LC-20AD pump, UV-VIS detector SPD-20A, Shimadzu HPLC System). Solution A is 0.05% TFA in water and solution B is 0.05% TFA in acetonitrile. Typical elution gradients were performed using a C18 column (column size: 21.2×250 mm, 7 μm particle size, Agilent ZORBAX 300SB-C18 PrepHT) using a linear gradient from 5 to 95% Solution B over 45 minutes. Collected fractions were pooled and lyophilized to generate a white powder. Azido-IKVAV peptide was confirmed via MALDI-TOF (positive ion mode) using α-cyano-4-hydroxycinnamic acid (CHCA) as a matrix.

Surface Area Measurements

To measure the surface area of PCL fibers, BET measurements were conducted. The samples were degassed with nitrogen gas to remove impurities from the samples at 40° C. overnight. Krypton gas was absorbed on the surface of PCL fibers and 13 data points were collected with the relative pressure ranging from 0.06 to 0.30. The BET plot was generated with a linear region that has a slope of 2.773±0.048 g/cm$^3$ and an intercept of 0.228±0.010 g/cm$^3$ ($R^2$=0.998).

Results

Coextruded Aligned PCL Fiber

In this example, multilayered melt coextrusion of polymeric fibers was chosen for several reasons. The layered coextrusion system uses two polymer components, in this case PCL and PEO, which are both polymers that have been used in several FDA-approved applications. Additionally, both polymers are inexpensive, costing less than $15/kg. Finally, the method is continuous and solvent free, requiring only a water wash to generate PCL fibers, hence eliminating biologically detrimental effects of solvent based processing. During the extrusion process, PCL and poly (ethylene oxide) (PEO) are melt-pumped and layered vertically in the extrusion line. This vertical bilayer was cut in a horizontal plane in the multiplication die and recombined side-by-side to double the number of vertical layers. This process was repeated ten times to increase the number of layers and conversely, decrease the layer thickness. Following vertical multiplication, PEO is layered on the top and bottom of the vertical multilayers. Finally, the multilayered melt undergoes horizontal multiplication, where it is cut in the vertical direction, and the two flow fields are stacked on top of each other to yield PCL fibers embedded in a PEO tape. This procedure was repeated two times, producing a composite extrudate tape containing 512 PCL domains embedded in a PEO tape. The extruded tape is washed in a water bath for ~24 hours to remove PEO, yielding PCL fibers. Distribution of the size of PCL fibers was examined using scanning electron microscopy (SEM) and was analyzed. The fiber dimensions shows a narrow distribution of size with an average cross-section of 1.49±0.48 μm.

Gradient Photochemistry

In this example, we sought to create a simple method to generate surface-immobilized chemical gradients on aligned extruded fibers. Owing to the ease with which photochemical modification occurs, we aimed to utilize a simple photomasking strategy to modulate the concentration of functionalized benzophenone deposited on the fibers. A 3 cm linear photomask was printed on transparency slides ranging from completely transparent to entirely black (FIG. 12A), allowing us to modulate the UV-intensity for photochemistry by one full order of magnitude. PCL fibers were dip coated in a concentrated solution of propargyl benzophenone (Pr-Bz), allowed to dry, and subjected to UV-irradiation for 20 minutes (FIG. 11).

Upon UV irradiation, Pr-Bz is excited to form a radical species, which can then undergo a radical insertion into the PCL backbone. This resulted in a new covalent bond between Pr-Bz and PCL, leaving surface exposed propargyl groups that could undergo the CuAAC reaction. After alkyne gradient formation, the CuAAC reaction was used to attach Azide Fluor 488 (AF$_{488}$) to the fibers, a green fluorescent dye that allows for simple visualization of the gradient modified surface. The surface gradient was visualized using fluorescence imaging in the green channel, clearly indicating gradient formation (FIG. 12B). The gradient intensity was analyzed by mean fluorescence intensity over the entire fiber bundle to correlate the fluorescent gradient to the linear photomask, showing a strong linear correlation to the mask (FIG. 12C).

Quantification of AF$_{488}$ Gradient

In order to quantify surface coverage following AF$_{488}$ immobilization, dye coverage was quantified using UV-Vis spectroscopy. Dye quantification proves to be much simpler than peptide quantification, and in the past, has correlated well to peptide conjugation. The correlation is likely due to the extreme efficiency of the ligand-accelerated CuAAC reaction. Rather than quantifying the gradient fibers directly, we chose to take individual points within the gradient and understand how UV fluence impacted surface coverage. Three individual photomasks were used to attach Pr-Bz, followed by CuAAC with $AF_{488}$, where photomasks corresponded to (a), (b), and (c) in FIG. 12A (i.e., completely transparent, 50% black, and 100% black) to evaluate surface coverage (FIG. 16). After the CuAAC reaction, fibers were dissolved and dye loading was quantified and compared to BET surface area measurements (18.8 $cm^2$/mg). The quantification of $AF_{488}$ was determined using UV-Vis spectroscopy at 501 nm against a standard curve in dichloromethane following dissolution of PCL-AF488 fibers. Fibers with a transparent photomask, corresponding to spot (c) (FIGS. 12A and 16), allowed UV transmittance of 28.6 mW/$cm^2$ and led to 0.43 nM/$cm^2$ of surface coverage (FIG. 17) on the fiber bundle. An intermediate intensity, corresponding to 50% black in the photomask indicated by spot (b) (FIG. 12A) provided 14.6 mW/$cm^2$ of UV intensity. This photomask yielded 0.24 nM/$cm^2$ of $AF_{488}$ attachment onto the surface of the fibers (FIG. 17). Finally, the UV intensity of the 100% black photomask, corresponding to spot (a) (FIG. 12A) of the gradient photomask yielded 0.09 nM/$cm^2$ of $AF_{488}$ decorated onto the fibers. Gratifyingly, the simple inkjet photomasking technique yielded approximate linear results that allowed us to tune the gradients by nearly an order of magnitude from 0.43 to 0.09 nM/$cm^2$ onto the surface.

Gradient Surface Modification of PCL with IKVAV

It is well known that cells can respond to haptotactic gradients, or surface immobilized gradients of biologically active molecules. Such gradients can lead to enhanced cell adhesion and migration relative to non-gradient surfaces. In particular, neuronal cells are especially sensitive to these chemical perturbations and can undergo axonal elongation in the presence of haptotactic gradients of laminin derived peptides, like IKVAV of YIGSR. We sought to employ this phenomenon with our extruded fibers, employing the same linear gradient as described above. An azide-modified IKVAV was synthesized and clicked onto Pr-Bz modified PCL fibers, using the optimized gradient conditions for photochemistry and ligand-accelerated CuAAC (PCL-g-IKVAV). As IKVAV does not provide the ease of quantification of the dye-immobilized molecules, several characterization techniques were carried out to investigate peptide gradient formation. First, PCL-g-IKVAV was analyzed by ATR-FTIR and FTIR imaging. The C=O stretching mode in the amide I region is coupled to the bending of the N—H bond and the stretching of the C—N bond represented between 1620 and 1640 $cm^{-1}$. The ATR-FTIR spectra at 1628 $cm^{-1}$ confirmed an increasing amide I band (C=O) across the breadth of the fiber length of PCL-g-IKVAV with detection at the 3 different regions of the sample (FIG. 13B). With increasing transparencies of the photomask, more intense amide I peaks are seen, indicating an increasing gradient of amide bonds, as would be expected for gradient IKVAV formation. FTIR imaging was also employed to visualize the spatial distribution of the C=O amide I band and is shown as a chemical heat map (FIG. 13C) from spots (a) to (c) (scale bar on the right indicates intensity of absorbance, blue to red after normalization). The FTIR imaging result correlates well with the full ATR-FTIR spectra as an increase in the intensity of amide C=O bonds is seen, indicating an increase in concentration of IKVAV.

Water contact angle provides an indication of the hydrophilicity and hydrophobicity on the surface of polymeric substrates. Cell adhesion also depends on the wettability of a scaffold surface, especially since synthetic biocompatible polymers, such as PCL, are hydrophobic which usually limits cell interactions with the scaffold. Incorporating peptides such as IKVAV or YIGSR will likely improve the hydrophilicity of the surface, in addition to interacting with cell surface receptors, further enhancing the cell adhesion properties of the polymeric scaffold. Water contact angles were measured on PCL-g-IKVAV fibers from spot 1 to spot 4 indicating a decreasing water contact angle, and hence an increasing amount of surface-immobilized IKVAV (FIG. 14A). Water contact angle values decreased from 107.8±7.5 to 65.5±3.7° (FIG. 14B), indicating that PCL-g-IKVAV fibers become more hydrophilic as surface density is increased. Furthermore, this follows a linear trend as would be expected from our linear photomask. Therefore, it is likely that both gradient hydrophilicity and receptor specific interactions may play a role in improving cell surface adhesion.

Finally, PCL-g-IKVAV fibers were characterized by X-ray photoelectron spectroscopy (XPS) to determine nitrogen content, a unique atom after the fibers are peptide-modified. XPS wide scan of PCL-g-IKVAV fibers, (FIG. 14C) was performed at 4 distinct spots at increasing gradient densities, and the intensity of the N1s was quantified. An increasing intensity of N1s (relative %) at −400 eV was seen, showing successful immobilization of gradiated amounts of IKVAV onto the PCL fibers. The percentages of nitrogen were 3.5, 7.5, 9.8 and 12.0% corresponding to spot 1 to 4 (FIG. 15C) as a result of gradient IKVAV immobilization (see Table 1). This result also shows the linear behavior of the nitrogen to carbon ratio (N/C), confirming linear gradient formation.

TABLE 1

Surface characterization - Relative elemental concentrations of different spots on the PCL-g-IKVAV fibers by XPS and values for water contact angles (right column)

| Sample | Atomic component (%) | | | WCA angle (°) |
|---|---|---|---|---|
| | C (1s) | N(1s) | O (1s) | |
| Spot 1 | 77.9 | 3.5 | 18.6 | 107.8 ± 7.5 |
| Spot 2 | 71.7 | 7.5 | 20.7 | 89.8 ± 3.9 |
| Spot 3 | 70.4 | 9.8 | 19.8 | 74.6 ± 8.1 |
| Spot 4 | 70.1 | 12.0 | 18.0 | 65.5 ± 3.7 |

In Vitro Characterization of Aligned PCL-g-IKVAV Fibers with PC-12 Cells

To determine the effects of the gradient on neural cells, growth of PC-12 cells was evaluated on three different substrates, unmodified PCL fibers, PCL non-gradient IKVAV (PCL-ng-IKVAV) and PCL-g-IKVAV. PC-12 cells are derived from a pheochromocytoma of the rat adrenal medulla, which can differentiate into neurons and are commonly used as a model cell line in regenerative neural medicine. PC-12 cells were seeded onto the fiber and cultured for 5 days in the presence of nerve growth factor (NGF) to allow for neural differentiation and neurite extension. Following incubation, cells were fixed and stained using a NL557 conjugated anti β-III-tubulin antibody that is specific for neural differentiation (red) and DAPI for the nucleus (blue) (FIG. 15). Confocal microscopy images reveal different neurite extension and cellular density of PC-12 cells on each substrate, as well as in three different regions of each substrate. The density of cells on the unmodified PCL fibers, was significantly lower than that observed on the PCL-ng-IKVAV and PCL-g-IKVAV (FIG. 5). Also the 3 different areas on the unmodified PCL showed little adhesion, differentiation, and directed cell alignment (FIGS. 15A-C). This would be as expected, as PCL provides no biologically active cues and the hydrophobic nature of the surface provides little adhesive capabilities for cells.

The biologically active peptide, IKVAV, is known to bind to β-amyloid precursor protein and has been shown to promote adhesion and neurite outgrowth of PC-12 cells. It was postulated that PCL-ng-IKVAV would lead to improved adhesion but would have less propensity for cell alignment and extension than PCL-g-IKVAV fibers. Confocal images indicate a higher density of cells on non-gradient substrates as higher IKVAV densities are seen throughout the non-gradient fibers (FIGS. 15D-F). Although higher IKVAV densities enhanced cell adhesion on PCL-ng-IKVAV, there is minimal neuronal alignment or differentiation of PC-12 cells with a fixed concentration of IKVAV across the sample. Spreading of neurites was in arbitrary directions in the three different spots as observed via anti β-III-tubulin, and neural differentiation was less significant when compared to gradient modified fibers. When non-gradient substrates are compared to PCL-g-IKVAV, several differences arise. FIG. 15G, corresponds to the lowest concentration of IKVAV on the gradient and shows lower numbers of PC-12 cells, as compared to other regions on the same substrate. The highest cell density was seen on the highest concentrations of IKVAV on the gradient fibers (FIG. 15I). In addition, PC-12 cells had noticeably elongated nuclei and neurites along the axis of the PCL-g-IKVAV fibers. The primary direction was along the gradient of the IKVAV motif, which showed the highest cell extension, differentiation and alignment of neurites, as compared to all other samples (FIG. 15G-I). Regardless of peptide concentration on the gradient surface, neurite extension was seen both in the direction of the fibers and along the axis of the gradient. This result implies that the gradient surface of PCL-g-IKVAV fibers is critical for strong biological activity and that the higher concentrations of IKVAV impacted cell adhesion. The gradient fibers effect differentiation of PC-12 cells and their alignment more so than solely the topographical cues of the aligned fiber direction, although both components are interrelated.

Photochemical gradient modification of a scalable class of melt coextruded fibers allowed for immobilization of azide-modified peptide gradients on the surface of aligned PCL fibers. Melt coextrusion allows for a significantly higher throughput of fiber production when compared to other common fiber processing techniques. This photochemical modification is modular and allows for patterning of surface groups about the fiber. Gradient immobilization of the laminin derived peptide, IKVAV, onto PCL fibers was easily accomplished.

Example 3

Figure 25:
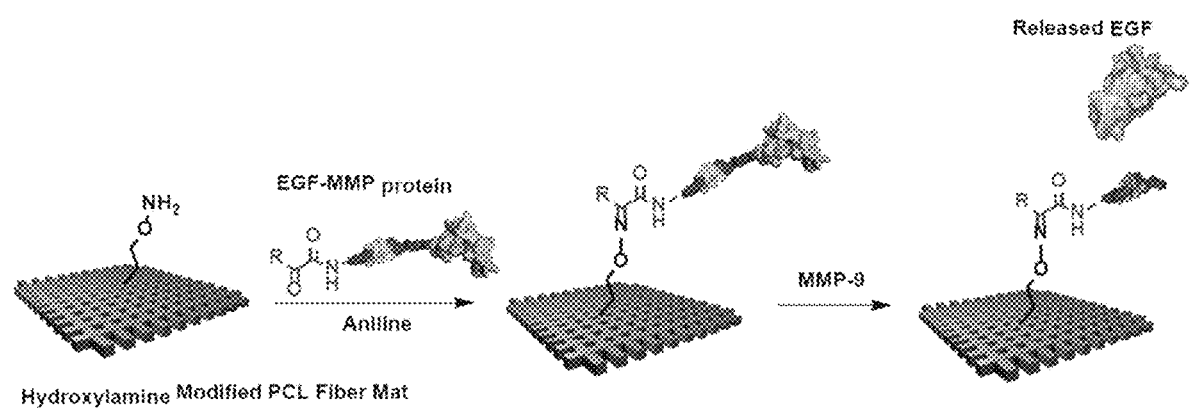
FIG. 25 illustrates bioconjugation of EGF to an aminooxy decorated PCL fiber mat and MMP-mediated release.

We developed a wound healing patch where a genetically-engineered EGF was covalently immobilized onto a polymeric fiber mat, thus eliminating the chemical driving force for release to the environment. A MMP-cleavage site was introduced between the active protein and the covalent attachment point on the mat, thus EGF would be liberated by MMP-9, a commonly upregulated MMP during the early wound healing stages (FIG. 25). The protein-conjugated fiber mat is envisioned as a topical depot of EGF, which can be tuned to provide the optimal amounts of EGF for treatment of acute and chronic wounds. An enzymatically responsive recombinant EGF was synthesized with several features included at the N-terminus of the protein (EGF-MMP, FIG. 18A). The N-terminus was modified since the C-terminal sequence is responsible for receptor binding. The recombinant protein contained a N-terminal sequence (AKT) that is highly reactive for bioconjugation using pyridoxal 5'-phosphate (PLP) mediated bioconjugation. This method is a site-selective modification that utilizes N-terminal transamination of proteins to introduce a ketone or aldehyde, which could further undergo oxime ligation with a polymer substrate (see below). Next a polyhistidine tag was included for affinity purification. Finally, a MMP cleavage site for triggered release of the protein from the scaffold was included downstream of the remaining N-terminal extension. The chosen octapeptide sequence (VPLSLYSG) (SEQ ID NO: 1) is cleavable by MMPs, including MMP-9 ($k_{cat}/K_M = 49,000 \pm 3,000$), and is selectively cleaved by MMPs that are upregulated in early stages of the wound healing cascade. Only a 4-residue extension remains at the N-terminus following release, based on this domain orientation.

The gene was synthesized and cloned into the pET28a(+) expression vector (pET28EGF-MMP), followed by standard IPTGinduced protein expression and purified via affinity chromatography. An EGF mutant without the MMP-cleavage site was synthesized in the same manner as a non-responsive control (FIG. 18B). The two proteins were analyzed via SDS-PAGE to determine purity, resulting in a single band corresponding to a molecular weight of ~10 kDa (FIG. 18C). MALDI-TOF mass spectrometry confirmed the molecular weight of the recombinant proteins, which are consistent with the theoretical molecular weights of control EGF and EGF-MMP, 7,344 kDa and 8,162 kDa (expected molecular weight 7,344 kDa and 8,162 kDa), respectively (FIG. 18D).

Figure 19A:
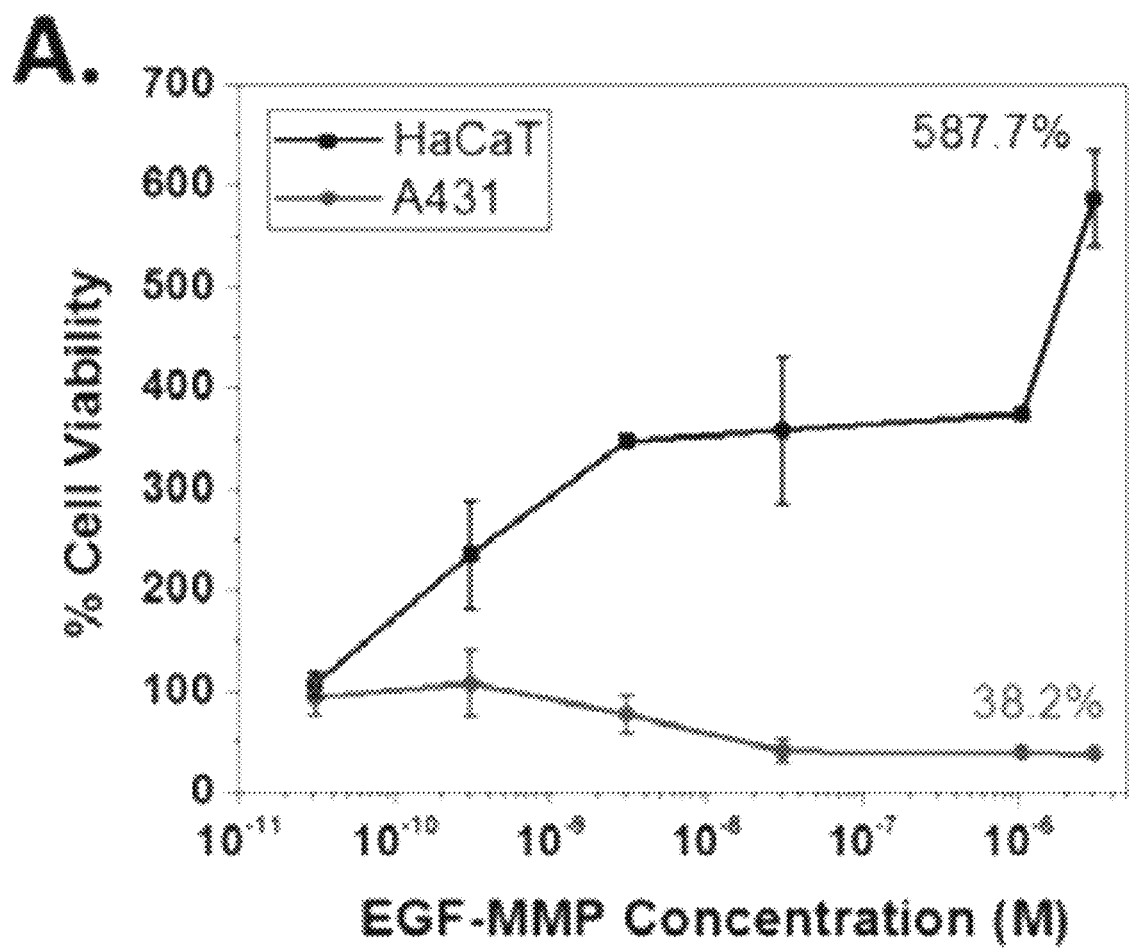
FIGS. 19(A-B) illustrate (A) MTT cell viability assay of HaCaT (human keratinocytes) and A431 (epidermoid carcinoma) cells in the presence of EGF-MMP (B) MALDI-TOF MS indicating the molecular weight of EGF-MMP protein before and after MMP-9 cleavage.

The in vitro biological activity of the purified EGF-MMP protein was confirmed using both human keratinocytes (HaCaT) and epidermoid carcinoma (A431) cell lines. EGF is a potent mitogen in HaCaT cells, even at low concentrations, and improves further at high concentrations. EGF has the opposite biological effect on A431 cells, promoting apoptosis at high concentrations.28 Relative viability was evaluated utilizing the MTT proliferation assay on the two cell lines. HaCaT cells demonstrated a ~6-fold increase in cell viability from 100 to 587.7% at the highest concentration of EGF-MMP (FIG. 19A). In contrast, the cell viability of A431 cells decreased from 100 to 38.2% as the concentration of EGFMMP increased. These results were consistent with literature values and demonstrated that the purified recombinant EGF-MMP has the expected biological activity and the mutations introduced at the N-terminus do not affect the activity.

Figure 19B:
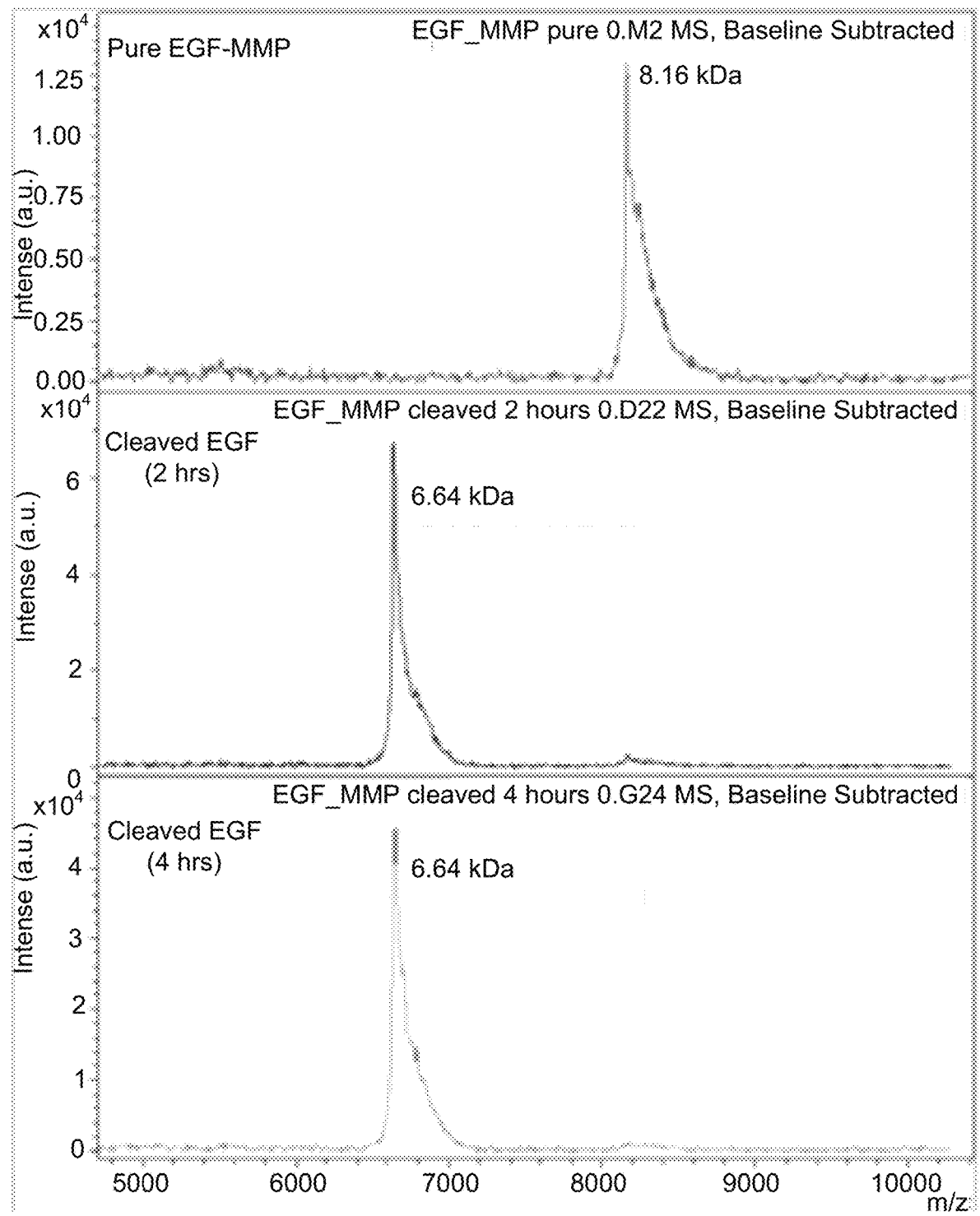

In silico modeling predicted that the MMP reactive octapeptide would be cleaved by MMP-9 orders of magnitude faster than other amino acid sequences in EGF-MMP. Cleavage of EGFMMP was performed via incubation with MMP-9 for 2 and 4 hours (FIG. 19B). The molecular weight of the protein was determined by MALDI-TOF following cleavage. After 2 hours, the molecular weight decreased from 8.16 kDa to 6.64 kDa, in precise agreement with the theoretical molecular weight of cleaved EGFMMP (6.64 kDa). After 4 hours, the mass spectrum remained as a single peak at 6.64 kDa, indicating no proteolytic activity at other sites on the protein. This result indicated over 99% conversion to the cleaved product by integration of MALDI-TOF data, with no side products.

Figure 22A:
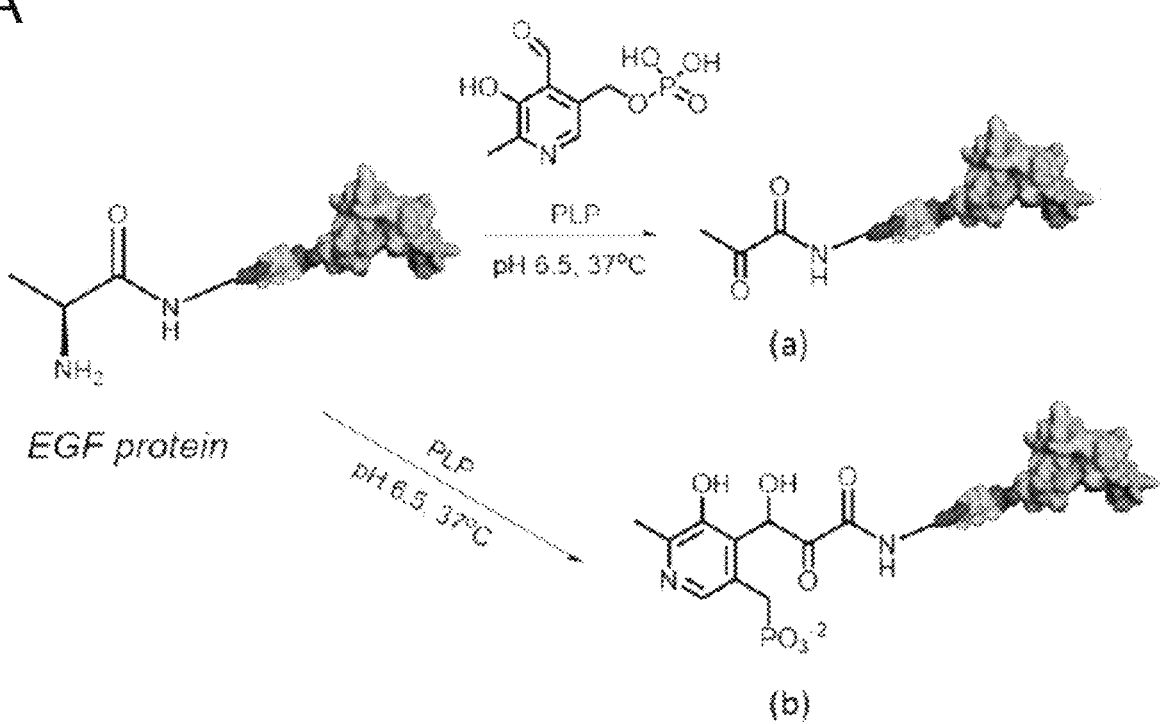
FIGS. 22(A-B) illustrate proposed mechanism for site-specific modification of the protein in the presence of PLP. MALDI-TOF mass spectrum indicates protein (A) at 8162 m/z and (B) at 8409 m/z, matching model molecular weights, indicating modified EGF-MMP.
Figure 22B:
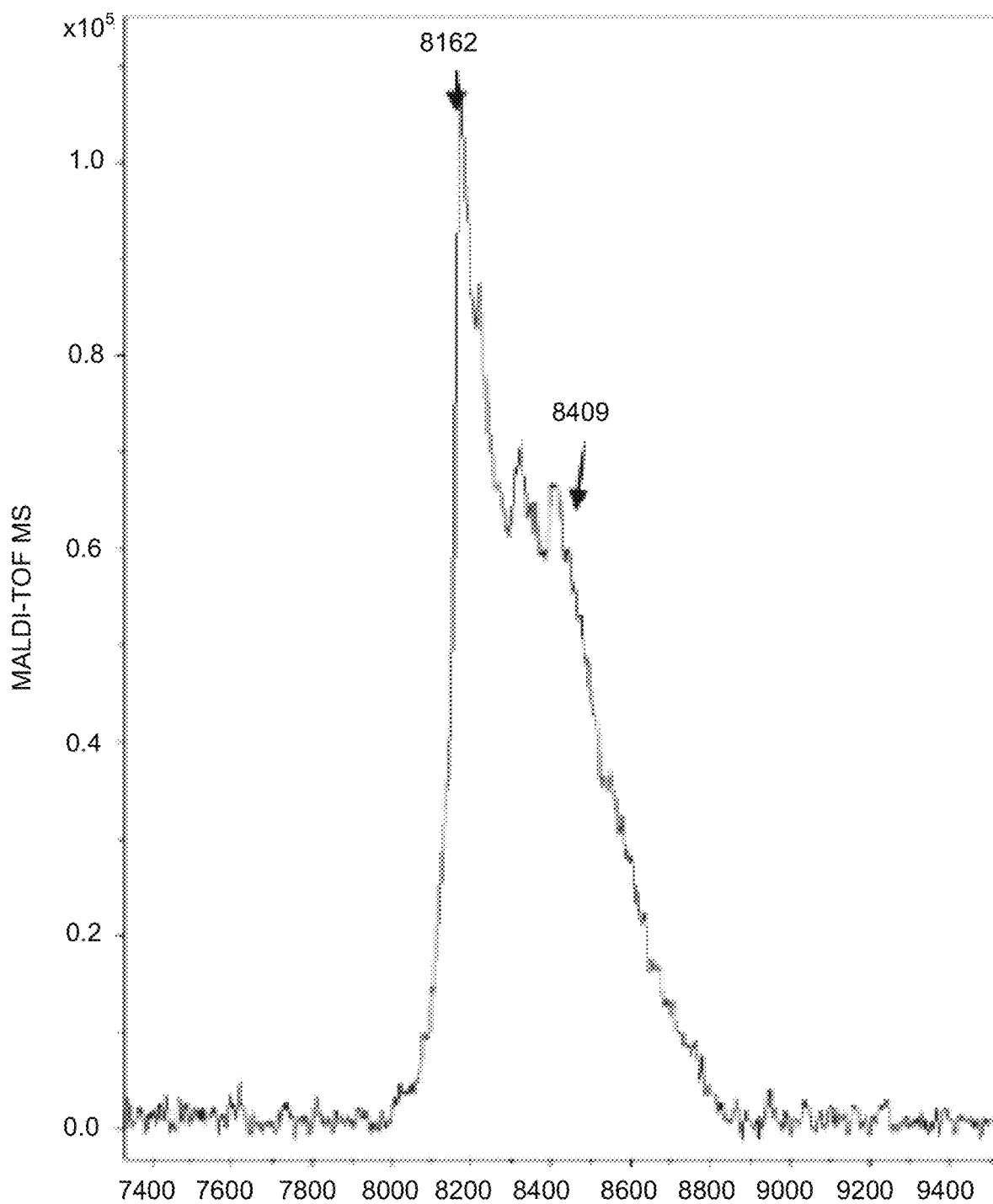
Figure 23A:
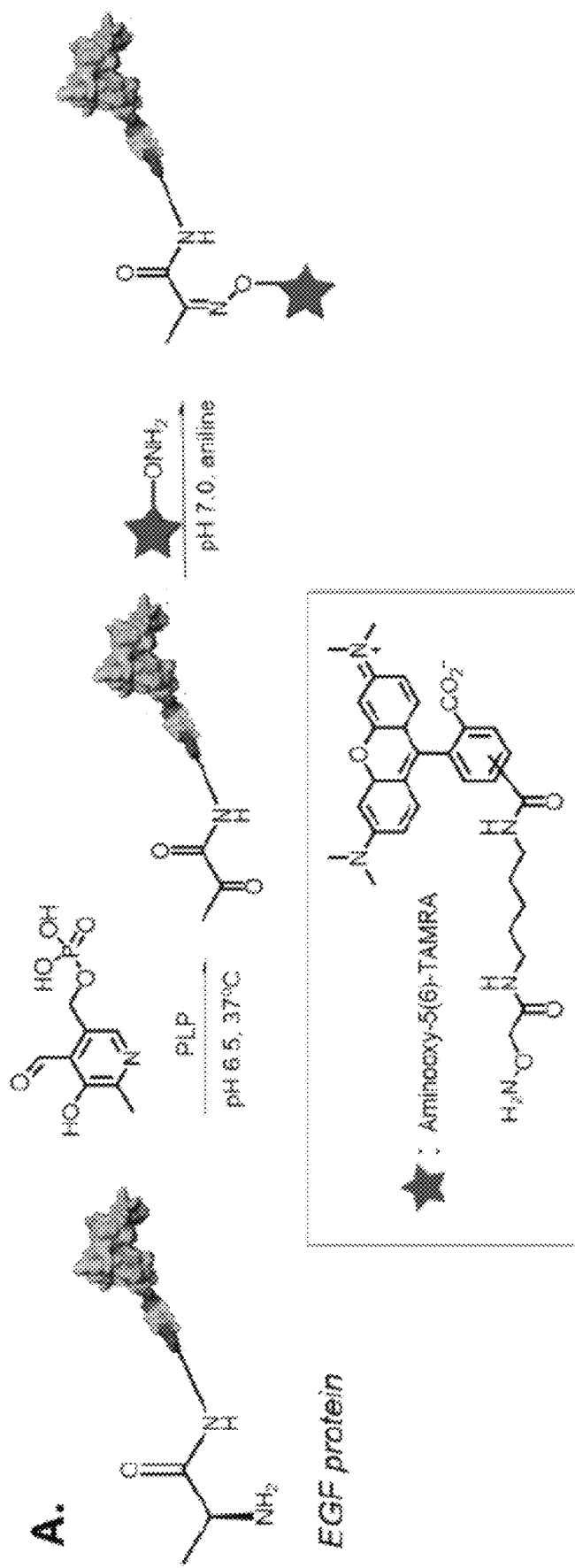
FIGS. 23(A-B) illustrate (A) Scheme of oxime ligation of the TAMRA dye with the ketone-modified EGF protein, (B) FPLC trace of control EGF and EGF-MMP (left); FPLC trace of ketone modified control EGF and EGFMMP (middle); FPLC trace of TAMRA conjugated control EGF and EGF-MMP(right). The maximum absorbance of aminooxyl-5(6)-TAMRA is shown at 555 nm (red). The other wavelengths monitored were 280 nm (black) and 260 nm (blue).
Figure 23B:
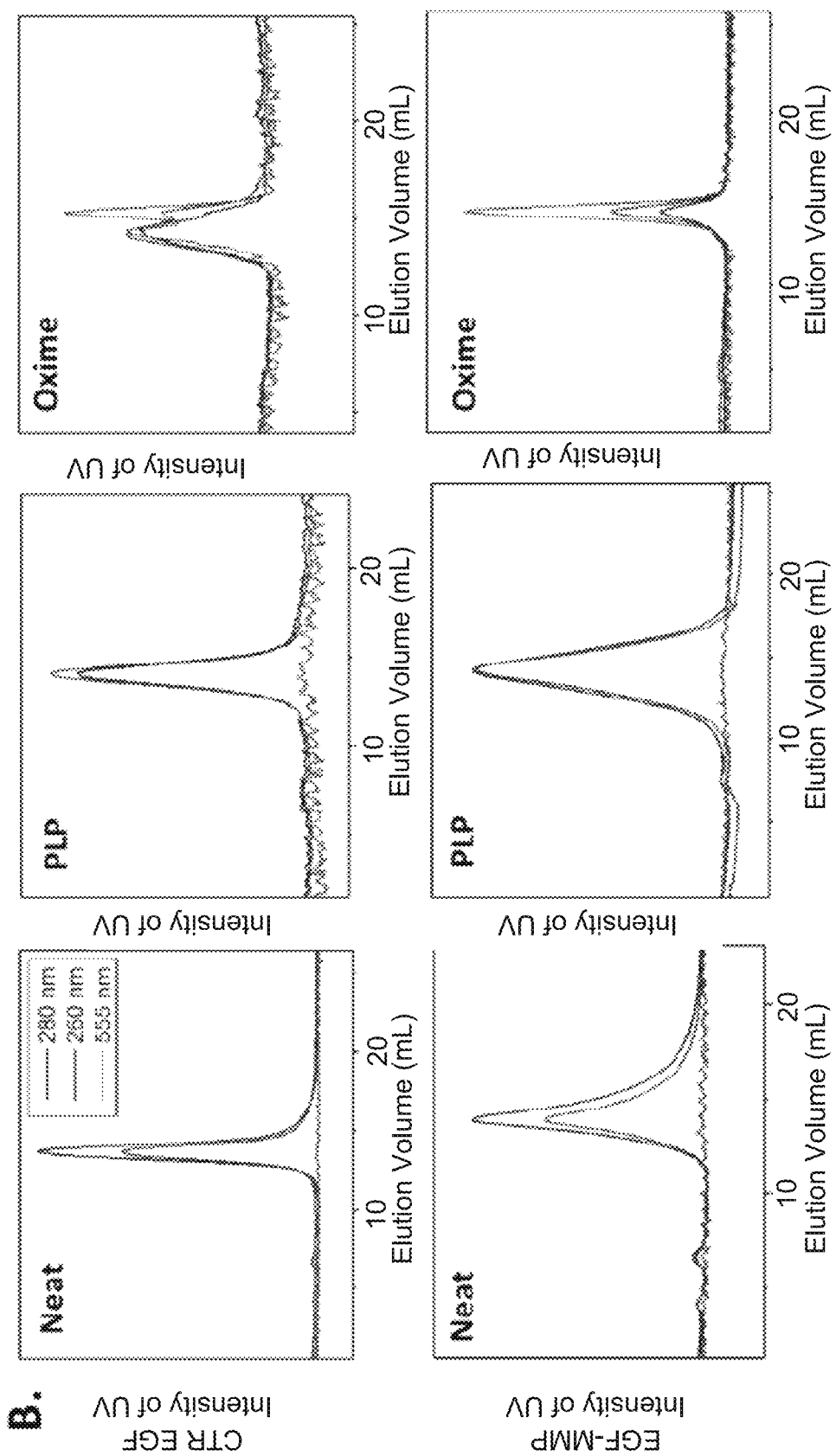

The PLP-mediated transamination reaction was employed to introduce a ketone moiety at the N-terminus of EGF for conjugation to the fiber mat and conversion was verified using MALDI-TOF. Two significant peaks were found (FIG. 22), one corresponding to the transamination product and another that correlates to an expected PLP adduct. The undesired product still contained a ketone group and was able to undergo oxime formation. Bioorthogonal ligation has been widely explored in chemical biology for the reaction of ketones with hydrazides and alkoxyamines to form hydrazones and oximes at acidic pH. Oxime chemistry prefers slightly acidic conditions, however proteins may precipitate under these conditions due to the relatively higher isoelectric points of proteins (pIEGF-MMP=6.2) than those that are preferable for oxime ligation. Aniline catalysts effectively accelerate oxime formation by forming an in situ highly reactive protonated aniline Schiff base at neutral pH. Therefore, aniline was utilized as a nucleophilic catalyst for the bioconjugation reaction. EGF-MMP was modified with the ketone moiety at the Nterminus in the presence of PLP, as previously described. Excess PLP was removed via centrifugal spin filtration and the ketone functionalized protein was conjugated to aminooxy functionalized TAMRA dye with a minimal amount of aniline catalyst (FIG. 23A). After removal of free dye and catalyst via centrifugal spin filtration, fast protein liquid chromatography (FPLC) was performed to monitor the elution volume of the PLP reacted protein and dye labeled EGF-MMP, both the modified and unmodified proteins showed identical elution volumes (FIG. 23B). Furthermore, after oxime ligation a peak at 555 nm co-eluted with the protein peaks, demonstrating successful bioconjugation. The polymeric material chosen was a microfibrous coextruded poly(ε-caprolactone) (PCL) non-woven mat. Multilayered coextrusion of nano- and microfibers is a new manufacturing technique that is high throughput, allows for control over fiber dimensions and porosity, and is amenable to site-specific chemical modification strategies. Nonwoven poly(ε-caprolactone) (PCL) fiber mats were fabricated (FIG. 20A) with a high porosity and near homogeneous pore size distribution (25.6 μm, FIG. 20B). This pore size is in the range of commercially available wound healing patches. In this work, PCL was chosen due to its processing flexibility and biocompatibility, specifically as a wound dressing.

Figure 24:
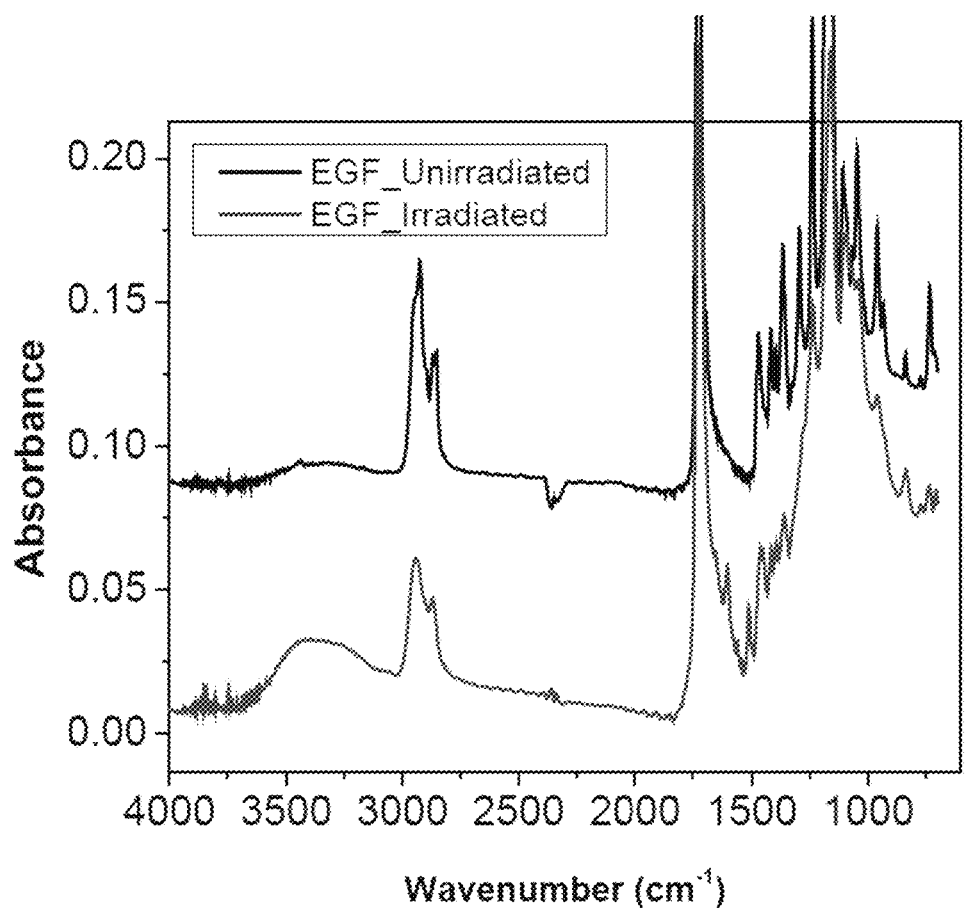
FIG. 24 illustrates ATR-FTIR spectra of EGF-MMP conjugation to PCL fiber mat. The spectrum from the back of the fiber mat is shown in black (no UV irradiation) and the spectrum from the front is shown in red (UV irradiation).

Aminooxy benzophenone was synthesized as a linker for oxime chemistry, and deposited onto the PCL fiber mat through UVinitiated photochemistry. Ketone-modified EGF-MMP was then covalently conjugated onto the aminooxy fiber mat via oxime ligation. Since protein adsorption without covalent attachment can provide false readings, non-specific protein absorption onto the hydrophobic fiber mat was performed on unmodified mats. The protein modified PCL fiber mat was scanned using ATRFTIR to confirm the presence of EGF-MMP (FIG. 20C and FIG. 24). The unirradiated fiber mat showed no amide signal from the protein, while the UV irradiated side clearly showed EGF-MMP, as indicated by C═O stretching vibrations at 1615 cm−1 from amide I, N—H bending vibration/C—N stretching vibration at 1505 cm−1 from amide II, and N—H stretching vibration near 3300 cm−1 from amide A. This result clearly indicated that protein conjugation only proceeds onto the aminooxy modified PCL fiber mat. We next explored whether incubation with MMP-9 releases EGF conjugated to the fiber mat. For comparison, a conjugated noncleavable control EGF was also studied. The release kinetics of EGF-MMP and control EGF from the fiber mats were determined by incubation with activated MMP-9 and quantification via ELISA. The concentration of released protein was normalized by the weight of each fiber mat. The ELISA results indicated that EGF-MMP was rapidly released, resulting in ~11 ng EGF/mg PCL released over the first 10 minutes after introduction of the enzyme (FIG. 20D). However, the control EGF conjugated fiber mat showed no significant protein release after introduction of the MMP enzyme. After 4 hours of incubation, the control EGF protein showed a negligible amount of released protein while the EGF-MMP fiber mat released ~20 ng of EGF per milligram of PCL fiber mat. Incubation was carried out for 24 hours with MMP-9, with no further increase in released protein. Thus, the conjugation scheme yielded 20 ng EGF/mg PCL that was accessible. When normalized per surface area, based on Brunner-Emmett-Teller (BET) surface measurement (43.2 cm2/mg of PCL fiber mat), ~0.46 ng EGF/cm2 of PCL fiber mat was available for release. The results indicated that EGF-MMP release was specifically triggered by MMP-9, while the control EGF remained conjugated to the polymer scaffold.

Wound healing was simulated using a monolayer scratch test with HaCaT cells, a common model for migration and proliferation in the wound healing process (FIG. 21). A control sample with no fiber mat and three different fiber mats were evaluated; unmodified PCL, control EGF-modified PCL, and EGF-MMP-modified PCL. Cells were grown to confluency and a scratch was introduced using a micropipette tip. The cells were then incubated with a fiber mat and MMP-9. After 24 hours of incubation, the scratches were measured by optical microscopy. No scratch closure was observed for controls with neat PCL or no fiber mat (FIG. 21). We observed a decreased gap for cells incubated with control EGF fiber mats. The improvement is likely due to a small amount of EGF released, either through non-specific adsorption to the surface or low-level cleavage of unintended sites. Previous studies have shown EGF concentrations as low as 1 ng/mL can have a pronounced effect on gap closure. In contrast, the EGF-MMP mat demonstrated complete gap closure and significantly enhanced proliferation. Thus, the EGF-MMP fiber mat responded to MMP-9 to stimulate complete wound closure in the simulated healing.

This study describes a new paradigm in triggered release of growth factors based on genetic engineering, where therapeutic protein release is triggered by the biology of wound healing. Recombinant EGF was engineered to release only in the presence of wound healing cues. The results presented here clearly indicate that EGF could be engineered for selective release by MMP-9.

Moreover, released EGF from the EGF-MMP conjugated fiber promoted proliferation and migration of cells. The amount of EGF delivered in response to MMP-9 can be tuned in the future via the amount of aminooxy groups coupled onto the fiber mat and release kinetics can be controlled by changing the MMP responsive sequence.

Experimental Section

Materials

Aminooxy-5(6)-TAMRA was purchased from Biotium, Inc. BL21(DE3) *E. coli* were purchased from Genlantis. Aniline, 1,8-Diazabicyclo[5.4.0]undec-7-ene (DBU), N-hydroxyphthalimide, and α-cyano-4-hydroxycinnamic acid were purchased from Sigma-Aldrich. 1-Step TMB substrate, agarose, calcium chloride, isopropyl β-D-1-thiogalactopyranoside, kanamycin sulfate, potassium phosphate monobasic anhydrous, potassium phosphate dibasic anhydrous, pyridoxal 5'-phosphate, Miller LB broth, methanol, SeeBlue Plus2 protein ladder, sodium hydroxide, sulfuric acid, Tween-20, Tris-HCl, potassium carbonate, N,N-dimethylformamide, potassium iodine, sodium bicarbonate, chloroform-d6, and urea were obtained from Fisher Scientific. Recombinant, human pro-MMP-9 expressed in CHO cells and MMP-2/MMP-9 Substrate I, Fluorogenic were purchased from EMD Millipore. Dimethyl sulfoxide (DMSO) was purchased from Amresco. Amino-phenyl mercuric acetate, imidazole, 4-hydroxyl benzophenone, 2-bromoethanol, dichloromethane, trimethylamine, and Triton X-114 were purchased from Acros Organics. Chemically competent NEB 5 α *E. coli*, NcoI restriction enzyme, XhoI restriction enzyme, T4 polynucleotide kinase, and T4 ligase were purchased from New England Biolabs. Recombinant human epidermal growth factor was purchased from BD Bioscience. Mouse anti-human epidermal growth factor IgG and horse radish peroxidase conjugated goat anti-mouse IgG secondary antibody was purchased from Life Technologies. HaCaT and A431 cells were generous gifts from the dermatology department at Case Western Reserve University.

Instrumentation

Proton nuclear magnetic resonance ($^1$H NMR) were recorded on a Varian Inova 600 MHz NMR spectrometer in deuterated solvents. Chemical shifts are reported in parts per million (ppm, δ) relative to residual solvent (CDCl3, δ 7.26). Fast protein liquid chromatography (FPLC) was performed using a GE Healthcare AKTAFPLC 900 chromatography system equipped with a Superdex 75 10/300 GL size exclusion column. A Thermo Finnigan LCQ Advantage LC/MS (ESI) was used to confirm the molecular weight of synthesized aminooxy benzophenone. SDS polyacrylamide gel electrophoresis (PAGE) was performed on Novex NuPAGE 4-12% bis-tris protein gels (1.0 mm×12 well) (35 minutes, 200 V, 1× NuPAGE MES SDS running buffer). Gels were stained with Coomassie SimplyBlue SafeStain (Life Technologies). Multilayer coextrusion was performed using the CLiPS two-component coextrusion system with 23 multipliers. ATR-FTIR imaging was conducted on a Digilab FTS 7000 spectrometer, a UMA 600 microscope. A high-intensity UV lamp (Bluepoint 4 Ecocure from Honle UV America Inc.) was used for surface modification of the PCL fibers with aminooxy benzophenone. The molecular weights of the synthesized proteins were measured on a Bruker Autoflex III MALDI-TOF/TOF mass spectrometer using α-cyano-4-hydroxycinnamic acid (CHCA) as a matrix. UV-vis spectra were collected using a Shimadzu BioSpecnano UV-vis spectrophotometer.

Synthesis of Aminooxy-Benzophenone

Aminooxy-benzophenone was synthesized. 2-(4-Benzoylphenoxy)ethanol (1). 4-Hydroxylbenzophenone (2 g, 10 mmol) and anhydrous potassium carbonate (2.76 g, 20 mmol) were stirred in a round bottom flask in 30 mL of N,N-dimethylformamide (DMF). 2-Bromoethanol (1.07 mL, 15 mmol) and potassium iodide (KI) (0.8 g, 4.8 mmol) were added, and the reaction mixture was heated for 24 hours at 65° C. After the reaction, the mixture was cooled to room temperature and then filtered. The yellow filtrate was slowly precipitated in 700 mL of deionized water in an ice bath. A white powder was collected by centrifuging at 10,000 rpm for 10 min (80% yield) 1H NMR (600 MHz, chloroform-d) δ 7.82 (d, 2H), 7.76 (d, 2H), 7.57 (t, 1H), 7.47 (t, 2H), 6.99 (d, 2H) 4.17 (t, 2H), 4.01 (t, 2H). ESI-MS (m/z, rel %) 243.0 ([M+H]+, 10%), 264.9 ([M+Na]+, 90%) calculated for $C_{15}H_{14}O_3$.

Methyl sulfonyl benzophenone (2). 2-(4-Benzoylphenoxy)ethanol (2 g, 8 mmol) in DCM was cooled to 0° C. in an icebath. Triethylamine (TEA) (2 g, 2 mmol) was mixed and then methyl sulfonyl chloride (2.27 g, 1.2 mmol) was added by syringe into the same flask. The reaction was performed at room temperature and stirred overnight in a nitrogen atmosphere. Crude material was sequentially washed with saturated $NaHCO_3$ and brine solution. The organic layer was dried in vacuo. $^1$H NMR (600 MHz, chloroform-d) δ 7.84 (d, 2H), 7.75 (d, 2H), 7.57 (t, 1H), 7.48 (t, 2H), 6.98 (d, 2H), 4.61 (t, 2H), 4.33 (t, 2H), 3.1 (s, 3H) ppm. ESI-MS (m/z, rel %) 321.0 ([M+H]+, 100%), calculated for $C_{16}H_{16}O_5S$.

Aminooxy benzophenone (4). Methyl sulfonyl benzophenone (2 g, 6 mmol) was added to a round bottomed flask with 1,8-diazabicyclo[5.4.0]undec-7-ene (DBU) (0.93 mL, 7.5 mmol) and N-hydroxyphthalimide (1.3 g, 7.5 mmol) in DMF (50 mL). The reaction proceeded overnight at room temperature with stirring. The following day, DMF was removed by rotary evaporation. The crude reaction was re-suspended in dichloromethane (DCM) and DBU was filtered via flash silica column chromatography. The filtrate in DCM was washed with brine and sodium bicarbonate, dried over anhydrous sodium sulfate, and filtered. The dried phthalimide benzophenone (3) (1 g, 2.6 mmol) was re-dissolved in acetonitrile (50 mL). Hydrazine monohydrate (0.42 g, 13 mmol) was added and the mixture was stirred for two hours at room temperature. After concentrating the reaction by rotary evaporation, 20 mL of DCM was added and the mixture was filtered over a plug of celite under vacuum. The product was purified via silica flash chromatography (n-hexane:ethyl acetate, 1:2, v/v). $^1$H NMR (600 MHz, chloroform-d) δ 7.88 (d, 2H), 7.79 (d, 2H), 7.61 (t, 1H), 7.52 (t, 2H), 7.02 (d, 2H), 5.60 (s, 2H) 4.28 (t, 2H), 4.02 (t, 2H) ppm. ESI-MS (m/z, rel %) 280.0 ([M+Na]+, 100%), calculated for $C_{15}H_{15}NO_3$.

Protein Sequences and Plasmid Generation

Epidermal growth factor used in this study was produced recombinantly in *E. coli* to incorporate a PLP reactive site and MMP cleavage site into the sequence. The protein sequence for the mutant, referred to as EGF-MMP, is as follows:

(SEQ ID NO: 2)
AKTHHHHHHVPLSLYSGNSDSECPLSHDGYCLHDGVCMYIEALDKYACNCV
VGYIGERCQYRDLKWWELR

The DNA sequence was generated from the protein sequence using GeneDesign 2.0 software and optimized for *E. coli* codon usage. The DNA sequence is given below with the added NcoI and XhoI cut sites underlined at the 5' and 3' ends respectively.

(SEQ ID NO: 3)
5' ATGCTA<u>CCATGG</u>CTAAAACCCACCACCACCACCACCACGTTCCGCTGT

CTCTGTACTCTGGTAACTCTGACTCTGAATGCCCGCTGTCTCACGACGTT

ACTGCCTGCACGACGGTGTTTGCATGTACATCGAAGCTCTGGACAAATACG

CTTGCAACTGCGTTGTTGGTTACATCGGTGAACGTTGCCAGTACCGTGACC

TGAAATGGTGGGAACTGCGTTAA<u>CTCGAG</u>TGACTC 3'

The gene was produced via primer overlap PCR of primers purchased from Integrated DNA Technologies designed by GeneDesign 2.0 software. The PCR was run for 55 cycles and the product was purified using an agarose gel, the band excised, and the excised band was spin column purified. The purified product was digested with NcoI and XhoI and spin column purified. The product was then ligated via T7 DNA ligase into a pET28a(+) vector that had been digested with NcoI and XhoI. The ligation mixture was transformed into chemically competent NEB5α *E. coli* and plasmids were extracted from isolated colonies. The insertion of the sequence into the plasmid was verified via sequencing with T7 promoter primers and the pET28(EGF-MMP) plasmid was isolated. A mutant of the EGF-MMP protein was made to remove the MMP cutsite for control experiments (referred to as EGF), with the protein sequence given below:

(SEQ ID NO: 4)
AKTHHHHHHNSDSECPLSHDGYCLHDGVCMYIEALDKYACNCVVGYIGERC

QYRDLKWWELR

The PLP reactive site is highlighted in red and the His tag for purification is highlighted in green. Primers were designed for whole-plasmid PCR of the pET28(EGF-MMP) plasmid with the removal of the DNA sequence encoding the MMP cut-site amino acid sequence. PCR was run with the primers and pET28(EGF-MMP) plasmid and the resulting PCR mixture was treated with T7 polynucleotide kinase and then ligated with T7 DNA polymerase. The ligation mixture was transformed into chemically competent NEB5α $E.$ $coli$ cells and isolated colonies had plasmids sequenced as previously described. The pET28(EGF) plasmid was isolated from successfully transformed colonies.

Recombinant EGF Protein Expression and Purification

Chemically competent BL21(DE3) $E.$ $coli$ cells were transformed with pET28(EGF-MMP) or pET28(EGF) and plated onto LB agar media containing 50 μg/mL kanamycin. After overnight incubation at 37° C., 100 mL of LB media containing 50 μg/mL kanamycin was inoculated with a well-isolated colony and incubated overnight at 37° C. with agitation at 250 rpm. The overnight culture was then diluted into 1000 mL of LB media containing 50 μg/mL kanamycin and incubated at 37° C. with agitation at 250 rpm. Cell culture growth was monitored by optical density at 600 nm (OD600) utilizing UV-vis spectroscopy. When the OD600 of the cultures reached approximately 0.8 (mid-log phase), protein expression was induced by addition of 10 mL of 100 mM IPTG resulting in a final concentration of 1 mM. Shaking was continued at 37° C. for an additional 6 hours, at which point cells were collected by centrifugation in an Eppendorf A-4-81 rotor at 4000 rpm (4° C.) for 30 min. The supernatant was decanted and the cell pellet was frozen at −80° C. overnight. Cells were resuspended in 50 mL of 50 mM phosphate buffer with 500 mM NaCl (pH 7.4) and this buffer was used for subsequent steps in the purification. Samples were lysed with a microtip sonicator (10 min total sonication time, cycles of 30 s on/30 s off, power output of 6) in an ice bath. The resulting cell debris was pelleted in an Eppendorf A-4-81 rotor at 4000 rpm (4° C.) for 30 min and the supernatant was decanted. The expressed protein was present in the pellet as an inclusion body. The inclusion bodies were denatured by incubating the re-suspended pellets in 50 mL of 4M urea phosphate buffer for 1 hour at 4° C. Solids were pulled out of the solution and the inclusion body solution was incubated with 8 mL of HisPur cobalt resin that had been washed and equilibrated to buffer. The inclusion body solution was allowed to incubate for 1 hour and then loaded into a fritted syringe. The resin bed was allowed to settle under gravity flow and washed with 4 M urea buffer containing 5 mM imidazole for 16 column volumes. The resin bed was then eluted with an imidazole gradient all made in 4 M urea buffer of 15, 25, 35, 45, 55, 65, 75, 85, 95, and 105 mM imidazole. 6 mL was used for each concentration and fractions were collected under gravity flow. The column was fully eluted using 6 mL of 150 mM imidazole and the fractions were analyzed using SDS-PAGE. Fractions containing pure recombinant protein were pooled together and refolded through sequential dialysis against buffer containing 3, 2, and 1 M urea using 3.5K MWCO dialysis tubing for a minimum of 4 hours each. The refolding was then completed via dialysis against phosphate buffer 3 times for a minimum of 4 hours each. The refolded protein solution was concentrated using 3.5K MWCO of centrifugal spin filtration (8,000 rpm) and quantified via 280 nm absorbance (ε280=20,315 and 18,825 M−1 cm−1 for EGF-MMP and EGF respectively). The purified proteins were analyzed via SDS-PAGE, FPLC, MALDI-TOF MS.

EGF-MMP Cleavage Test by MMP-9

100 mg/mL of EGF-MMP was prepared (n=3) in 2 mL of PBS buffer. In order to activate MMP-9 enzyme, aminophenyl mercuric acetate (APMA) (3.5 mg, 10 mmol) was dissolved in 1 ml of DMSO and the solution was diluted with reaction buffer (50 mM Tris-HCL pH 7.4, 1 mM CaCl2, 0.05% Triton X-100) to a final concentration of 2 mM APMA. 100 μL of the APMA solution was added to 900 μL of phosphate buffer (50 mM phosphate buffer with 500 mM NaCl, pH 7.4), then 200 nM of MMP-9 (1 μL) was added and reacted for 16 hours at 37° C. 10 μL of activated MMP-9 was added to the protein sample, after 60 and 120 minutes respectively, the samples were collected. MALDI-TOF was utilized to measure the molecular weight of EGF-MMP.

Melt Coextrusion of PCL Fibers

The melt coextrusion process began with PCL (CAPA 6800 pellets, MW=80 kg/mol) and PEO. In order to match the rheology of PCL and PEO for the melt extrusion processing, two different molecular weights of PEO (Dow Chemical, POLYOX N80 (MW=200 kg/mol) and POLYOX N10 (MW=100 kg/mol) were used with a ratio of 30:70 (200 kg/mol:100 kg/mol, N80:N10). The mixture of two molecular weights of PEO was used to ensure a viscosity match between PEO and PCL, critical to maintaining fiber uniformity. The two grades of PEO were pre-mixed using a Haake Rheodrive 5000 twin screw extruder and pelletized. The viscosities of the obtained PEO blend and PCL melt matched at 180° C., which was chosen as the extrusion temperature. PEO and PCL were completely dried at 40° C. under high vacuum for 48 h in advance of co-extrusion to prevent void volume formation from residual moisture. PCL fiber domains embedded in a PEO matrix were fabricated via multilayer co-extrusion at 180° C. 18 vertical multipliers and 5 horizontal multipliers were utilized in this process. Finally, this structure went through a 3" exit die, and the extruded tape contained 8192 by 32 fiber domains. The extruded tape was collected on a chill roll at room temperature with a speed of 15 rpm.

Preparation of Non-Woven PCL Fiber Mats

To remove the separating PEO domains, the composite tape was cut (10 cm length) and placed in a water bath while stirring (12 hours). After prolonged immersion the majority of the PEO was removed from the PCL/PEO composite tape yielding PCL fiber bundles. Two strips of PCL fiber bundles were stacked in a cross-ply (90° C.) on a metal plate and covered by an aluminum grid of mesh size (250 μm). A high pressure waterjet, through a 0.010" diameter nozzle, was swept across the fibers parallel to the directions of the fibers on the top and bottom of the fiber mat for 5 minutes each with a 500 psi rotator pressure. This process removed the remaining residual PEO and produced a non-woven fiber mat. The pore size of the fiber mats was determined by a porometer. The specific surface area of the fiber mat was analyzed via multipoint Brunner-Emmett-Teller (BET) analyzer (Micrometrics, TriStar III) after degassing at 40° C. under nitrogen for 24 h.

Photochemistry 20 mg of aminooxy benzophenone, was dissolved in methanol (MeOH) (10 mg ml$^{-1}$). Non-woven PCL fiber mats were cut to 1 cm×1 cm, width and length. Each sample was soaked in the aminooxy benzophenone solution for 5 min and then air-dried at room temperature. The dried samples were placed on a glass slide and irradiated using a UV source with a 320-390 nm filter for 10 minutes and the fiber mat was flipped and irradiated again (Intensity=33.5 mW cm−2, n=3). Unreacted aminoxy benzophenone was removed by washing the fiber mats in MeOH overnight for a total of 3 washes and then the samples were vacuum dried.

Transamination of EGF by PLP 200 mM of pyridoxal 5'-phosphate (PLP) was dissolved in PBS buffer and titrated with 6N NaOH to pH 6.5. A 1:1 (protein:PLP, v/v) solution (the final concentrations of PLP and the protein were 100 mM and 5 mM, respectively) was made with a final pH of 6.5 and incubated at 37° C. for 1 hour. After incubation, the solution was filtered using 3.5K MWCO centrifuge filter. The purification proceeded until no residual PLP was observed in the flow-through by UV-Vis spectroscopy at 414 nm. In order to determine the success of the PLP reaction, the presence of the ketone on the protein EGF-MMP (or control EGF) was probed by MALDI which was used to investigate the molecular weight of the unmodified and ketone-modified protein. In order to probe ketone formation, ketone functionalized protein was conjugated to aminooxy-5(6)-TAMRA dye in the presence of 10 mM of aniline, incubating at 37° C. After 2 hours, extra TAMRA dye was filtered with 3.5 kDa cut off spin filter. Protein conjugated with aminooxy-5(6)-TAMRA was analyzed with fast protein liquid chromatography (FPLC) monitoring at 555 nm, which corresponds to TAMRA dye emission.

Bioconjugation of EGF Protein to Polymer Fiber Mat

Oxime chemistry was used to conjugate ketone-EGF (either control EGF or EGF-MMP) to the aminooxy amine-modified-PCL fiber mat. First, the fiber mats were placed in 20 mL scintillation vials and a solution of EGF (60 µg/mL) was added to the vial. 1% v/v of aniline was added as a catalyst and the reaction proceeded for 2 hours at 37° C. After 2 hours, the fiber mats were removed from the EGF solution and rigorously washed with PBS buffer to completely remove free EGF and catalyst. Complete removal of excess protein was monitored by measuring the waste PBS at 280 nm via UV-Vis spectroscopy. For all FPLC experiments, 2 column volumes of mobile phase (50 mM phosphate buffer, 150 mM NaCl, pH 7.4) was passed at a flow rate of 0.4 mL/min.

ATR-FTIR Measurement for Affinity of EGF-MMP on the Alkoxyamine PCL Fiber Mat 1 cm×1 cm of PCL fiber mat was prepared and soaked in 20 mg of aminooxy benzophenone in MeOH in the same manner described previously. Only one side of the sample was exposed to the UV source and then washed in pure MeOH to remove unreacted aminooxy benzophenone. To confirm the specific attachment of ketone functionalized EGF-MMP to the aminooxy benzophenone-PCL fiber mat, oxime click chemistry was performed following the same bioconjugation procedure previously described. After washing and drying of the fiber mat, ATR-FTIR was utilized to investigate the presence of EGF-MMP on both sides of the PCL fiber mat.

EGF Release Kinetic by MMP-9

Control EGF or EGF-MMP conjugated fiber mats were prepared (n=3) stored in 2 mL of PBS buffer. In order to activate MMP-9 enzyme, amino-phenyl mercuric acetate (APMA) (3.5 mg, 10 mmol) was dissolved in 1 ml of DMSO and then the solution was diluted with reaction buffer (50 mM Tris-HCL pH 7.4, 1 mM CaCl2, 0.05% Triton X-100) to a final concentration of 2 mM APMA in solution. 100 µL of APMA solution was added to 900 µL of phosphate buffer (50 mM phosphate buffer with 500 mM NaCl, pH 7.4) and then, 200 nM of MMP-9 (1 µL) was added and reacted for 16 hours at 37° C. The protein conjugated PCL fiber mat was soaked in 1 mL of phosphate buffer in an Eppendorf tube (n=3). 10 µL of activated MMP-9 was added to each sample, after 10 minutes the buffer was collected and 1 mL of fresh phosphate buffer with 10 µL of activated MMP-9 solution was added to fiber mats. This process was repeated at time points of 10, 30, 60 and 120 minutes.

The released EGF samples from the fiber mat conjugated with either control EGF or EGF-MMP was evaluated via indirect ELISA. An EGF standard curve was generated using concentrations from 100 to 1 ng/mL of recombinant human EGF to determine the concentration of the released protein and released samples were plated at 1× or 10× dilutions. Nunc Maxisorp 96-well plates were coated with 50 µL of EGF at 4° C. overnight.

PBS, pH 7.4) at room temperature for 2 hours. The wells were then incubated with mouse anti-EGF IgG at 5 µg/mL in 100 µL blocking buffer for 2 hours at room temperature. The wells were then incubated with 100 µL of 100 ng/mL of horseradish peroxidase labeled goat anti-mouse IgG in blocking buffer for 2 hours at room temperature. The wells were washed between each incubation step using 4×300 µL of 0.1% w/v Tween-20 in PBS, pH 7.4. The wells were developed using 100 µL of 1-step TMB substrate at 4° C. for 10 minutes. The reaction was stopped with 50 µL of 2 M H2SO4 and the absorbance was read at 450 and 540 nm in triplicate for each sample. The absorbance at 450 nm was subtracted from the absorbance at 540 nm and the EGF concentration in the released sample was determined via comparison to the standard curve and correction via the dilution factor if necessary.

Cell Viability Test

HaCaT and A431 cells were grown and maintained in Dulbecco's Modified Eagle Medium (DMEM) supplemented with 10% newborn calf serum (NCS) (Omega Scientific), 1 mM sodium pyruvate, 1% of penicillin/streptomycin, and 2 mM GlutaMax. Cells were grown at 37° C. in a humidified 5% $CO_2$ and 95% air atmosphere. Cells used for in-vitro experiments were used at passage numbers less than 15. A431 and HaCaT cells were plated in 96-well plates in triplicate (104 cells/well) in 100 µL of complete DMEM. After 18 hours, the media was replaced with serum free media and incubated for 6 hours. Following serum starvation, EGF prepared in serum-free DMEM (100 µL/well) was added at the indicated concentrations to the cells and allowed to incubate for 72 hours at 37° C. Cells were then assayed for viability using the MTT assay. MTT (5 mg/mL in DPBS) was combined with complete DMEM (85:15 DMEM: MTT, 25 µL/well) and added to each individual well and incubated at 37° C. for approximately 2 hours (the assay was stopped when significant accumulation of purple formazan crystals was visibly observed in control wells). Media was carefully aspirated and DMSO was added (200 µL/well) to dissolve the purple MTT-formazan crystals. Absorbance of the dissolved formazan was quantified at 570 nm using a UV-Vis plate reader and cell viability was determined as a fraction of absorbance relative to untreated control wells. The average values are presented with standard deviation.

Scratch Cell Migration Test

Fiber mats were sterilized with 70% ethanol and dried, then a fiber mat was fixed on the side wall of each well in a 12 well culture plate with nail polish. HaCaT cells grown in DMEM supplemented with 10% FBS and 1% penicillin/streptomycin were seeded onto each well of 12 well tissue culture plate ($1 \times 10^6$ cells per well). Cell confluence reached around 80% as a monolayer after 48 hours. The monolayer was gently and slowly scratched with a sterilized 10 μL pipette tip across the center of the well in a straight line in one direction. The resulting scratch was imaged via optical microscopy. Each well was washed twice with PBS to remove detached cells and the wells were replenished with serum free medium. 10 μL of activated MMP-9 was added to each well. After 24 hours, cells were imaged again and ImageJ was utilized to measure scratch distance.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, I claim:

1. A polymer nanofiber scaffold comprising:

a plurality of melt extruded polymer nanofibers, the nanofibers each having a rectangular cross-section defined in part by an encapsulating polymer material that is separated from the nanofibers, the nanofibers including a plurality of click-reactive functional groups extending from portions of outer surfaces of the nanofibers, the functional groups being chemically bound to the nanofibers without degrading polymers chains of the nanofibers.

2. The scaffold of claim 1, wherein concentration of functional groups extending from at least one portion is at least about 0.1 nmol/cm$^2$.

3. The scaffold of claim 1, wherein the functional groups are spatially arranged on the nanofibers such that a first portion of the nanofibers has first concentration of functional groups and second portion of the nanofibers has a second concentration of functional groups different than the concentration of first portion.

4. The scaffold of claim 1, wherein the functional groups are spatially arranged on the nanofibers such that different portions of the nanofibers have different concentrations of the functional groups.

5. The scaffold of claim 1, wherein the functional groups are spatially arranged on the nanofibers in a concentration gradient.

6. The scaffold of claim 1, the plurality of click-reactive function groups including a first click reactive functional groups and second click reactive functional groups different than the first click reactive functional groups.

7. The scaffold of claim 1, wherein the functional groups are chemically bound to the nanofibers with diarylhydroxymethylene linkages that are formed by reaction of a click-reactive functional group substituted diarylketone with the polymer chains of the nanofibers.

8. The scaffold of claim 4, the click-reactive functional groups comprising at least one of an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, —CO$_2$N(COCH$_2$)$_2$, —CO$_2$N (COCH$_2$)$_2$, —CO$_2$H, —CHO, —CHOCH$_2$, —N═C═O, —SO$_2$CH═CH$_2$, —N(COCH)$_2$, —S—S—(C$_5$H$_4$N) and groups of the following structures,

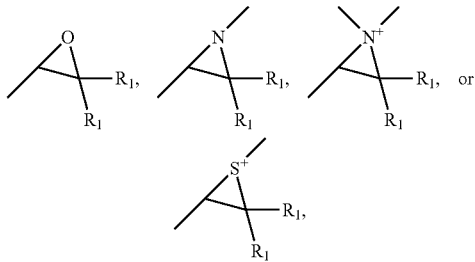

wherein R$_1$ is hydrogen or C$_1$ to C$_4$ alkyl.

9. The scaffold of claim 1, wherein the nanofibers are formed of a polycaprolactone.

10. The scaffold of claim 1, wherein the encapsulating polymer material is a water soluble polymer.

11. A method of forming an agent functionalized polymer nanofiber scaffold, the method comprising:
providing a plurality of melt extruded polymer nanofibers, the nanofibers each having a rectangular cross-section defined in part by an encapsulating polymer material that is separated from the nanofibers,
chemically bonding a plurality of click-reactive functional groups of a specific binding pair to the fibers without degrading polymer chains of the nanofibers, the click-reactive functional groups extending from portions of outer surfaces of the nanofibers; and
appending at least one agent to the nanofibers by reacting an agent conjugated to a complementary click-reactive group of the specific binding pair with the click-reactive functional groups of the nanofibers.

12. The method of claim 11, wherein the agent comprises at least one a bioactive agent, diagnostic agent, therapeutic agent, catalyst, charged molecule, peptide, polypeptide, nucleic acid, polynucleotide, small molecule, nanoparticle, antibody, carbohydrate, or vector.

13. The method of claim 11, the nanofibers are formed by:
coextruding a first polymer material with a second polymer material to form a coextruded polymer film having discrete overlapping layers of polymeric material;
multiplying the overlapping layers to form a multilayered composite film; and
separating the first polymer material from the second polymer material to form the plurality of nanofibers having the rectangular cross-section.

14. The method of claim 13, wherein separating the polymer materials includes subjecting the multilayered composite film to a high pressure water stream.

15. The method of claim 13, wherein separating the polymer materials includes subjecting the multilayered composite film to a high pressure air stream.

16. The method of claim 13, dissolving the second polymer material.

17. The method of claim 11, wherein concentration of functional click-reactive function groups extend from at least one portion is at least about 0.1 nmol/cm$^2$.

18. The method of claim 11, wherein the functional groups are spatially arranged on the nanofibers such that a first portion of the nanofibers has first concentration of functional groups and second a portion of the nanofibers has a second concentration of functional groups different than the concentration of first portion.

19. The method of claim 11, wherein the functional groups are spatially arranged on the nanofibers such that different portions of the nanofibers have different concentrations of the functional groups.

20. The method of claim 11, wherein the functional groups are spatially arranged on the nanofibers in a concentration gradient.

* * * * *